(12) United States Patent
Gurskaya et al.

(10) Patent No.: US 7,432,053 B2
(45) Date of Patent: Oct. 7, 2008

(54) **FLUORESCENT PROTEIN FROM *AEQUOREA COERULSCENS* AND METHODS FOR USING THE SAME**

(75) Inventors: Nadejda G. Gurskaya, Moscow (RU); Arkadiy F. Fradkov, Moscow (RU); Sergey A. Lukyanov, Moscow (RU); Natalia I. Punkova, Moscow (RU)

(73) Assignee: Evrogen, IP, Moscow (RU)

( * ) Notice: Subject to any disclaimer, the term of this patent is extended or adjusted under 35 U.S.C. 154(b) by 302 days.

(21) Appl. No.: 10/501,629

(22) PCT Filed: Jan. 17, 2003

(86) PCT No.: PCT/IB03/00907

§ 371 (c)(1),
(2), (4) Date: Jul. 15, 2004

(87) PCT Pub. No.: WO03/062270

PCT Pub. Date: Jul. 31, 2003

(65) Prior Publication Data

US 2006/0167225 A1     Jul. 27, 2006

Related U.S. Application Data

(60) Provisional application No. 60/351,518, filed on Jan. 22, 2002.

(51) Int. Cl.
| | |
|---|---|
| C12Q 1/68 | (2006.01) |
| C12N 15/00 | (2006.01) |
| C12N 1/20 | (2006.01) |
| C12P 21/06 | (2006.01) |
| C07H 21/02 | (2006.01) |

(52) U.S. Cl. .................... 435/6; 435/252.3; 435/320.1; 435/69.1; 536/23.1

(58) Field of Classification Search ................ 530/350; 435/69.1, 252.3, 320.1, 6; 536/23.1
See application file for complete search history.

(56) References Cited

U.S. PATENT DOCUMENTS

| | | | |
|---|---|---|---|
| 5,625,048 | A | 4/1997 | Tsien et al. |
| 5,777,079 | A | 7/1998 | Tsien et al. |
| 5,968,750 | A | 10/1999 | Zolotukhin et al. |
| 6,096,865 | A | 8/2000 | Michaels |
| 6,919,186 | B2 * | 7/2005 | Stubbs et al. .............. 435/69.1 |

FOREIGN PATENT DOCUMENTS

WO     WO 00/34326     6/2000

OTHER PUBLICATIONS

Gurskaya, et al., "A Colourless Green Fluorescent Protein Homologue from the Non-Fluorescent Hydromedusa *Aequorea coerulescens* and its Fluorescent Mutants," Biochem. J. (2003) 373, 403-408.
Matz, et al., "Fluorescent Proteins from Nonbioluminescent Anthozoa Species," Nature Biotechnology vol. 17 Oct. 1999.
Inouye, et al., "Expression of the Gene and Fluorescence Characteristics of the Recombinant Protein," FEBS Letters 341 (1994) 277-280.
Prasher, et al., "Primary Structure of the Aequorea Victoria Green-Fluorescent Protein," Gene, 111 (1992) 229-233.
International Seach Report, dated Sep. 15, 2003 for PCT/IB/00907.

* cited by examiner

*Primary Examiner*—Maryam Monshipouri
(74) *Attorney, Agent, or Firm*—Patterson & Sheridan, L.L.P.

(57) ABSTRACT

The present invention provides nucleic acid compositions encoding a novel colorless GFP-like protein, acGFP, from *Aequorea coerulscens* and fluorescent and non-fluorescent mutants and derivatives thereof, as well as peptides and proteins encoded by these nucleic acid compositions. The subject protein and nucleic acid compositions of the present invention are colored and/or fluorescent and/or can be photoactivated, and can be used in a variety of different biological applications, particularly for labeling. Finally, kits for use in such biological applications are provided.

16 Claims, 23 Drawing Sheets

```
       10         20         30         40         50         60
5'ATTCAAAACACTGCAGAATTTTGGATAGATTTTCCTGCTACTTCACACGCATAAAAGACA 70         80         90        100        110        120
AGAAAGATGAGTAAAGGAGCAGAACTTTTCACTGGAGTTGTCCCAATTCTTATTGAATTA
      M  S  K  G  A  E  L  F  T  G  V  V  P  I  L  I  E  L 130        140        150        160        170        180
AATGGTGATGTTAATGGGCACAAATTCTCTGTCAGTGGAGAGGGCGAAGGTGATGCGACA
 N  G  D  V  N  G  H  K  F  S  V  S  G  E  G  E  G  D  A  T 190        200        210        220        230        240
TACGGAAAGTTAACCCTTAAATTTATTTGCACTACAGGAAAACTACCTGTTCCATGGCCA
 Y  G  K  L  T  L  K  F  I  C  T  T  G  K  L  P  V  P  W  P 250        260        270        280        290        300
ACACTTGTCACTACTTTCTCTTATGGTGTTCAATGCTTTTCAAGATATCCAGATCATATG
 T  L  V  T  T  F  S  Y  G  V  Q  C  F  S  R  Y  P  D  H  M 310        320        330        340        350        360
AAACAGCATGACTTCTTCAAGAGTGCCATGCCTGAAGGTTATATACAGGAAAGAACTATA
 K  Q  H  D  F  F  K  S  A  M  P  E  G  Y  I  Q  E  R  T  I 370        380        390        400        410        420
TTTTTCAAAGATGACGGGAACTACAAGTCGCGTGCTGAAGTCAAGTTCGAAGGTGATACC
 F  F  K  D  D  G  N  Y  K  S  R  A  E  V  K  F  E  G  D  T 430        440        450        460        470        480
CTGGTTAATAGAATTGAGTTAACAGGTACTGATTTTAAAGAAGATGGAAACATCCTTGGA
 L  V  N  R  I  E  L  T  G  T  D  F  K  E  D  G  N  I  L  G 490        500        510        520        530        540
AATAAAATGGAATACAACTATAACGCACATAATGTATACATCATGACAGACAAAGCAAAA
 N  K  M  E  Y  N  Y  N  A  H  N  V  Y  I  M  T  D  K  A  K 550        560        570        580        590        600
AATGGAATCAAAGTTAACTTCAAAATTAGACACAACATTGAAGATGGAAGCGTTCAACTT
 N  G  I  K  V  N  F  K  I  R  H  N  I  E  D  G  S  V  Q  L 610        620        630        640        650        660
GCAGACCATTATCAACAAAATACTCCAATTGGCGATGGCCCTGTCCTTTTACCAGATAAC
 A  D  H  Y  Q  Q  N  T  P  I  G  D  G  P  V  L  L  P  D  N 670        680        690        700        710        720
CATTACCTGTCCACACAATCTACCCTTTCCAAAGATCCCAACGAAAAGAGAGATCACATG
 H  Y  L  S  T  Q  S  T  L  S  K  D  P  N  E  K  R  D  H  M 730        740        750        760        770        780
ATCTATTTTGAGTTTGTAACAGCTGCTGCGATTACACATGGCATGGATGAATTATACAAA
 I  Y  F  E  F  V  T  A  A  A  I  T  H  G  M  D  E  L  Y  K 790        800        810        820        830        840
TAAATGTATAGACTTCAAGTTGACACTAACGTGTCCGAACAATTACTAAAATCTCAGGGT 850        860        870        880        890        900
TCCTGGTTAAAATCAGGCTGAGATATTATTTACATATTATAGATTCATTAGAATTATTTA 910        920        930        940
AATACTTTATAGATGTTATTGATAGGGGTTATTTTCTTATT 3'
```

FIG. 1

```
              10         20         30         40         50
GFP    MSKGEELFTGVVPILVELDGDVNGHKFSVSGEGEGDATYGKLTLKFICTTGKLP
acGFP  ----A--------N-------------------------------
           I 60         70         80         90        100        110
GFP    VPWPTLVTTFSYGVQCFSRYPDHMKQHDFFKSAMPEGYVQERTIFFKDDGNYKTRAEVK
acGFP  ---------------------------I----------------
           L                                       E 120        130        140        150        160        170
GFP    FEGDTLVNRIELKGIDFKEDGNILGHKLEYNYNSHNVYIMADKQKNGIKVNFKIRHNIEDGSVQL
acGFP  -----------T-T---------N-M------A-----T--A------------
       -

180        190        200        210        220        230
GFP    ADHYQQNTPIGDGPVLLPDNHYLSTQSALSKDPNEKRDHMVLLEFVTAAGITHGMDELYK
acGFP  ---------------------T----------IMF------A---
       ------                          A           G
```

FIG. 2

```
  1  ATG AGT AAA GGA GCA GAA CTT TTC ACT GGA GTT GTC CCA ATT CTT ATT   48
  1   M   S   K   G   A   E   L   F   T   G   V   V   P   I   L   I   16

49  GAA TTA AAT GGT GAT GTT AAT GGG CAC AAA TTC TCT GTC AGT GGA GAG   96
 17   E   L   N   G   D   V   N   G   H   K   F   S   V   S   G   E   32

97  GGC GAA GGT GAT GCG ACA TAC GGA AAG TTA ACC CTT AAA TTT ATT TGC  144
 33   G   E   G   D   A   T   Y   G   K   L   T   L   K   F   I   C   48

145  ACT ACA GGA AAA CTA CCT GTT CCA TGG CCA ACA CTT GTC ACT ACT TTC  192
 49   T   T   G   K   L   P   V   P   W   P   T   L   V   T   T   F   64

193  TCT TAT GGT GTT CAA TGC TTT TCA AGA TAT CCA GAT CAT ATG AAA CAG  240
 65   S   Y   G   V   Q   C   F   S   R   Y   P   D   H   M   K   Q   80

241  CAT GAC TTC TTC AAG AGT GCC ATG CCT GAA GGT TAT ATA CAG GAA AGA  288
 81   H   D   F   F   K   S   A   M   P   E   G   Y   I   Q   E   R   96

289  ACT ATA TTT TTC AAA GAT GAC GGG AAC TAC AAG TCG CGT GCT GAA GTC  336
 97   T   I   F   F   K   D   D   G   N   Y   K   S   R   A   E   V  112

337  AAG TTC GAA GGT GAT ACC CTG GTT AAT AGA ATT GAG TTA ACA GGT ACT  384
113   K   F   E   G   D   T   L   V   N   R   I   E   L   T   G   T  128

385  GAT TTT AAA GAA GAT GGA AAC ATC CTT GGA AAT AAA ATG GAA TAC AAC  432
129   D   F   K   E   D   G   N   I   L   G   N   K   M   E   Y   N  144

433  TAT AAC GCA CAT AAT GTA TAC ATC ATG ACA GAC AAA GCA AAA AAT GGA  480
145   Y   N   A   H   N   V   Y   I   M   T   D   K   A   K   N   G  160

481  ATC AAA GTT AAC TTC AAA ATT AGA CAC AAC ATT GAA GAT GGA AGC GTT  528
161   I   K   V   N   F   K   I   R   H   N   I   E   D   G   S   V  176

529  CAA CTT GCA GAC CAT TAT CAA CAA AAT ACT CCA ATT GGC GAT GGC CCT  576
177   Q   L   A   D   H   Y   Q   Q   N   T   P   I   G   D   G   P  192

577  GTC CTT TTA CCA GAT AAC CAT TAC CTG TCC ACA CAA TCT ACC CTT TCC  624
193   V   L   L   P   D   N   H   Y   L   S   T   Q   S   T   L   S  208

625  AAA GAT CCC AAC GAA AAG AGA GAT CAC ATG ATC TAT TTT GGG TTT GTA  672
209   K   D   P   N   E   K   R   D   H   M   I   Y   F   G   F   V  224

673  ACA GCT GCT GCG ATT ACA CAT GGC ATG GAT GAA TTA TAC AAA TAA       717
225   T   A   A   A   I   T   H   G   M   D   E   L   Y   K   *       239
```

FIG. 3

```
  1 ATG AGT AAA GGA GCA GAA CTT TTC ACT GGA GTT GTC CCA ATT CTT ATT    48
  1  M   S   K   G   A   E   L   F   T   G   V   V   P   I   L   I    16

49 GAA TTA GAT GGT GAT GTT AAT GGG CAC AAA TTC TCT GTC AGT GGA GAG    96
 17  E   L   D   G   D   V   N   G   H   K   F   S   V   S   G   E    32

97 GGC GAA GGT GAT GCG ACA TAC GGA AAG TTA ACC CTT AAA TTT ATT TGC   144
 33  G   E   G   D   A   T   Y   G   K   L   T   L   K   F   I   C    48

145 ACT ACA GGA AAA CTA CCT GTT CCA TGG CCA ACA CTT GTC ACT ACT TTC   192
 49  T   T   G   K   L   P   V   P   W   P   T   L   V   T   T   F    64

193 TCT TAT GGT GTT CAA TGC TTT TCA AGA TAT CCA GAT CAT ATG AAA CAG   240
 65  S   Y   G   V   Q   C   F   S   R   Y   P   D   H   M   K   Q    80

241 CAT GAC TTC TTC AAG AGT GCC ATG CCT GAA GGT TAT ATA CAG GAA AGA   288
 81  H   D   F   F   K   S   A   M   P   E   G   Y   I   Q   E   R    96

289 ACT ATA TTT TTC AAA GAT GAC GGG AAC TAC AAG TCG CGT GCT GAA GTC   336
 97  T   I   F   F   K   D   D   G   N   Y   K   S   R   A   E   V   112

337 AAG TTC GAA GGT GAT ACC CTG GTT AAT AGA ATT GAG TTA ACA GGT ACT   384
113  K   F   E   G   D   T   L   V   N   R   I   E   L   T   G   T   128

385 GAT TTT AAA GAA GAT GGA AAC ATC CTT GGA AAT AAA ATG GAA TAC AAC   432
129  D   F   K   E   D   G   N   I   L   G   N   K   M   E   Y   N   144

433 TAT AAC GCA CAT AAT GTA TAC ATC ATG ACA GAC AAA GCA AAA AAT GGA   480
145  Y   N   A   H   N   V   Y   I   M   T   D   K   A   K   N   G   160

481 ATC AAA GTT AAC TTC AAA ATT AGA CAC AAC ATT GAA GAT GGA AGC GTT   528
161  I   K   V   N   F   K   I   R   H   N   I   E   D   G   S   V   176

529 CAA CTT GCA GAC CAT TAT CAA CAA AAT ACT CCA ATT GGC GAT GGC CCT   576
177  Q   L   A   D   H   Y   Q   Q   N   T   P   I   G   D   G   P   192

577 GTC CTT TTA CCA GAT AAC CAT TAC CTG TCC ACA CAA TCT ACC CTT TCC   624
193  V   L   L   P   D   N   H   Y   L   S   T   Q   S   T   L   S   208

625 AAA GAT CCC AAC GAA AAG AGA GAT CAC ATG ATC TAT TTT GGG TTT GTA   672
209  K   D   P   N   E   K   R   D   H   M   I   Y   F   G   F   V   224

673 ACA GCT GCT GCG ATT ACA CAT GGC ATG GAT GAA TTA TAC AAA TAA       717
225  T   A   A   A   I   T   H   G   M   D   E   L   Y   K   *       239
```

FIG. 5

```
  1  ATG AGT AAA GGA GCA GAA CTT TTC ACT GGA ATT GTC CCA ATT CTT ATT        48
  1   M   S   K   G   A   E   L   F   T   G   I   V   P   I   L   I         16

49  GAA TTA AAT GGT GAT GTT AAT GGG CAC AAA TTC TCT GTC AGT GGA GAG         96
 17   E   L   N   G   D   V   N   G   H   K   F   S   V   S   G   E         32

97  GGC GAA GGT GAT GCG ACA TAC GGA AAG TTA ACC CTT AAA TTT ATT TGC        144
 33   G   E   G   D   A   T   Y   G   K   L   T   L   K   F   I   C         48

145  ACT ACA GGA AAA CTA TGA CCT GTT CCA TGG CCA ACA CTT GTC ACT ACT        192
 49   T   T   G   K   L   *   P   V   P   W   P   T   L   V   T   T         64

193  TTC TCT TAT GGT GTT CAA TGC TTT TCA AGA TAT CCA GAT CAT ATG AAA        240
 65   F   S   Y   G   V   Q   C   F   S   R   Y   P   D   H   M   K         80

241  CAG CAT GAC TTC TTC AAG AGT GCC ATG CCT GAA GGT TAT ATA CAG GAA        288
 81   Q   H   D   F   F   K   S   A   M   P   E   G   Y   I   Q   E         96

289  AGA ACT ATA TTT TTC GAA GAT GAC GGG AAC TAC AAG TCG CGT GCT GAA        336
 97   R   T   I   F   F   E   D   D   G   N   Y   K   S   R   A   E        112

337  GTC AAG TTC GAA GGT GAT ACC CTG GTT AAT AGA ATT GAG TTA ACA GGT        384
113   V   K   F   E   G   D   T   L   V   N   R   I   E   L   T   G        128

385  ACT GAT TTT AAA GAA GAT GGA AAC ATC CTT GGA AAT AAA ATG GAA TAC        432
129   T   D   F   K   E   D   G   N   I   L   G   N   K   M   E   Y        144

433  AAC TAT AAC GCA CAT AAT GTA TAC ATC ATG ACA GAC AAA GCA AAA AAT        480
145   N   Y   N   A   H   N   V   Y   I   M   T   D   K   A   K   N        160

481  GGA ATC AAA GTT AAC TTC AAA ATT AGA CAC AAC ATT GAA GAT GGA AGC        528
161   G   I   K   V   N   F   K   I   R   H   N   I   E   D   G   S        176

529  GTT CAA CTT GCA GAC CAT TAT CAA CAA AAT ACT CCA ATT GGC GAT GGC        576
177   V   Q   L   A   D   H   Y   Q   Q   N   T   P   I   G   D   G        192

577  CCT GTC CTT TTA CCA GAT AAC CAT TAC CTG TCC ACA CAA TCT ACC CTT        624
193   P   V   L   L   P   D   N   H   Y   L   S   T   Q   S   T   L        208

625  TCC AAA GAT CCC AAC GAA AAG AGA GAT CAC ATG ATC TAT TTT GGG TTT        672
209   S   K   D   P   N   E   K   R   D   H   M   I   Y   F   G   F        224

673  GTA ACA GCT GCT GCG ATT ACA CAT GGC ATG GAT GAA TTA TAC AAA TAA        720
225   V   T   A   A   A   I   T   H   G   M   D   E   L   Y   K   *        240
```

FIG. 6

```
  1  ATG AGT AAA GGA GCA GAA CTT TTC ACT GGA ATT GTC CCA ATT CTT ATT    48
  1   M   S   K   G   A   E   L   F   T   G   I   V   P   I   L   I    16

49  GAA TTA AAT GGT GAT GTT AAT GGG CAC AAA TTC TCT GTC AGT GGA GAG    96
 17   E   L   N   G   D   V   N   G   H   K   F   S   V   S   G   E    32

97  GGC GAA GGT GAT GCG ACA TAC GGA AAG TTA ACC CTT AAA TTT ATT TGC   144
 33   G   E   G   D   A   T   Y   G   K   L   T   L   K   F   I   C    48

145  ACT ACA GGA AAA CTA CCT GTT CCA TGG CCA ACA CTT GTC ACT ACT GTC   192
 49   T   T   G   K   L   P   V   P   W   P   T   L   V   T   T   L    64

193  TCT TAT GGT GTT CAA TGC TTT TCA AGA TAT CCA GAT CAT ATG AAA CAG   240
 65   S   Y   G   V   Q   C   F   S   R   Y   P   D   H   M   K   Q    80

241  CAT GAC TTC TTC AAG AGT GCC ATG CCT GAA GGT TAT ATA CAG GAA AGA   288
 81   H   D   F   F   K   S   A   M   P   E   G   Y   I   Q   E   R    96

289  ACT ATA TTT TTC GAA GAT GAC GGG AAC TAC AAG TCG CGT GCT GAA GTC   336
 97   T   I   F   F   E   D   D   G   N   Y   K   S   R   A   E   V   112

337  AAG TTC GAA GGT GAT ACC CTG GTT AAT AGA ATT GAG TTA ACA GGT ACT   384
113   K   F   E   G   D   T   L   V   N   R   I   E   L   T   G   T   128

385  GAT TTT AAA GAA GAT GGA AAC ATC CTT GGA AAT AAA ATG GAA TAC AAC   432
129   D   F   K   E   D   G   N   I   L   G   N   K   M   E   Y   N   144

433  TAT AAC GCA CAT AAT GTA TAC ATC ATG ACA GAC AAA GCA AAA AAT GGA   480
145   Y   N   A   H   N   V   Y   I   M   T   D   K   A   K   N   G   160

481  ATC AAA GTT AAC TTC AAA ATT AGA CAC AAC ATT GAA GAT GGA AGC GTT   528
161   I   K   V   N   F   K   I   R   H   N   I   E   D   G   S   V   176

529  CAA CTT GCA GAC CAT TAT CAA CAA AAT ACT CCA ATT GGC GAT GGC CCT   576
177   Q   L   A   D   H   Y   Q   Q   N   T   P   I   G   D   G   P   192

577  GTC CTT TTA CCA GAT AAC CAT TAC CTG TCC ACA CAA TCT ACC CTT TCC   624
193   V   L   L   P   D   N   H   Y   L   S   T   Q   S   T   L   S   208

625  AAA GAT CCC AAC GAA AAG AGA GAT CAC ATG ATC TAT TTT GGG TTT GTA   672
209   K   D   P   N   E   K   R   D   H   M   I   Y   F   G   F   V   224

673  ACA GCT GCT GCG ATT ACA CAT GGC ATG GAT GAA TTA TAC AAA TAA       717
225   T   A   A   A   I   T   H   G   M   D   E   L   Y   K   *       239
```

FIG. 7

| | | | | | | | | | | | | | | | | | |
|---|---|---|---|---|---|---|---|---|---|---|---|---|---|---|---|---|---|
|1|ATG|AGT|AAA|GGA|GCA|GAA|CTT|TTC|ACT|GGA|ATT|GTC|CCA|ATT|CTT|ATT|48|
|1|M|S|K|G|A|E|L|F|T|G|I|V|P|I|L|I|16|

|  |  |  |  |  |  |  |  |  |  |  |  |  |  |  |  |  |  |
|---|---|---|---|---|---|---|---|---|---|---|---|---|---|---|---|---|---|
|49|GAA|TTA|AAT|GGT|GAT|GTT|AAT|GGG|CAC|AAA|TTC|TCT|GTC|AGT|GGA|GAG|96|
|17|E|L|N|G|D|V|N|G|H|K|F|S|V|S|G|E|32|

|  |  |  |  |  |  |  |  |  |  |  |  |  |  |  |  |  |  |
|---|---|---|---|---|---|---|---|---|---|---|---|---|---|---|---|---|---|
|97|GGC|GAA|GGT|GAT|GCG|ACA|TAC|GGA|AAG|TTA|ACC|CTT|AAA|TTT|ATT|TGC|144|
|33|G|E|G|D|A|T|Y|G|K|L|T|L|K|F|I|C|48|

|  |  |  |  |  |  |  |  |  |  |  |  |  |  |  |  |  |  |
|---|---|---|---|---|---|---|---|---|---|---|---|---|---|---|---|---|---|
|145|ACT|ACA|GGA|AAA|CTA|CCT|GTT|CCA|TGG|CCA|ACA|CTT|GTC|ACT|ACT|GTC|192|
|49|T|T|G|K|L|P|V|P|W|P|T|L|V|T|T|V|64|

|  |  |  |  |  |  |  |  |  |  |  |  |  |  |  |  |  |  |
|---|---|---|---|---|---|---|---|---|---|---|---|---|---|---|---|---|---|
|193|TCT|TAT|GGT|GTT|CAA|TGC|TTT|TCA|AGA|TAT|CCA|GAT|CAT|ATG|AAA|CAG|240|
|65|S|Y|G|V|Q|C|F|S|R|Y|P|D|H|M|K|Q|80|

|  |  |  |  |  |  |  |  |  |  |  |  |  |  |  |  |  |  |
|---|---|---|---|---|---|---|---|---|---|---|---|---|---|---|---|---|---|
|241|CAT|GAC|TTC|TTC|AAG|AGT|GCC|ATG|CCT|GAA|GGT|TAT|ATA|CAG|GAA|AGA|288|
|81|H|D|F|F|K|S|A|M|P|E|G|Y|I|Q|E|R|96|

|  |  |  |  |  |  |  |  |  |  |  |  |  |  |  |  |  |  |
|---|---|---|---|---|---|---|---|---|---|---|---|---|---|---|---|---|---|
|289|ACT|ATA|TTT|TTC|GAA|GAT|GAC|GGG|AAC|TAC|AAG|TCG|CGT|GCT|GAA|GTC|336|
|97|T|I|F|F|E|D|D|G|N|Y|K|S|R|A|E|V|112|

|  |  |  |  |  |  |  |  |  |  |  |  |  |  |  |  |  |  |
|---|---|---|---|---|---|---|---|---|---|---|---|---|---|---|---|---|---|
|337|AAG|TTC|GAG|GGT|GAT|ACC|CTG|GTT|AAT|AGA|ATC|GAG|TTA|ACA|GGT|ACT|384|
|113|K|F|E|G|D|T|L|V|N|R|I|E|L|T|G|T|128|

|  |  |  |  |  |  |  |  |  |  |  |  |  |  |  |  |  |  |
|---|---|---|---|---|---|---|---|---|---|---|---|---|---|---|---|---|---|
|385|GAT|TTT|AAA|GAA|GAT|GGA|AAC|ATC|CTT|GGA|AAT|AAA|ATG|GAA|TAC|AAC|432|
|129|D|F|K|E|D|G|N|I|L|G|N|K|M|E|Y|N|144|

|  |  |  |  |  |  |  |  |  |  |  |  |  |  |  |  |  |  |
|---|---|---|---|---|---|---|---|---|---|---|---|---|---|---|---|---|---|
|433|TAT|AAC|GCA|CAT|AAT|GTA|TAC|ATC|ATG|ACA|GAC|AAA|GCA|AAA|AAT|GGA|480|
|145|Y|N|A|H|N|V|Y|I|M|T|D|K|A|K|N|G|160|

|  |  |  |  |  |  |  |  |  |  |  |  |  |  |  |  |  |  |
|---|---|---|---|---|---|---|---|---|---|---|---|---|---|---|---|---|---|
|481|ATC|AAA|GTT|AAC|TTC|AAA|ATT|AGA|CAC|AAC|ATT|GAA|GAT|GGA|AGC|GTT|528|
|161|I|K|V|N|F|K|I|R|H|N|I|E|D|G|S|V|176|

|  |  |  |  |  |  |  |  |  |  |  |  |  |  |  |  |  |  |
|---|---|---|---|---|---|---|---|---|---|---|---|---|---|---|---|---|---|
|529|CAA|CTT|GCA|GAC|CAT|TAT|CAA|CAA|AAT|ACT|CCA|ATT|GGC|GAT|GGC|CCT|576|
|177|Q|L|A|D|H|Y|Q|Q|N|T|P|I|G|D|G|P|192|

|  |  |  |  |  |  |  |  |  |  |  |  |  |  |  |  |  |  |
|---|---|---|---|---|---|---|---|---|---|---|---|---|---|---|---|---|---|
|577|GTC|CTT|TTA|CCA|GAT|AAC|CAT|TAC|CTG|TCC|ACA|CAA|TCT|GCC|CTT|TCC|624|
|193|V|L|L|P|D|N|H|Y|L|S|T|Q|S|A|L|S|208|

|  |  |  |  |  |  |  |  |  |  |  |  |  |  |  |  |  |  |
|---|---|---|---|---|---|---|---|---|---|---|---|---|---|---|---|---|---|
|625|AAA|GAT|CCC|AAC|GAA|AAG|AGA|GAT|CAC|ATG|ATC|TAT|TTT|GGG|TTT|GTA|672|
|209|K|D|P|N|E|K|R|D|H|M|I|Y|F|G|F|V|224|

|  |  |  |  |  |  |  |  |  |  |  |  |  |  |  |  |  |
|---|---|---|---|---|---|---|---|---|---|---|---|---|---|---|---|---|
|673|ACA|GCT|GCT|GCG|ATT|ACA|CAT|GGC|ATG|GAT|GAA|CTA|TAC|AAA|TAA|717|
|225|T|A|A|A|I|T|H|G|M|D|E|L|Y|K|*|239|

FIG. 9

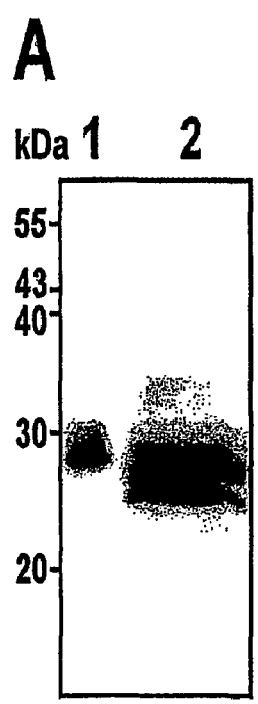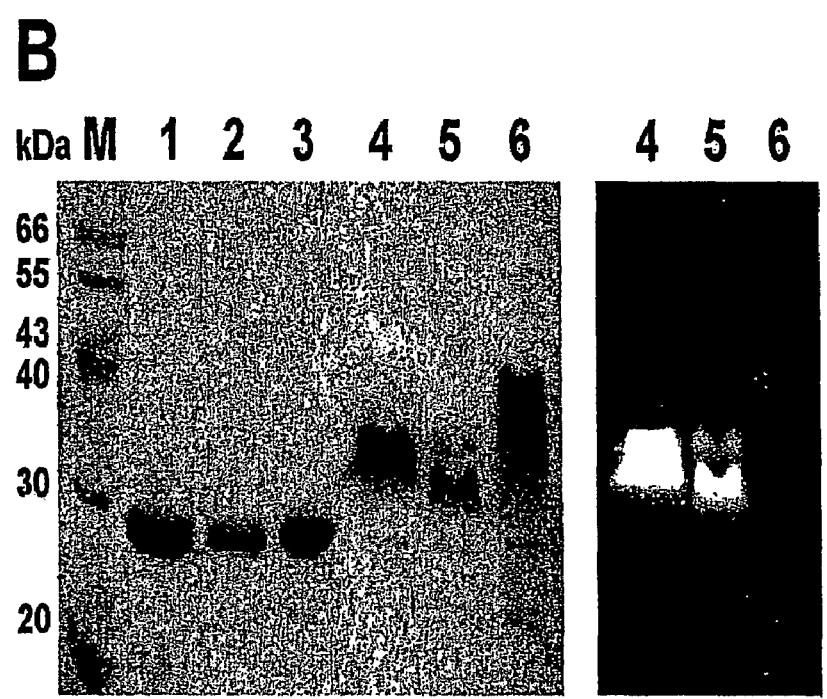
FIG. 11a    FIG. 11b    FIG. 11c

```
  1  ATG AGT AAA GGA GCA GAA CTT TTC ACT GGA ATT GTC CCA ATT CTT ATT    48
  1   M   S   K   G   A   E   L   F   T   G   I   V   P   I   L   I    16

49  GAA TTA AAT GGT GAT GTT AAT GGG CAC AAA TTC TCT GTC AGT GGA GAG    96
 17   E   L   N   G   D   V   N   G   H   K   F   S   V   S   G   E    32

97  GGC GAA GGT GAT GCG ACA TAC GGA AAG TTA ACC CTT AAA TTT ATT TGC   144
 33   G   E   G   D   A   T   Y   G   K   L   T   L   K   F   I   C    48

145  ACT ACA GGA AAA CTA CCT GTT CCA TGG CCA ACA CTT GTC ACT ACT GTC   192
 49   T   T   G   K   L   P   V   P   W   P   T   L   V   T   T   V    64

193  TCT TAT GGT GTT CAA TGC TTT TCA AGA TAT CCA GAT CAT ATG AAA CAG   240
 65   S   Y   G   V   Q   C   F   S   R   Y   P   D   H   M   K   Q    80

241  CAT GAC TTC TTC AAG AGT GCC ATG CCT GAA GGT TAT ATA CAG GAA AGA   288
 81   H   D   F   F   K   S   A   M   P   E   G   Y   I   Q   E   R    96

289  ACT ATA TTT TTC GAA GAT GAC GGG AAC TAC AAG TCG CGT GCT GAA GTC   336
 97   T   I   F   F   E   D   D   G   N   Y   K   S   R   A   E   V   112

337  AAG TTC GAG GGT GAT ACC CTG GTT AAT AGA ATC GAG TTA ACA GGT ACT   384
113   K   F   E   G   D   T   L   V   N   R   I   E   L   T   G   T   128

385  GAT TTT AAA GAA GAT GGA AAC ATC CTT GGA AAT AAA ATG GAA TAC AAC   432
129   D   F   K   E   D   G   N   I   L   G   N   K   M   E   Y   N   144

433  TAT AAC GCA CAT AAT GTA TAC ATC ATG ACA GAC AAA GCA AAA AAT GGA   480
145   Y   N   A   H   N   V   Y   I   M   T   D   K   A   K   N   G   160

481  ATC AAA GTT AAC TTC AAA ATT AGA CAC AAC ATT GAA GAT GGA AGC GTT   528
161   I   K   V   N   F   K   I   R   H   N   I   E   D   G   S   V   176

529  CAA CTT GCA GAC CAT TAT CAA CAA AAT ACT CCA ATT GGC GAT GGC CCT   576
177   Q   L   A   D   H   Y   Q   Q   N   T   P   I   G   D   G   P   192

577  GTC CTT TTA CCA GAT AAC CAT TAC CTG TCC ACA CAA TCT GCC CTT TCC   624
193   V   L   L   P   D   N   H   Y   L   S   T   Q   S   A   L   S   208

625  AAA GAT CCC AAC GAA AAG AGA GAT CAC ATG ATC TAT TTT GAG TTT GTA   672
209   K   D   P   N   E   K   R   D   H   M   I   Y   F   E   F   V   224

673  ACA GCT GCT GCG ATT ACA CAT GGC ATG GAT GAA CTA TAC AAA TAA       717
225   T   A   A   A   I   T   H   G   M   D   E   L   Y   K   *       239
```

FIG. 12

```
  1  ATG AGT AAA GGA GCA GAA CTT TTC ACT GGA ATT GTC CCA ATT CTT ATT   48
  1   M   S   K   G   A   E   L   F   T   G   I   V   P   I   L   I   16

49  GAA TTA AAT GGT GAT GTT AAT GGG CAC AAA TTC TCT GTC AGT GGA GAG   96
 17   E   L   N   G   D   V   N   G   H   K   F   S   V   S   G   E   32

97  GGC GAA GGT GAT GCG ACA TAC GGA AAG TTA ACC CTT AAA TTT ATT TGC  144
 33   G   E   G   D   A   T   Y   G   K   L   T   L   K   F   I   C   48

145  ACT ACA GGA AAA CTA CCT GTT CCA TGG CCA ACA CTT GTC ACT ACT CTC  192
 49   T   T   G   K   L   P   V   P   W   P   T   L   V   T   T   L   64

193  TCT TAT GGT GTT CAA TGC TTT TCA AGA TAT CCA GAT CAT ATG AAA CAG  240
 65   S   Y   G   V   Q   C   F   S   R   Y   P   D   H   M   K   Q   80

241  CAT GAC TTC TTC AAG AGT GCC ATG CCT GAA GGT TAT ATA CAG GAA AGA  288
 81   H   D   F   F   K   S   A   M   P   E   G   Y   I   Q   E   R   96

289  ACT ATA TTT TTC GAA GAT GAC GGG AAC TAC AAG TCG CGT GCT GAA GTC  336
 97   T   I   F   F   E   D   D   G   N   Y   K   S   R   A   E   V  112

337  AAG TTC GAG GGT GAT ACC CTG GTT AAT AGA ATC GAG TTA ACA GGT ACT  384
113   K   F   E   G   D   T   L   V   N   R   I   E   L   T   G   T  128

385  GAT TTT AAA GAA GAT GGA AAC ATC CTT GGA AAT AAA ATG GAA TAC AAC  432
129   D   F   K   E   D   G   N   I   L   G   N   K   M   E   Y   N  144

433  TAT AAC GCA CAT AAT GTA TAC ATC ATG ACA GAC AAA GCA AAA AAT GGA  480
145   Y   N   A   H   N   V   Y   I   M   T   D   K   A   K   N   G  160

481  ATC AAA GTT AAC TTC AAA ATT AGA CAC AAC ATT GAA GAT GGA AGC GTT  528
161   I   K   V   N   F   K   I   R   H   N   I   E   D   G   S   V  176

529  CAA CTT GCA GAC CAT TAT CAA CAA AAT ACT CCA ATT GGC GAT GGC CCT  576
177   Q   L   A   D   H   Y   Q   Q   N   T   P   I   G   D   G   P  192

577  GTC CTT TTA CCA GAT AAC CAT TAC CTG TCC ACA CAA TCT GCC CTT TCC  624
193   V   L   L   P   D   N   H   Y   L   S   T   Q   S   A   L   S  208

625  AAA GAT CCC AAC GAA AAG AGA GAT CAC ATG ATC CTG TTT GAG TTT GTA  672
209   K   D   P   N   E   K   R   D   H   M   I   L   F   E   F   V  224

673  ACA GCT GCT GCG ATT ACA CAT GGC ATG GAT GAA CTA TAC AAA TAA      717
225   T   A   A   A   I   T   H   G   M   D   E   L   Y   K   *      239
```

FIG. 15

```
  1  ATG AGT AAA GGA GCA GAA CTT TTC ACT GGA ATT GTC CCA ATT CTT ATT   48
  1   M   S   K   G   A   E   L   F   T   G   I   V   P   I   L   I   16

49  GAA TTA AAT GGT GAT GTT AAT GGG CAC AAA TTC TCT GTC AGT GGA GAG   96
 17   E   L   N   G   D   V   N   G   H   K   F   S   V   S   G   E   32

97  GGC GAA GGT GAT GCG ACA TAC GGA AAG TTA ACC CTT AAA TTT ATT TGC  144
 33   G   E   G   D   A   T   Y   G   K   L   T   L   K   F   I   C   48

145  ACT ACA GGA AAA CTA CCT GTT CCA TGG CCA ACA CTT GTC ACT ACT CTC  192
 49   T   T   G   K   L   P   V   P   W   P   T   L   V   T   T   L   64

193  TCT TAT GGT GCT CAA TGC TTT TCA AGA TAT CCA GAT CAT ATG AAA CAG  240
 65   S   Y   G   A   Q   C   F   S   R   Y   P   D   H   M   K   Q   80

241  CAT GAC TTC TTC AAG AGT GCC ATG CCT GAA GGT TAT ATA CAG GAA AGA  288
 81   H   D   F   F   K   S   A   M   P   E   G   Y   I   Q   E   R   96

289  ACT ATA TTT TTC GAA GAT GAC GGG AAC TAC AAG TCG CGT GCT GAA GTC  336
 97   T   I   F   F   E   D   D   G   N   Y   K   S   R   A   E   V  112

337  AAG TTC GAG GGT GAT ACC CTG GTT AAT AGA ATC GAG TTA ACA GGT ACT  384
113   K   F   E   G   D   T   L   V   N   R   I   E   L   T   G   T  128

385  GAT TTT AAA GAA GAT GGA AAC ATC CTT GGA AAT AAA ATG GAA TAC AAC  432
129   D   F   K   E   D   G   N   I   L   G   N   K   M   E   Y   N  144

433  TAT AAC GCA CAG AAT GTA TAC ATC ATG ACA GAC AAA GCA AAA AAT GGA  480
145   Y   N   A   Q   N   V   Y   I   M   T   D   K   A   K   N   G  160

481  ATC AAA GTT AAC TTC AAA ATT AGA CAC AAC ATT GAA GAT GGA AGC GTT  528
161   I   K   V   N   F   K   I   R   H   N   I   E   D   G   S   V  176

529  CAA CTT GCA GAC CAT TAT CAA CAA AAT ACT CCA ATT GGC GAT GGC CCT  576
177   Q   L   A   D   H   Y   Q   Q   N   T   P   I   G   D   G   P  192

577  GTC CTT TTA CCA GAT AAC CAT TAC CTG TCC ACA CAA TCT GCC CTT TCC  624
193   V   L   L   P   D   N   H   Y   L   S   T   Q   S   A   L   S  208

625  AAA GAT CCC AAC GAA AAG AGA GAT CAC ATG ATC CTG CTG GAG TTT GTA  672
209   K   D   P   N   E   K   R   D   H   M   I   L   L   E   F   V  224

673  ACA GCT GCT GCG ATT ACA CAT GGC ATG GAT GAA CTA TAC GAA TAA       717
225   T   A   A   A   I   T   H   G   M   D   E   L   Y   E   *      239
```

FIG. 17

```
  1  ATG AGT AAA GGA GCA GAA CTT TTC ACT GGA ATT GTC CCA ATT CTT ATT   48
  1   M   S   K   G   A   E   L   F   T   G   I   V   P   I   L   I   16

49  GAA TTA AAT GGT GAT GTT AAT GGG CAC AAA TTC TCT GTC AGT GGA GAG   96
 17   E   L   N   G   D   V   N   G   H   K   F   S   V   S   G   E   32

97  GGC GAA GGT GAT GCG ACA TAC GGA AAG TTA ACC CTT AAA TTT ATT TGC  144
 33   G   E   G   D   A   T   Y   G   K   L   T   L   K   F   I   C   48

145  ACT ACA GGA AAA CTA CCT GTT CCA TGG CCA ACA CTT GTC GCT ACT GTC  192
 49   T   T   G   K   L   P   V   P   W   P   T   L   V   A   T   L   64

193  TCT TAT GGT GTT CAA TGC TTT TCA AGA TAT CCA GAT CAT ATG AAA CAG  240
 65   S   Y   G   V   Q   C   F   S   R   Y   P   D   H   M   K   Q   80

241  CAT GAC TTC TTC AAG AGT GCC ATG CCT GAA GGT TAT ATA CAG GAA AGA  288
 81   H   D   F   F   K   S   A   M   P   E   G   Y   I   Q   E   R   96

289  ACT ATA TTT TTC GAA GAT GAC GGG AAC TAC AAG TCG CGT GCT GAA GTC  336
 97   T   I   F   F   E   D   D   G   N   Y   K   S   R   A   E   V  112

337  AAG TTC GAG GGT GAT ACC CTG GTT AGT AGA ATC GAG TTA ACA GGT ACT  384
113   K   F   E   G   D   T   L   V   S   R   I   E   L   T   G   T  128

385  GAT TTT AAA GAA GAT GGA AAC ATC CTT GGA AAT AAA ATG GAA TAC AAC  432
129   D   F   K   E   D   G   N   I   L   G   N   K   M   E   Y   N  144

433  TAT AAC GCA ACT AAT GTA TAC ATC ATG ACA GAC AAA GCA AAA AAT GGA  480
145   Y   N   A   T   N   V   Y   I   M   T   D   K   A   K   N   G  160

481  ATC AAA GTT AAC TTC AAA ATT AGA CAC AAC ATT AAA GAT GGA AGC GTT  528
161   I   K   V   N   F   K   I   R   H   N   I   K   D   G   S   V  176

529  CAA CTT GCA GAC CAT TAT CAA CAA AAT ACT CCA ATT GGC GAT GGC CCT  576
177   Q   L   A   D   H   Y   Q   Q   N   T   P   I   G   D   G   P  192

577  GTC CTT TTA CCA GAT AAC CAT TAC CTG TCC ACA CAA TCT GCC CTT TCC  624
193   V   L   L   P   D   N   H   Y   L   S   T   Q   S   A   L   S  208

625  AAA GAT CCC AAC GAA AAG AGA GAT CAC ATG ATC TAT TTT GAG TTT GTA  672
209   K   D   P   N   E   K   R   D   H   M   I   Y   F   E   F   V  224

673  ACA GCT GCT GCG ATT ACA CAT GGC ATG GAT GAA CTA TAC AAA TAA      717
225   T   A   A   A   I   T   H   G   M   D   E   L   Y   K   *      239
```

FIG. 19

```
  1 ATG AGT AAA GGA GCA GAA CTT TTC ACT GGA ATT GTC CCA ATT CTT ATT    48
  1  M   S   K   G   A   E   L   F   T   G   I   V   P   I   L   I    16

49 GAA TTA AAT GGT GAT GTT AAT GGG CAC AAA TTC TCT GTC AGT GGA GAG    96
 17  E   L   N   G   D   V   N   G   H   K   F   S   V   S   G   E    32

97 GGC GAA GGT GAT GCG ACA TAC GGA AAG TTA ACC CTT AAA TTT ATT TGC   144
 33  G   E   G   D   A   T   Y   G   K   L   T   L   K   F   I   C    48

145 ACT ACA GGA AAA CTA CCT GTT CCA TGG CCA ACA CTT GTC ACT ACT GTC   192
 49  T   T   G   K   L   P   V   P   W   P   T   L   V   T   T   L    64

193 TCT TAT GGT GTT CAA TGC TTT TCA AGA TAT CCA GAT CAT ATG AAA CAG   240
 65  S   Y   G   V   Q   C   F   S   R   Y   P   D   H   M   K   Q    80

241 CAT GAC TTC TTC AAG AGT GCC ATG CCT GAA GGT TAT ATA CAG GAA AGA   288
 81  H   D   F   F   K   S   A   M   P   E   G   Y   I   Q   E   R    96

289 ACT ATA TTT TTC GAA GAT GAC GGG AAC TAC AAG TCG CGT GCT GAA GTC   336
 97  T   I   F   F   E   D   D   G   N   Y   K   S   R   A   E   V   112

337 AAG TTC GAG GGT GAT ACC CTG GTT AAT AGA ATC GAG TTA ACA GGT ACT   384
113  K   F   E   G   D   T   L   V   N   R   I   E   L   T   G   T   128

385 GAT TTT AAA GAA GAT GGA AAC ATC CTT GGA AAT AAA ATG GAA TAC AAC   432
129  D   F   K   E   D   G   N   I   L   G   N   K   M   E   Y   N   144

433 TAT AAC GCA TCT AAT GTA TAC ATC ATG ACA GAC AAA GCA AAA AAT GGA   480
145  Y   N   A   S   N   V   Y   I   M   T   D   K   A   K   N   G   160

481 ATC AAA GTT AAC TTG AAA ATT AGA CAC AAC ATT GAA GAT GGA AGC GTT   528
161  I   K   V   N   L   K   I   R   H   N   I   E   D   G   S   V   176

529 CAA CTT GCA GAC CAT TAT CAA CAA AAT ACT CCA ATT GGC GAT GGC CCT   576
177  Q   L   A   D   H   Y   Q   Q   N   T   P   I   G   D   G   P   192

577 GTC CTT TTA CCA GAT AAC CAT TAC CTG TCC ACA CAA TCT GCC CTT TCC   624
193  V   L   L   P   D   N   H   Y   L   S   T   Q   S   A   L   S   208

625 AAA GAT CCC AAC GAA AAG AGA GAT CAC ATG ATC TAT TTT GAG TTT GTA   672
209  K   D   P   N   E   K   R   D   H   M   I   Y   F   E   F   V   224

673 ACA GCT GCT GCG ATT ACA CAT GGC ATG GAT GAA CTA TAC AAA TAA       717
225  T   A   A   A   I   T   H   G   M   D   E   L   Y   K   *       239
```

FIG. 21

```
  1  ATGAGCAAGGGCGCCGAGCTGTTCACCGGCATCGTGCCCATCCTGATC       48
  1   M  S  K  G  A  E  L  F  T  G  I  V  P  I  L  I       16

49  GAGCTGAATGGCGATGTGAATGGCCACAAGTTCAGCGTGAGCGGCGAG       96
 17   E  L  N  G  D  V  N  G  H  K  F  S  V  S  G  E       32

97  GGCGAGGGCGATGCCACCTACGGCAAGCTGACCCTGAAGTTCATCTGC      144
 33   G  E  G  D  A  T  Y  G  K  L  T  L  K  F  I  C       48

145  ACCACCGGCAAGCTGCCTGTGCCCTGGCCCACCCTGGTGACCACCCTG      192
 49   T  T  G  K  L  P  V  P  W  P  T  L  V  T  T  L       64

193  AGCTACGGCGTGCAGTGCTTCTCACGCTACCCCGATCACATGAAGCAG      240
 65   S  Y  G  V  Q  C  F  S  R  Y  P  D  H  M  K  Q       80

241  CACGACTTCTTCAAGAGCGCCATGCCTGAGGGCTACATCCAGGAGCGC      288
 81   H  D  F  F  K  S  A  M  P  E  G  Y  I  Q  E  R       96

289  ACCATCTTCTTCGAGGATGACGGCAACTACAAGTCGCGCGCCGAGGTG      336
 97   T  I  F  F  E  D  D  G  N  Y  K  S  R  A  E  V      112

337  AAGTTCGAGGGCGATACCCTGGTGAATCGCATCGAGCTGACCGGCACC      384
113   K  F  E  G  D  T  L  V  N  R  I  E  L  T  G  T      128

385  GATTTCAAGGAGGATGGCAACATCCTGGGCAATAAGATGGAGTACAAC      432
129   D  F  K  E  D  G  N  I  L  G  N  K  M  E  Y  N      144

433  TACAACGCCCACAATGTGTACATCATGACCGACAAGGCCAAGAATGGC      480
145   Y  N  A  H  N  V  Y  I  M  T  D  K  A  K  N  G      160

481  ATCAAGGTGAACTTCAAGATCCGCCACAACATCGAGGATGGCAGCGTG      528
161   I  K  V  N  F  K  I  R  H  N  I  E  D  G  S  V      176

529  CAGCTGGCCGACCACTACCAGCAGAATACCCCCATCGGCGATGGCCCT      576
177   Q  L  A  D  H  Y  Q  Q  N  T  P  I  G  D  G  P      192

577  GTGCTGCTGCCCGATAACCACTACCTGTCCACCCAGAGCGCCCTGTCC      624
193   V  L  L  P  D  N  H  Y  L  S  T  Q  S  A  L  S      208

625  AAGGACCCCAACGAGAAGCGCGATCACATGATCTACTTCGGCTTCGTG      672
209   K  D  P  N  E  K  R  D  H  M  I  Y  F  G  F  V      224

673  ACCGCCGCCGCCATCACCCACGGCATGGATGAGCTGTACAAGTGA         717
225   T  A  A  A  I  T  H  G  M  D  E  L  Y  K  *          239
```

FLUORESCENT PROTEIN FROM *AEQUOREA COERULSCENS* AND METHODS FOR USING THE SAME

This application is the National Stage entry of PCT/IB03/00907 filed Jan. 17, 2003 which claims priority to provisional application No. 60/351,518 filed Jan 22, 2002.

FIELD OF THE INVENTION

This invention relates to fluorescent proteins.

BACKGROUND OF THE INVENTION

Labeling is a tool for marking a protein, cell, or organism of interest and plays a prominent role in many biochemical, molecular biological and medical diagnostic applications. A variety of different labels have been developed and used in the art, including radiolabels, chromolabels, fluorescent labels, chemiluminescent labels, and the like, with varying properties and optimal uses. However, there is continued interest in the development of new labels. Of particular interest is the development of new protein labels, including fluorescent protein labels.

RELEVANT LITERATURE

U.S. patents of interest include: U.S. Pat. Nos. 6,066,476; 6,020,192; 5,985,577; 5,976,796; 5,968,750; 5,968,738; 5,958,713; 5,919,445; 5,874,304; and 5,491,084. International Patent Publications of interest include: WO 00/46233; WO 99/49019; and DE 197 18 640 A. Also of interest are: Anderluh et al., *Biochemical and Biophysical Research Communications* (1996) 220:437-442; Dove et al., *Biological Bulletin* (1995) 189:288-297; Fradkov et al., *FEBS* Lett. (2000) 479(3):127-30; Gurskaya et al., *FEBS* Lett., (2001) 507(1):16-20; Gurskaya et al., *BMC Biochem.* (2001) 2:6; Lukyanov, K., et al. (2000) *J. Biol. Chemistry* 275(34):25879-25882; Macek et al., *Eur. J. Biochem.* (1995) 234:329-335; Martynov et al., *J. Biol. Chem.* (2001) 276:21012-6; Matz, M. V., et al. (1999) *Nature Biotechnol.,* 17:969-973; Terskikh et al., *Science* (2000) 290:1585-8; Tsien, *Annual Rev. of Biochemistry* (1998) 67:509-544; Tsien, *Nat. Biotech.* (1999) 17:956-957; Ward et al., *J. Biol. Chem.* (1979) 254:781-788; Wiedermann et al., *Jarhrestagung der Deutschen Gesellschact fur Tropenokologie-qto. Ulm. Feb.* 17-19, 1999. Poster P4.20; Yarbrough et al., *Proceedings of the National Academy of Sciences* (2001) 98:462-7.

SUMMARY OF THE INVENTION

The present invention provides nucleic acid compositions encoding a unique colorless protein from *Aequorea coerulscens* and fluorescent and non-fluorescent mutants thereof, as well as the proteins and peptides encoded by the nucleic acids. The proteins of the present invention are proteins that are colored and/or fluorescent and/or can be photoactivated, where this optical feature arises from the interaction of two or more amino acid residues of the protein. Also of interest are proteins that are substantially similar to, or derivatives or mutants of, the above-referenced specific proteins including fusion proteins incorporating peptides of the present invention, as well as antibodies to these proteins. The subject protein and nucleic acid compositions find use in a variety of different applications. Finally, the present invention provides kits for use in labeling applications.

DESCRIPTION OF THE FIGURES

FIG. 1 is the amino acid sequence and the nucleic acid sequence encoding the wild type GFP-like protein from *Aequorea coerulescens*, herein referred to as acGFP.

FIG. 2 is the comparison of *Aequorea victoria* GFP and *Aequorea coerulescens* acGFP amino acid sequences.

FIG. 3 is the amino acid sequence and the nucleic acid sequence encoding the acGFP mutant, Z1.

FIG. 5 is the amino acid sequence and the nucleic acid sequence the acGFP sequence mutant, Z2.

FIG. 6 is the amino acid sequence and the nucleic acid sequence encoding the acGFP mutant, G1.

FIG. 7 is the amino acid sequence and the nucleic acid encoding the acGFP mutant, G2.

FIG. 9 is the amino acid sequence and the nucleic acid sequence encoding the acGFP mutant, G22.

FIG. 11(*a-c*) show a protein gel-electrophoresis analysis of wildtype acGFP and acGFP mutants.

FIG. 12 is the amino acid sequence and the nucleic acid sequence encoding the acGFP mutant, G22-G222E.

FIG. 15 is the amino acid sequence and the nucleic acid sequence encoding the acGFP mutant, G22-G222E/Y220L.

FIG. 17 is the amino acid sequence and the nucleic acid sequence encoding the acGFP mutant, 220-II-5.

FIG. 19 is the amino acid sequence and the nucleic acid sequence encoding the acGFP mutant, CFP-rand3.

FIG. 21 is the amino acid sequence and the nucleic acid sequence encoding acGFP mutant, CFP-3.

FIG. 23 is the amino acid and nucleic acid sequences for a humanized version of mutant G22.

DESCRIPTION OF THE INVENTION

Figure 4:
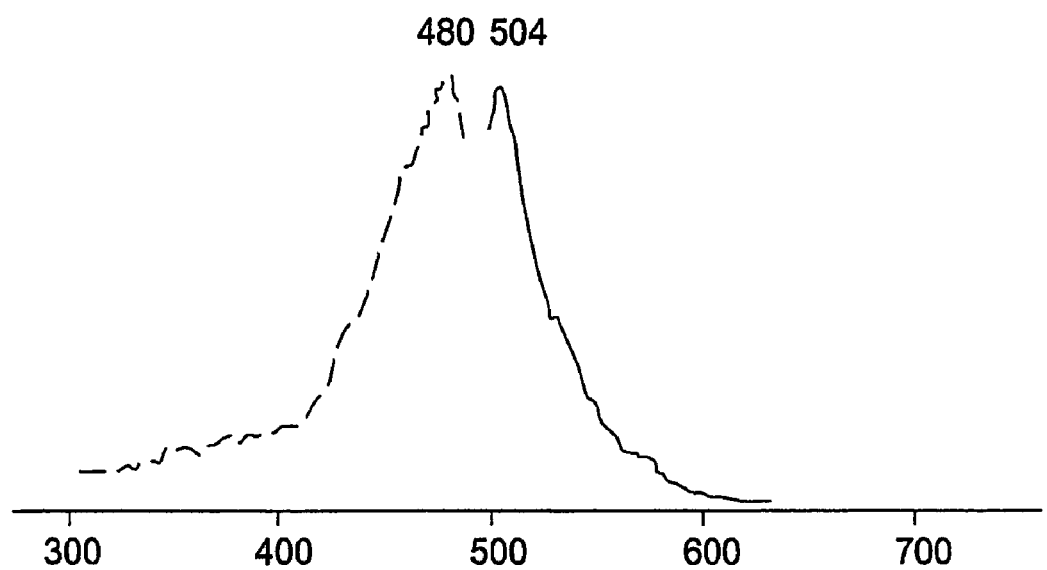
FIG. 4 is the excitation-emission spectra for mutant Z1.

The subject invention provides a nucleic acid, wherein the nucleic acid encodes a fluorescent protein, acGFP, or a mutant or derivative thereof. In certain embodiments, the nucleic acid is isolated, or has been engineered or is present in an environment other than its natural environment. In certain embodiments, the nucleic acid has a sequence of residues that is substantially the same as, or identical to, a nucleotide sequence of at least 10 residues in length from SEQ ID NO: 01, 03, 05, 07, 09, 11, 13, 15, 17, 19, 21, or 23.

In certain embodiments, the nucleic acid of the present invention has a sequence similarity of at least about 60% with a sequence of SEQ ID NO: 01, 03, 05, 07, 09, 11, 13, 15, 17, 19, 21, or 23, and is at least 10 residues in length. In certain embodiments, the nucleic acid of the present invention encodes a protein that has an amino acid sequence selected from the group consisting of SEQ ID NO: 02, 04, 06, 08, 10, 12, 14, 16, 18, 20, 22, or 24, encoding a mutant or derivative protein of a *Aequorea coerulscens* fluorescent protein.

Also provided are fragments of the nucleic acids of the present invention. Additionally, nucleic acids or mimetics thereof that hybridize under stringent conditions to the nucleic acids of the present invention are provided. Also provided are constructs comprising a vector and a nucleic acid of the present invention. In addition, the present invention provides expression cassettes that include: a transcriptional initiation region functional in a expression host, a nucleic acid of the present invention, and a transcriptional termination region functional in the expression cassette as part of an extrachromosomal element or integrated into the genome of the cell as a result of introduction of said expression cassette into the cell.

Also provided are methods of producing a chromogenic and/or fluorescent protein including growing a cell of the present invention, expressing the protein in the cell, and isolating the protein substantially free of other proteins.

In addition, proteins or fragments or peptides encoded by a nucleic acid of the present invention are provided, as are antibodies that bind specifically to the proteins or peptides of the present invention.

Additionally, transgenic cells (or their progeny) that include a nucleic acid of the present invention are provided, as are transgenic organisms that include a nucleic acid of the present invention.

Also provided are methods that employ a chromo- or fluorescent protein of the present invention, or that employ a nucleic acid encoding a chromogenic or fluorescent protein of the present invention.

Additionally, kits that include a nucleic acid or protein according to the subject invention and instructions of use therefor, are provided.

In accordance with the present invention there may be employed conventional molecular biology, microbiology, and recombinant DNA techniques within the sill of the art. Such techniques are explained fully in the literature. See, e.g., Maniatis, Fritsch & Sambrook, *Molecular Cloning: A Laboratory Manual* (1982); *DNA Cloning: A Practical Approach. Volumes I and II* (D. N. Glover, ed. 1985); *Oligonucleotide Synthesis* (M. J. Gait, ed. 1984); *Nucleic Acid Hybridization* (B. D. Hames & S. J. Higgins, eds. (1984)); *Animal Cell Culture* (R. I. Freshney, ed. (1986)); *Immobilized Cells and Enzymes* (IRL Press (1986)); and B. Perbal, *A Practical Guide to Molecular Cloning* (1984).

A "vector" is a replicon, such as plasmid, phage or cosmid, to which another DNA segment may be attached.

A "DNA molecule" refers to the polymeric form of deoxyribonucleotides (adenine, guanine, thymine, or cytosine) in either single-stranded form or a double-stranded helix. This term refers only to the primary and secondary structure of the molecule, and does not limit it to any particular tertiary forms. Thus, "DNA molecule" includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl)terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' of the coding sequence.

As used herein, the term "hybridization" refers to the process of association of two nucleic acid strands to form an antiparallel duplex stabilized by means of hydrogen bonding between residues of the opposite nucleic acid strands.

The term "oligonucleotide" refers to a short (under 100 bases in length) nucleic acid molecule.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a coding sequence. For example, the promoter sequence may be bounded at its 3' terminus by the transcription initiation site and extend upstream (5' direction) to include the minimum number of bases or elements necessary to initiate transcription at levels detectable above background. Within the promoter sequence may be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a host cell chromosome or is maintained extra-chromosomally so that the transforming DNA inherited by daughter cells during cell replication. Such a stably transformed eukaryotic cell is able to establish cell lines or clones comprised of a population of daughter cells containing the transforming DNA. A "clone" is a population of cells derived from a single cell or common ancestor by mitosis. A "cell line" is a clone or a cell that is capable of stable growth in vitro for many generations.

A "heterologous" region of a DNA construct is an identifiable segment of DNA within a larger DNA molecule that is not found in association with the larger molecule in nature; for example, when the heterologous region encodes a mammalian genomic DNA in the genome of a non-mammlian organism. In another example, heterologous DNA includes coding sequences in a construct where portions of genes from two different sources have been brought together so as to produce a fusion protein product.

As used herein, the term "reporter gene" refers to a coding sequence attached to heterologous promoter or enhancer elements and whose product may be assayed easily and quantifiably when the construct is introduced into tissues or cells.

The amino acids described herein are preferred to be in the "L" isomeric form. The amino acid sequences are given in one-letter code (A: alanine; C; cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T:

threonine; V: valine; W: tryptophan; Y: tyrosine; X: any residue). $NH_2$ refers to the free amino group present at the amino terminus of a polypeptide. COOH refers to the free carboxy group present at the carboxy terminus of a polypeptide. Standard polypeptide nomenclature, see *J. Biol. Chem.*, 243, 3552-59 (1969), is used.

The term "immunologically active" defines the capability of the natural, recombinant or synthetic chromogenic or fluorescent protein, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal. The term "specific binding," in the context of antibody binding to an antigen, is a term well understood in the art and refers to binding of an antibody to the antigen to which the antibody was raised, but not other, unrelated antigens.

As used herein the term "isolated" is meant to describe a polynucleotide, a polypeptide, an antibody, or a host cell that is an environment different from that in which the polynucleotide, the polypeptide, and antibody, or the host cell naturally occurs.

Bioluminescence is emission of light by living organisms that is visible in the dark. (See, e.g., Harvey, *Bioluminescence*, New York: Academic Press (1952); Hastings, "Bioluminescence" in: *Cell Physiology* (ed. by Speralakis), New York Academic Press pp. 651-81 (1995); Wilson and Hastings, "Bioluminescence", Annu. *Rev. Cell. Dev. Biol.* 14, pp. 197-230 (1998)). Bioluninescence does not include so-called ultra-weak light emission, that can be detected in virtually all living structures using sensitive luminometric equipment (Murphy and Sies, "Visible-range low-level chemiluminescence in biological systems", *Meth. Enzymol.* 186, pp. 595-610 (1990); Radotic, et al., "Spontaneous ultra-weak bioluminescence in plants: origin, mechanisms and properties", *Gen. Physiol. Biophys.* 17, pp. 289-308 (1998)), nor does bioluminescence emanate from weak light emission which most probably does not play an ecological role, such as the glowing of a bamboo growth cone (Totsune, et al., "Cemiluminescence from bamboo shoot cut", *Biochem. Biophys. Res. Comm.* 194, pp. 1025-1029 (1993)), or emission of light during the fertilization of animal eggs (Klebanoff, et al., "Metabolic similarities between fertilization and phagocytosis", *J. Exp. Med.* 149, pp. 938-53 (1979); Schomer and Epel, "Redox changes during fertilization and maturation of marine invertebrate eggs", *Dev. Biol.* 2003, pp. 1-11 (1998)).

As used herein, the term "GFP-like proteins" is meant to describe proteins similar to the green fluorescent protein (GFP) from *Aequorea victoria*.

Nucleic acid compositions encoding a colorless GFP-like protein, acGFP, from *Aequorea coerulscens*, and fluorescent and non-fluorescent derivatives or mutants thereof, as well as proteins and peptides encoded by these nucleic acid composites are provided. The proteins of interest are proteins that are colored and/or fluorescent and/or can be photoactivated, where the color, fluorescent, or photoactivation feature arises from the interaction of two or more amino acid residues of the protein. Also of interest are proteins that are substantially similar to, or derivatives or mutants of, the above-referenced specific proteins. Also provided are fragments of the nucleic acids and the peptides encoded thereby, as well as antibodies to the subject proteins and peptides. In addition, transgenic cells and organisms are provided. The subject protein and nucleic acid compositions find use in a variety of different applications and methods, particularly protein labeling applications. Finally, kits for use in such methods and applications are provided.

Before the subject invention is described further, it is to be understood that the invention is not limited to the particular embodiments of the invention described below, as variations of the particular embodiments may be made and still fall within the scope of the invention. It is also to be understood that the terminology employed is for the purposed of describing particular embodiments, and is not intended to be limiting.

In this specification, the singular forms "a", "an" and "the" include plural references unless the context clearly dictates otherwise. Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described. All publications mentioned herein are incorporated herein by reference for the purpose of describing and disclosing the invention.

In describing the present invention, nucleic acid compositions will be described first, followed by a discussion of protein compositions, antibody compositions and transgenic cells and organisms. Next a review of exemplary methods in which the proteins of the present invention find use is provided.

Nucleic Acid Compositions

As summarized above, the present invention provides nucleic acid compositions encoding a colorless protein, acGFP, from *Aequorea coerulescens*, or fluorescent and non-fluorescent mutants or derivatives of acGFP, as well as fragments and homologs of the nucleic acid compositions. The phrase "fluorescent protein" means a protein that is fluorescent; e.g., it may exhibit low, medium or intense fluorescence upon irradiation with light of the appropriate excitation wavelength. The proteins of the present invention are those in which the fluorescent characteristic is one that arises from the interaction of two or more amino acid residues of the protein, and not from a single amino acid residue. As such, the fluorescent proteins of the present invention do not include proteins that exhibit fluorescence only from residues that act by themselves as intrinsic fluors, i.e., tryptophan, tyrosine and phenylalanine. The fluorescent proteins of the subject invention thus are fluorescent proteins whose fluorescence arises from some structure in the protein other than the above-specified single amino acid resides; e.g., it arises from an interaction of two or more amino acid residues.

One nucleic acid composition of the present invention is a composition comprising a sequence of DNA having an open reading frame that encodes a polypeptide of the subject invention; i.e., a fluoroprotein gene. Such a nucleic acid composition is capable, under appropriate conditions, of being expressed as a fluoroprotein. Also encompassed in the term nucleic acid composition are nucleic acids that are homologous to, substantially similar to, identical to, or mimetics of the nucleic acids of the present invention. The subject nucleic acids are present in an environment other than their natural environment; e.g., they are isolated, present in enriched amounts, or are present or expressed in vitro or in a cell or organism other than their naturally occurring environment.

In another embodiment of the present invention, the nucleic acids may be encoded by SEQ ID NO: 01, 03, 05, 07, 09, 11, 13, 15, 17, 19, 21 or 23, or are nucleic acids derived from, or are homologs of such nucleic acids.

In addition to the above-described specific nucleic acid compositions, also of interest are homologs of the above sequences. With respect to homologs of the subject nucleic acids, the source of homologous genes may be any species of plant or animal or the sequence may be wholly or partially synthetic including sequences incorporating nucleic acid mimetics. In certain embodiments, sequence similarity between homologs is at least about 40%, and maybe 50%, 60%, 70% or higher, including 75%, 80%, 85%, 90% and 95% or higher. Sequence similarity is calculated based on a reference sequence, which may be a subset of a larger sequence, such as a conserved motif, coding region, flanking region, etc. A reference sequence will usually be at least about 18 nucleotides long, more usually at least about 30 nucleotides long, and may extend to the complete sequence that is being compared. Algorithms for sequence analysis are known in the art, such as BLAST, described in Altschul et al., *J. Mol. Biol.*, 215, pp. 403-10 (1990) (for example, using default settings, i.e., parameters w=4 and T=17).

Homologs are identified by any of a number of methods. A fragment of a cDNA of the present invention may be used as a hybridization probe against a cDNA library from a target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0I.15 M sodium chloride/0.015 M sodium citrate). Sequence identity may be determined by hybridization under stringent conditions, for example, at 50° C. or higher and 0.1×SSC (15 mM sodium chloride/1.5 mM sodium citrate). Nucleic acids having a region of substantial identity to the provided sequences, e.g., allelic variants, genetically-altered versions of the gene, etc., bind to the provided sequences under stringent hybridization conditions. By using probes, particularly labeled probes of DNA sequences, one can isolate homologous or related genes.

Or particular interest in certain embodiments of the present invention are nucleic acids of substantially the same length as the nucleic acids identified as SEQ ID NO: 01, 03, 05, 07, 09, 11, 13, 15, 17, 19, 21, or 23, where "substantially the same length" means that any difference in length does not exceed about 20%, usually does not exceed about 10% and more usually does not exceed about 5%. In preferred embodiments nucleotides of substantially the same length will have a sequence identity to SEQ ID NO: 01, 03, 05, 07, 09, 11, 13, 15, 17, 19, 21 or 23, of at least about 90% (e.g., at least about 92%, 93%, 94%), usually at least about 95%, 96%, 97% or 98% or even about 99% over the entire length of the nucleic acid. "Substantially similar" means that sequence identity will generally be at least about 60%, usually at least about 75% and often at least about 80, 85, 90 (e.g., 92%, 93%, 94%), or even 95%, e.g., 96%, 98%, 98%, 99%, 99.5% or higher.

In addition, the present invention includes nucleic acids that encode the proteins encoded by the previously-described nucleic acids, but differ in sequence from the previously-described nucleic acids due to the degeneracy of the genetic code.

Also provided are nucleic acids that hybridize to the above-described nucleic acids under stringent conditions (i.e., complements of the previously-described nucleic acids). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution of 50% formamide, 5×SSC (150 mM NaCl, 15 mM trisodium citrate), 50 mM sodium phosphate (pH7.6), 5× Denhardt's solution, 10% destran sulfate, and 20 µg/ml denatured, sheared salmon sperm DNA, followed by washing in 0.1×SSC at about 65° C. Stringent hybridization conditions are hybridization conditions that are at least 80% as stringent as the above-representative conditions. Other stringent hybridization conditions are known in the art and may also be employed to identify nucleic acids of this particular embodiment of the invention.

Nucleic acids encoding mutants or derivatives of the proteins of the invention also are provided. Mutant nucleic acids can be generated by random mutagenesis or targeted mutagenesis, using techniques well known in the art. Mutations of interest include deletions, additions and substitutions. In some embodiments, fluorescent proteins encoded by nucleic acids encoding homologs or mutants have the same fluorescent properties as the wild type fluorescent protein. In other embodiments, homolog or mutant nucleic acids encode fluorescent proteins with altered spectral properties, as described in more detail for mutant acGFP proteins herein.

Nucleic acids of the subject invention may be cDNA or genomic DNA or a fragment thereof. In certain embodiments, the nucleic acids of the subject invention include one or more of the open reading frames encoding specific fluorescent proteins and polypeptides, and introns, as well as adjacent 5' and 3' non-coding nucleotide sequences involved in the regulation of expression, including sequences up to about 20 kb beyond the coding region, but possibly further, in either direction. The subject nucleic acids may be introduced into an appropriate vector for extrachromosomal maintenance or for integration into a host genome, as described in greater detail below.

The term "cDNA" as used herein is intended to include nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest may comprise the nucleic acid present between the initiation codon and the stop codon, as defined in the listed sequences, including all of the introns that are normally present in a native chromosome. The genomic sequence of interest further may include 5' an 3' un-translated regions found in the mature mRNA, as well as specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kb or smaller; and substantially free of flanking chromosomal sequence. Genomic DNA flanking the coding region, either 3' or 5', or internal regulatory sequences as sometimes found in introns, may contain sequences required for proper tissue- and stage-specific expression.

The nucleic acid compositions of the subject invention may encode all or a part of the subject proteins. Double- or single-stranded fragments may be obtained from the DNA sequence by chemically synthesizing oligonucleotides in accordance with conventional methods, by restriction enzyme digestion, by PCR amplification, etc. For the most part, DNA fragments will be at least about 15 nucleotides in length, usually at least about 18 nucleotides in length or about 25 nucleotides in length, and may be at least about 50 nucleotides in length. In some embodiments, the subject nucleotide acid molecules may be about 100, about 200, about 300, about 400, about 500, about 600, about 700 nucleotides or greater in length. The subject nucleic acids may encode fragments of the subject proteins or the full-length proteins; e.g., the subject nucleic acids may encode polypeptides of about 25 amino acids, about 50, about 75, about 100, about 125, about 150, about 200 amino acids up to the full length protein.

The subject nucleic acids may be isolated and obtained in substantial purity, generally as other than as an intact chromosome. Usually, the DNA will be obtained substantially free of nucleic acid sequences that do not include a nucleic acid of the subject invention or a fragment thereof. Substantial purity means that the nucleic acids are at least about 50% pure, usually at least about 90% pure and are typically "recombinant", i.e., flanked by one ore more nucleotides with which it is not normally associated on a naturally-occurring chromosome in its natural host organism.

The polynucleotides of the present invention, e.g., polynucleotides having the sequence of SEQ ID NO: 01, 03, 05, 07, 09, 11, 13, 15, 17, 19, 21 or 23, the corresponding cDNAs, full-length genes and constructs can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual*, 2$^{nd}$ Ed., Cold Spring Harbor Press, Cold Spring Harbor, N.Y. (1989), and under regulations described in, e.g., United States Dept. of HHS, *National Institute of Health (NIH) Guidelines for Recombinant DNA Research*.

Also provided are nucleic acids that encode fusion proteins of the subject protein or peptides of the present invention, or fragments thereof, fused to a second peptide or protein. The second protein may be, for example, a degradation sequence, a signal peptide, or any protein of interest. Fusion proteins may comprise for example, an acGFP or mutant acGFP polypeptide and a second polypeptide ("the fusion partner") fused in-frame at the N-terminus and/or C-terminus of the acGFP polypeptide. Fusion partners include, but are not limited to, polypeptides that can bind antibodies specific to the fusion partner (e.g., epitope tags), antibodies or binding fragments thereof, polypeptides that provide a catalytic function or induce a cellular response, ligands or receptors or mimetics thereof, and the like. In such fusion proteins, the fusion partner is generally not naturally associated with the acGFP portion of the fusion protein, and is typically not an *Aequorea coerulescens* protein or derivative/fragment thereof; i.e., it is not found in *Aequorea* species.

Also provided are vector and other nucleic acid constructs comprising the subject nucleic acids, where such constructs may be used for a number of applications, including propagation, protein production, etc. Viral and non-viral vectors may be prepared and used, including plasmids. The choice of vector will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal. The choice of appropriate vector is well within the skill of the art, and many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo, typically by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the subject chromogenic or fluorescent proteins or fusion proteins thereof. For expression, the gene product encoded by a polynucleotide of the invention is expressed in any convenient expression system, including, for example, bacterial, yeast, insect, amphibian and mammalian systems. Such vectors and host cells are described in U.S. Pat. No. 5,654,173. In the expression vector, a subject polynucleotide—e.g., as set forth in SEQ ID NO: 01, 03, 05, 07, 09, 11, 13, 15, 17, 19, 21 or 23—is linked to a regulatory sequence as appropriate to obtain the desired expression properties. These regulatory sequences can include promoters (attached either at the 5' end of the sense strand or at the 3' end of the antisense strand), enhancers, terminators, operators, repressors and inducers. The promoters can be regulated or constitutive. In some situations it may be desirable to use conditionally active promoters, such as tissue-specific or developmental stage-specific promoters. These are linked to the desired nucleotide sequences using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject species from which the subject nucleic acid is obtained, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described above.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded, then used for expression.

The above-described expression systems may be employed with prokaryotes or eukaryotes in accordance with conventional methods, depending upon the purpose for expression. For large-scale production of the protein, a unicellular organism, such as *E. coli, B. subtilis, S. cerevisiae*, insect cells in combination with baculovirus vectors, or cells of a higher organism such as vertebrates, e.g., COS 7 cells, HEK 293, CHO, *Xenopus oocytes*, etc., may be used as the expression host cells. In some situations, it is desirable to express the gene in eukaryotic cells, where the expressed protein will benefit from native folding and post-transitional modifications. Small peptides also can be synthesized in the laboratory. Polypeptides that are subsets of the complete protein sequence may be used to identify and investigate parts of the protein important for function.

Specific expression systems of interest include bacterial-, yeast-, insect cell- and mammalian cell-derived expression systems. References drawn to representative systems from each of these categories are provided below.

Expression systems in bacteria include those described in Chang et al., *Nature* 275:615 (1978); Goeddel et al., *Nature* 281:544 (1979); Goeddel et al., *Nucleic Acids Res.* 8:4057 (1980); EP 0 036,776; U.S. Pat. No. 4,551,433; DeBoer et al., *Proc. Natl. Acad. Sci.* (USA) 80:21-25 (1983); and Siebenlist et al., *Cell* 20:269 (1980).

Expression systems in yeast include those described in Hinnen et al., *Proc. Natl. Acad. Sci.* (USA) 75:1929 (1978); Ito et al., *J. Bacteriol.* 153:163 (1983); Kurtz et al., *Mol. Cell Biol.* 6:142 (1986); Kunze et al., *J. Basic Microbiol.* 25:141 (1985); Gleeson et al., *J. Gen. Microbiol.* 132:3459 (1986); Roggenkamp et al., *Mol. Gen. Genet.* 202:302; (1986); Das et al., *J. Bacteriol.* 158:1165 (1984); De Louvencourt et al., *J. Bacteriol.* 154:737 (1983); Van den Berg et al., *Bio/Technology* 8:135 (1990); Kunze et al., *J. Basic Microbiol.* 25:141 (1985); Cregg et al., *Mol. Cell. Biol.* 5:3376 (1985); U.S. Pat. Nos. 4,837,148 and 4,929,555; Beach and Nurse, *Nature* 300:706 (1981); Davidow et al., *Curr. Genet.* 10:380 (1985); Gaillardin et al., *Curr. Genet.* 10:49 (1985); Ballance et al., *Biochem. Biophys. Res. Commun.* 112:284-289 (1983); Tilburn et al., *Gene* 26:205-221 (1983); Yelton et al., *Proc. Natl. Acad. Sci.* (81:1470-1474 (1984); Kelly and Hynes, *EMBO J.* 4:475479 (1985); EP 0 244, 234: and WO 91/00357.

Expression of heterologous genes in insects is accomplished as described in U.S. Pat. No. 4,745,051; Friesen et al., "The Regulation of Baculovirus Gene Expression", in: *The Molecular Biology of Baculoviruses* (W. Doerfler, ed.) (1986); EP 0 127,839; EP 0 155,476; and Vlak et al., *J. Gen. Virol.* 69:765-776 (1988); Miller et al., *Ann. Rev. Microbiol.* 42:177 (1988); Carbonell et al., *Gene* 73:409 (1988); Maeda et al., *Nature* 315:592-594 (1985); Labacq-Verheyden et al., *Mol. Cell. Biol.* 8:3129 (1988); Smith et al., *Proc. Natl. Acad. Sci.* 82:8844 (1985); Miyajima et al., *Gene* 58:273 (1987); and Martin et al., *DNA* 7:99 (1988). Numerous baculoviral strains and variants and corresponding permissive insect host cells from hosts are described in Luckow et al., *Bio/Technology* 6:47-55 (1988); Miller et al., *Genetic Engineering* 8:277-279 (1986); and Maeda et al., *Nature* 315:592-594 (1985).

Mammalian expression is accomplished as described in Dijkema et al., *EMBO J.* 4:761 (1985), Gorman et al., *Proc. Natl. Acad. Sci.* (USA) 79:6777 (1982); Boshart et al., *Cell* 41:521 (1985); and U.S. Pat. No. 4,399,216. Other features of mammalian expression are facilitated as described in Hamm and Wallace, *Meth. Enz.* 58:44 (1979); Barnes and Sata, *Anal. Biochem.* 102:255 (1980); U.S. Pat. Nos. 4,767,704; 4,657,866; 4,927,762; 4,560,655; WO 90/103430; WO 87/00195, and U.S. RE 30,985.

When any of the above-referenced host cells, or other appropriate host cells or organisms are used to replicate and/or express the polynucleotides or nucleic acids of the invention, the resulting replicated nucleic acid, RNA, expressed protein or polypeptide is within the scope of the invention as a product of the host cell or organism. The product may be recovered by an appropriate means known in the art.

Once the gene corresponding to a selected polynucleotide is identified, its expression can be regulated in the cell to which the gene is native. For example, an endogenous gene of a cell can be regulated by an exogenous regulatory sequence inserted into the genome of the cell at location sufficient to at least enhance expression of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which also is herein incorporated by reference. As such, also encompassed in the present invention is the production of proteins without manipulation of the encoding nucleic acid itself, but instead through integration of a regulatory sequence into the genome of cell that already includes a gene encoding the desired protein.

Also of interest are promoter sequences of the genomic sequences of the present invention, where the sequence of the 5' flanking region may be utilized for promoter elements, including enhancer binding sites, that, for example, provide for regulation of expression in cells/tissues where the subject proteins gene are expressed.

Also provided are small DNA fragments of the subject nucleic acids, that are useful as primers for PCR, hybridization screening probes, etc. Larger DNA fragments are useful for production of the encoded polypeptide, as described previously. However, for use in geometric amplification reactions, such as geometric PCR, a pair of small DNA fragments, i.e., primers, will be used. The exact composition of the primer sequences is not critical to the invention, but for most applications, the primers will hybridize to the subject sequence under stringent conditions, as is known in the art. It is preferable to choose a pair of primers that will generate an amplification product of at least about 50 nucleotides, preferably at least about 100 nucleotides. Algorithms for the selection of primer sequences are generally known, and are available in commercial software packages. Amplification primers hybridize to complementary strands of DNA and will prime toward each other.

The nucleic acid compositions of the present invention also may be used to identify expression of a gene in a biological specimen. The manner in which one probes cells for the presence of particular nucleotide sequences, such as genomic DNA or RNA, is well established in the art. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g., nitrocellulose, nylon, etc., and then probed with a fragment of the subject DNA as a probe. Other techniques, such as oligonucleotide ligation assays, in situ hybridizations, and hybridization to DNA probes arrayed on a solid chip may also be used. Detection of mRNA hybridizing to the subject sequence is indicative of gene expression in the sample.

The subject nucleic acids, including flanking promoter regions and coding regions, may be mutated in various ways known in the art to generate targeted changes in promoter strength or to vary the sequence of the encoded protein or properties of the encoded protein, including the fluorescent properties of the encoded protein. The DNA sequence or protein product of such a mutation will be substantially similar to SEQ ID NOS. 1-24 provided herein. The sequence changes of these sequences may be substitutions, insertions, deletions, or a combination thereof. Deletions may further include large changes, such as deletions of a domain or exon, e.g., of stretches of 10, 20, 50, 75, 100, 150 or more amino acid residues. Techniques for in vitro mutagenesis may be found in Gustin et al., *Biotechniques* 14;22 (1993); Barany, *Gene* 37:111-23 (1985); and Colicelli et al., *Mol. Gen. Genet.* 199:537-9 (1985). Methods for site-specific mutagenesis can be found in Sambrook et al., *Molecular Cloning: A Laboratory Manual*, CSH Press, pp. 15.3-15.108 (1989). Such mutated nucleic acid derivatives may be used to study structure-function relationships of a particular chromogenic fluorescent protein, or to alter properties of the protein that affect its function or regulation.

Also of interest are humanized versions of the subject nucleic acids such as the hG22 mutant of acGFP described herein. As used herein, the term "humanized" refers to changes made to the nucleic acid sequence to optimize the codons for expression of the protein in human cells (Yang et al., *Nucleic Acids Research* 24:4592-93 (1996)). See also U.S. Pat. No. 5,795,737 which describes humanization of proteins, the disclosure of which is herein incorporated by reference.

Peptide Compositions

The subject invention provides fluorescent protein acGFP and derivatives thereof, as well as related polypeptide fragments. As used herein, the term fluorescent protein refers to any protein that fluoresces when irradiated with light, e.g., white light or light of a specific wavelength (or a narrow band of wavelengths such as an excitation wavelength). The term polypeptide as used herein refers to both full-length proteins, as well as portions or fragments of proteins. Also included in this term are variations of a naturally occurring protein, where such variations are homologous or substantially similar to the naturally occurring protein, and mutants of the naturally occurring proteins, as described in greater detail below. The subject polypeptides are present in environments other than their natural environment.

In many embodiments, the subject proteins have an absorbance maximum ranging from about 300 nm to 700 nm, usually from about 350 nm to 550 nm and more usually from about 400 to 500 nm, and often from about 450 to 490 nm, e.g., 470 to 490 nm while the emission spectra of the subject proteins typically ranges from about 400 nm to 700 nm, usually from about 450 nm to 650 nm and more usually from about 500 to 600 nm while in many embodiments the emission spectra ranges from about 500 to 550 nm, e.g., 500 to 525 nm, or 500 to 510 nm. The subject proteins generally have a maximum extinction coefficient that ranges from about 25,000 to 150,000 and usually from about 45,000 to 120,000, e.g., 50,000 to 100,000. The subject proteins typically range in length from about 150 to 300 amino acids and usually from about 200 to 300 amino acid residues, and generally have a molecular weight ranging from about 15 to 35 kDa, usually from about 17.5 to 32.5 kDa.

In certain embodiments, the subject proteins are bright, where "bright" is meant that the chromoproteins and their fluorescent derivatives can be detected by common methods (e.g., visual screening, spectrophotometry, spectrofluorometry, fluorescent microscopy, by FACS instrumentation, etc.). Fluorescence brightness of a particular fluorescent protein is determined by its quantum yield multiplied by maximal extinction coefficient. Brightness of a chromoprotein may be expressed by its maximal extinction coefficient.

In certain embodiments, the subject proteins fold rapidly following expression in the host cell. "Rapidly folding" means that the proteins achieve the tertiary structure that gives rise to their chromogenic or fluorescent quality in a short period of time. In these embodiments, the proteins fold in a period of time that generally does not exceed about 3 days, usually does not exceed about 2 days and more usually does not exceed about 1 day.

Specific proteins of interest include the wild type acGFP fluorescent protein and mutants thereof, as provided, for example, in SEQ ID NO: 02, 04, 06, 08, 10, 12, 14, 16, 18, 20, 22, or 24 coding for acGFP, Z1, Z2, G1, G2, G22, G22-G22E, G22-G22E/Y220L, 220-11-5, CFP-rand3 and CFP-3 and humanized G22.

Homologs of proteins (or fragments thereof) that vary in sequence from the above-provided specific amino acid sequences, i.e., SEQ ID NO: 02, 04, 06, 08, 10, 12, 14, 16, 18, 20, 22, or 24, are also provided. "Homolog" means a protein having at least about 35%, usually at least about 40% and more usually at least about 60% amino acid sequence identity to amino acid sequences SEQ ID NO: 02, 04, 06, 08, 10, 12, 14, 16, 18, 20, 22, or 24, as determined using MegAlign, DNAstar clustal algorithm as described in D. G. Higgins and P. M. Sharp, "Fast and Sensitive multiple Sequence Alignments on a Microcomputer," *CABIOS,* 5 pp. 151-3 (1989) (using parameters ktuple 1, gap penalty 3, window 5 and diagonals saved 5). In many embodiments, homologs of interest have much higher sequence identity e.g., 65%, 70%, 75%, 80%, 85%, 90% (e.g., 92%, 93%, 94%) or higher, e.g., 95%, 96%, 97%, 98%, 99%, 99.5%, particularly for the sequence of the amino acids that provide the functional regions of the protein.

Also provided are proteins that are substantially identical to the wild type protein, where "substantially identical" means that the protein has an amino acid sequence identity to the sequence of wild type protein of at least about 60%, usually at least about 65%, and more usually at least about 70%, and in some instances the identity may be much higher, e.g., 75%, 80%, 85%, 90% (e.g., 92%, 93%, 94%), 95% or higher, e.g., 95%, 96%, 97%, 98%, 99%, 99.5%.

Proteins that are derivatives or mutants of the above-described naturally occurring proteins are also provided. Mutants may retain biological properties of the wild type (e.g., naturally occurring) proteins, or may have biological properties which differ from the wild type proteins. The term "biological property" of the proteins of the present invention refers to, but is not limited to, spectral properties, such as absorbance maximum, emission maximum, maximum extinction coefficient, brightness (e.g., as compared to the wild type protein or another reference protein such as green fluorescent protein (GFP) from *A. Victoria*), and the like; in vivo and/or in vitro stability (e.g., half-life); and other such properties. Mutations include single amino acid changes, deletions of one or more amino acids, N-terminal truncations, C-terminal truncations, insertions, and the like.

Mutant proteins can be generated using standard techniques of molecular biology, e.g., random mutagenesis, and targeted mutagenesis as described earlier. Several mutants are described herein. Given the guidance provided in the Example, and using standard techniques, those skilled in the art can readily generate a wide variety of additional mutants and test whether a biological property has been altered. For example, fluorescence intensity can be measured using a spectrophotometer at various excitation wavelengths.

Those proteins of the subject invention that are naturally-occurring proteins are present in a non-naturally occurring environment, e.g., are separated from their naturally-occurring environment. In certain embodiments, the subject proteins are present in a composition that is enriched for the subject protein as compared to its naturally-occurring environment. For example, purified protein is provided, where "purified" means that the protein is present in a composition that is substantially free of non-chromogenic or fluorescent proteins of interest, where "substantially free" means that less than 90%, usually less than 60% and more usually less than 50% of the composition is made up of non-chromogenic or fluorescent proteins or mutants thereof. The proteins of the present invention also may be present as an isolate, by which is meant that the protein is substantially free of other proteins and other naturally-occurring biological molecules, such as oligosaccharides, polynucleotides and fragments thereof, and the like, where the term "substantially free" in this instance means that less than 70%, usually less than 60% and more usually less than 50% of the composition containing the isolated protein is some other natural occurring biological molecule. In certain embodiments, the proteins are present in substantially pure form, where by "substantially pure form" means at least 95%, usually at least 97% and more usually at least 99% pure.

In addition to the naturally-occurring proteins, polypeptides that vary from the naturally occurring proteins, e.g., the mutant proteins described above, are also provided. Generally such polypeptides include an amino acid sequence encoded by an open reading frame (ORF) of the gene encoding the subject wild type protein, including the full length protein and fragments thereof, particularly biologically active fragments and/or fragments corresponding to functional domains, and the like; including fusions of the subject polypeptides to other proteins or peptides. Fragments of interest will typically be at least about 10 amino acids in length, usually at least about 50 amino acids in length, and may be as long as 300 amino acids in length or longer, but will usually not exceed about 250 amino acids in length, where the fragment will have a stretch of amino acids that is identical to the subject protein of at least about 10 amino acids, and usually at least about 15 amino acids, and in many embodiments at least about 50 amino acids in length. In some embodiments, the subject polypeptides are about 25 amino acids, about 50, about 75, about 100, about 125, about 150, about 200, or about 250 amino acids in length, up to the entire length of the protein. In some embodiments, a protein fragment retains all or substantially all of the specific property of the wild type protein.

The subject proteins and polypeptides may be obtained from naturally-occurring sources or synthetically produced. For example, wild type proteins may be derived from biological sources which express the proteins, e.g., *Aequorea coerulescens* the subject proteins may also be derived from synthetic means, for example, by expressing a recombinant gene or nucleic acid coding sequence encoding the protein of interest in a suitable host, as described above. Any convenient protein purification procedures may be employed, where suitable protein purification methodologies are described in *Guide to Protein Purification,* (Deuthser ed.) (Academic Press, 1990). For example, a lysate may be prepared from the original source and purified using HPLC, exclusion chromatography, gel electrophoresis, affinity chromatography, and the like.

Antibody Compositions

Also provided are antibodies that bind specifically to the fluorescent proteins of the present invention. Suitable antibodies are obtained by immunizing a host animal with peptides comprising all or a portion of the protein. Suitable host animals include mice, rats, sheep, goats, hamsters, rabbits, and others. The immunogen may comprise the complete protein, or fragments and derivatives thereof. Preferred immunogens comprise all or a part of the protein, where the protein includes post-translation modifications found on the native target protein. Immunogens are produced in a variety of ways known in the art, for example, expression of cloned genes using conventional recombinant methods, or isolation directly from *Aequorea coerulscens*.

For preparation of polyclonal antibodies, the first step involves immunization of the host animal with the peptide immunogen, where the peptide protein immunogen preferably will be in substantially pure form, comprising less than about 1% contaminant. The immunogen may comprise a complete protein, or fragments or derivatives thereof. To increase the immune response of the host animal, the target protein may be combined with an adjuvant, where suitable adjuvants include alum, dextran, sulfate, large polymeric anions, oil and water emulsions, Freund's adjuvant, Freund's complete adjuvant, and the like. The peptide immunogen also may be conjugated to synthetic carrier proteins or synthetic antigens.

The peptide immunogen is administered to the host, usually intradermally, with an initial dosage followed by one or more, usually at least two, additional booster dosages. Following immunization, the blood from the host will be collected where the blood serum is separated from the blood cells. The immunoglobulin present in the resultant antiserum may be purified using known methods, such as ammonium salt fractionation, DEAE chromatography, and the like.

Alternatively, monoclonal antibodies may be produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mice, rats, hamsters and the like. To raise antibodies against the mouse protein, the animal will generally be a hamster, guinea pig, or rabbit. The antibody may be purified from the hybridoma cell supernatants or ascites fluid by conventional techniques, such as affinity chromatography using protein bound to an insoluble support like protein A sepharose.

The antibody may be produced as a single chain, instead of the normal multimeric structure. Single chain antibodies are described in Jost et al., *J.B.C.* 269:26267-73 (1994), and others. DNA sequences encoding the variable region of the heavy chain and the variable region of the light chain may be ligated to a spacer encoding at least about 4 amino acids of small neutral amino acids, including glycine and/or serine. The protein encoded by this fusion allows assembly of a functional variable region that retains the specificity and affinity of the original antibody.

Also of interest in certain embodiments are humanized antibodies. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of immunoglobulin cDNA for construction of chimeric immunoglobulin genes is known in the art (Liu et al., *Proceedings of the National Academy of Sciences* 84:3439 (1987) and *J. Immunol.* 139:3521 (1987)). Essentially, mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al., "Sequences of Proteins of Immunological Interest", *N.I.H. publication no.* 91-3242 (1991). Human C region genes are readily available from known clones. The choice of isotype will be guided by the desired effector functions, such as complement fixation, or activity in antibody-dependent cellular cytotoxicity. Preferred isotopes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, for example, by a protease or lay chemical cleavage. Alternatively, a truncated gene may be designed. For example, a chimeric gene encoding a portion of the F(ab')$_2$ fragment would indicate DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV-derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, such as the SV40 early promoter, (Okayama et al., *Mol. Cell. Bio.* 3:280 (1983)); Rous sarcoma virus LTR (Gorman et al., *Proceedings of the National Academy of Sciences.* 79:6777 (1982)); or moloney murine leukemia virus LTR (Grosschedl et al., Cell 41:885 (1985)); or native lg promoters etc.

Transgenics

The nucleic acids of the present invention can be used to generate transgenic, non-human plants or animals or site-specific gene modifications in cell lines. Transgenic cells of the subject invention include one or more nucleic acids according to the subject invention present as a transgene, where included within this definition are the parent cells transformed to include the transgene and the progeny thereof. In many embodiments, the transgenic cells are cells that do not normally harbor or contain a nucleic acid according to the present invention. In those embodiments where the transgenic cells do naturally contain the subject nucleic acids, the nucleic acid will be present in the cell in a position other than its natural location, such as being integrated into the genomic material of the cell at a non-natural location. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

Transgenic organisms of interest include cells and multicellular organisms, both plants and animals, in which the protein or variants thereof is expressed in cells or tissues where it is not normally expressed and/or at levels not normally present in such cells or tissues.

DNA constructs for homologous recombination will comprise at least a portion of a nucleic acid of the present invention, wherein the gene has the desired genetic modification(s), and includes regions of homology to the target locus. DNA constructs for random integration need not include regions of homology to mediate recombination. Conveniently, markers for positive and negative selection may be included. Methods for generating cells having targeted gene modifications through homologous recombination are known in the art. For various techniques for transfecting mammalian cells, see Keown et al., *Meth. Enzymol.* 185:527-37 (1990).

For embryonic stem (ES) cells, an ES cell line may be employed, or embryonic cells may be obtained freshly from a host, such as a mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time is given for colonies to grow, the colonies are picked and analyzed for the occurrence of homologous recombination or integration of the construct. Those colonies that are positive may then be used for embryo manipulation and blastocyst injection. Blastocysts are obtained from 4- to 6-week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring are screened for the construct. Chimeric progeny can be readily detected if the phenotype of transformed cells differs in some way from the naturally occurring cells (such as exhibiting fluroescence).

The chimeric animals are screened for the presence of the modified gene and males and females having the modification are mated to produce homozygous progeny. If the gene alterations cause lethality at some point in development, as is possible particularly with the fusion proteins of the present invention, tissues or organs can be maintained as allogeneic or congenic grafts or transplants, or in in vitro culture. The transgenic animals may be any non-human mammal, such as laboratory animals, domestic animals, etc., and used in functional studies, drug screening and the like. Representative examples of the use of transgenic animals include those described infra.

Transgenic plants also may be produced. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants also are reviewed in *Plant Biochemistry and Molecular Biology* (eds. Lea and Leegood, John Wiley & Sons) pp. 275-295 (1993). In brief, a suitable plant cell or tissue is harvested, depending on the nature of the plant species. As such, in certain instances, protoplasts will be isolated, where such protoplasts may be isolated from a variety of different plant tissues, e.g., leaf, hypocotyl, root, etc. For protoplast isolation, the harvested cells are incubated in the presence of cellulases in order to remove the cell wall, where exact incubation conditions will vary depending on the type of plant and/or tissue from which the cell is derived. The resultant protoplasts are then separated from the resultant cellular debris by sieving and centrifugation.

Alternatively, embryogenic explants comprising somatic cells may be used for preparation of the transgenic host. Following cell or tissue harvesting, exogenous DNA of interest is introduced into the plant cells, where a variety of different techniques is available for such introduction. With isolated protoplasts, the opportunity arises for introduction via DNA-mediated gene transfer protocols, including incubation of the protoplasts with naked DNA, such as plasmids comprising the exogenous coding sequence of interest in the presence of polyvalent cations (for example, PEG or PLO); or electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, such as auxins and cytokinins.

With embryonic explants, a convenient method of introducing the exogenous DNA in to the target somatic cells is through the use of particle acceleration or "gene-gun" protocols. The resultant explants are then allowed to grow into chimeric plants, are cross-bred, and transgenic progeny are then obtained.

Instead of the naked DNA approaches described above, another method of producing transgenic plants is via Agrobacterium-mediated transformation. With Agrobacterium-mediated transformation, co-integrative or binary vectors comprising the exogenous DNA are prepared and then introduced into an appropriate *Agrobacterium* strain, e.g., *A. tumefaciens*. The resultant bacteria are then incubated with prepared protoplasts or tissue explants, such as a leaf disk, and a callus is produced. The callus is then grown under selective conditions, selected and subjected to growth media to induce root and shoot growth to ultimately produce a transgenic plant.

Methods of Use

The fluorescent proteins and peptides of the present invention find use in a variety of different applications. Representative uses for each of these types of proteins will be described below, where the uses described herein are merely exemplary and are in no way meant to limit the use of the proteins of the present invention to those described.

The first application of interest is the use of the subject proteins in fluorescence resonance energy transfer (FRET) methods. In these methods, the subject proteins serve as donor and/or acceptors in combination with a second fluorescent protein or dye, for example, a fluorescent protein as described in Matz et al., *Nature Biotechnology* 17:969-973 (1999); a green fluorescent protein from *Aequorea victoria* or fluorescent mutant thereof, for example, as described in U.S. Pat. Nos. 6,066,476; 6,020,192; 5,985,577; 5,976,796; 5,968,750; 5,968,738; 5,958,713; 5,919,445; 5,874,304, the disclosures of which are herein incorporated by reference; other fluorescent dyes such as coumarin and its derivatives, 7-amino-4-methylcoumarin and aminocoumarin; bodipy dyes; cascade blue; or fluorescein and its derivatives, such as fluorescein isothiocyanate and Oregon green; rhodamine dyes such as Texas red, tetramethylrhodamine, eosins and erythrosins; cyanine dyes such as Cy3 and Cy5; macrocyclic chealates of lenthaninde ions, such as quantum dye; and chemilumescent dyes such as luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference.

Specific examples of where FRET assays employing the subject fluorescent proteins may be used include, but are not limited to, the detection of protein-protein interactions, such as in a mammalian two-hybrid system, transcription factor dimerization, membrane protein multimerization, multiprotein complex formation; as a biosensor for a number of different events, where a peptide or protein covalently links a FRET fluorescent combination including the subject fluorescent proteins and the linking peptide or protein is, for example, a protease-specific substrate for caspase-mediated cleavage, a peptide that undergoes conformational change upon receiving a signal which increases or decreases FRET, such as a PKA regulatory domain (cAMP-sensor), a phosphorylation site (for example, where there is a phosphorylation site in the peptide or the peptide has binding specificity to phosphorylated/dephosphorylated domain of another protein), or the peptide has $Ca^{2+}$ binding domain. In addition, fluorescence resonance energy transfer or FRET applications in which the proteins of the present invention find use include, but are not limited to, those described in: U.S. Pat. Nos. 6,008,373; 5,998,146; 5,981,200; 5,945,526; 5,945,283; 5,911,952; 5,869,255; 5,866,336; 5,863,727; 5,728,528; 5,707,804; 5,688,648; 5,439,797; the disclosures of which are herein incorporated by reference.

The subject fluorescent proteins also find use as biosensors in prokaryotic and eukaryotic cells, such as a $Ca^{2+}$ ion indicator; a pH indicator; a phorphorylation indicator; or as an indicator of other ions, such as magnesium, sodium, potassium, chloride and halides. For example, for detection of $Ca^{2+}$ ions, proteins containing an EF-hand motif are known to translocate from the cytosol to membranes upon $Ca^{2+}$ binding. These proteins contain a myristoyl group that is buried within the molecule by hydrophobic interactions with other regions of the protein. Binding of $Ca^{2+}$ induces a conformational change exposing the myristoyl group which then is available for the insertion into the lipid bilayer (called a "$Ca^{2+}$-myristoyl switch"). Fusion of such a EF-hand containing protein to fluorescent proteins would make it an indicator of intracellular $Ca^{2+}$ by monitoring the translocation from the cytosol to the plasma membrane by confocal microscopy. EF-hand proteins suitable for use in this system include, but are not limited to: recoverin, calcineurin B, troponin C, visinin, neurocalcin, calmodulin, parvalbumin, and the like.

For indicating pH, a system based on hisactophilins may be employed. Hisactophilins are myristoylated histidine-rich proteins known to exist in *Dictyostelium*. Their binding to actinand acidic lipids is sharply pH-dependent within the range of cytoplasmic pH variations. In living cells, membrane binding seems to override the interaction of isactophilins with actin filaments. At pH$\leq$6.5 they locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By fusing fluorescent proteins to hisactophilin, the intracellular distribution of the fusion protein can be followed by laser scanning, confocal microscopy or standard fluorescence microscopy.

For such studies, quantitive fluorescence analysis can be done by performing line scans through cells (laser scanning confocal microscopy) or other electronic data analysis (e.g., using metamorph software (Universal Imaging Corp)) and averaging of data collected in a population of cells. Substantial pH-dependent redistribution of hisactophilin/fluorescent protein from the cytosol to the plasma membrane occurs within 1-2 minutes and reaches a steady state level after 5-10 minutes. The reverse reaction takes place on a similar time scale. As such, a hisactophilin-fluorescent protein fusion protein that acts in an analogous fashion can be used to monitor cytosolic pH changes in real time in live mammalian cells. Such methods have use in high throughput applications, for example, in the measurement of pH changes as a consequence of growth factor receptor activation (e.g., epithelial or platelet-derived growth factor), chemotactic stimulation/cell locomotion, in the detection of intracellular pH changes as second messenger, in the monitoring of intracellular pH in pH manipulating experiments, and the like.

For detection of PKC activity, the reporter system exploits the fact that a molecule called MARCKS (myristoylated alanine-rich C kinase substrate) is a PKC substrate. MARCKS is anchored to the plasma membrane via myristoylation and a stretch of positively charged amino acids (ED-domain) that bind to the negatively-charged plasma membrane via electrostatic interactions. Upon PKC activation, the ED-domain becomes phosphorylated by PKC, thereby becoming negatively charged, and as a consequence of electrostatic repulsion MARCKS translocates from the plasma membrane to the cytoplasm (called the "myristoyl-electrostatic switch"). Fusion of the N-terminus of MARCKS from the the myristoylation motif to the ED-domain of MARCKS to the fluorescent proteins of the present invention provides a detector system for PKC activity. When phosphorylated by PKC, the fusion protein translocates from the plasma membrane to the cytosol. This translocation may be tracked by standard fluorescence microscopy or confocal microscopy, for example, by using Cellomics Inc., technology or other high content screening systems (such as those from Universal Imaging Corp., or Becton Dickinson). The above reporter system has application in high content screening for PKC inhibitors, and as an indicator for PKC activity inscreening assays for potential reagents that interfere with this signal tansduction pathway. Methods of using fluorescent proteins as biosensors also include those described in U.S. Pat. Nos. 5,972,638; 5,824,485 and 5,650,135 (as well as the references cited therein) the disclosures of which are herein incorporated by reference.

The fluorescent proteins of the present invention also find use in applications involving the automated screening of arrays of cells expressing fluorescent reporting groups by using microscopic imaging and electronic analysis. Screening can be used for drug discovery and in the field of functional genomics where the subject proteins are used as markers of whole cells to detect changes in multicellular reorganization and migration, for example in the formation of multicellular tubules (blood vessel formation) by endothelial cells, migration of cells through the Fluoroblok Insert system (Becton Dickinson Co.), wound healing, or neurite outgrowth. Screening can also be employed where the proteins of the present invention are used as markers fused to peptides (such as targeting sequences) or proteins that detect changes in intracellular location as an indicator for cellular activity, for example in signal transduction, such as kinase and transcription factor translocation upon stimuli. Examples include protein kinase C, protein kinase A, transcription factor NFkB, and NFAT; cell cycle proteins, such as cyclin A, cyclin B1 and cyclin E; protease cleavage with subsequent movement of cleaved substrate; phospholipids, with markers for intracellular structures such as the endoplasmic reticulum, Golgi apparatus, mitochondria, peroxisomes, nucleus, nucleoli, plasma membrane, histones, endosomes, lysosomes, or microtubules.

The proteins of the present invention also can be used in high content screening to detect co-localization of other fluorescent fusion proteins with localization markers as indicators of movements of intracellular fluorescent proteins/peptides or as markers alone. Examples of applications involving the automated screening of arrays of cells in which the subject fluorescent proteins find use include U.S. Pat. No. 5,989,835; as well as WO 0017624; WO 00/26408; WO 00/17643; and WO 00/03246; the disclosures of which are herein incorporated by reference.

The fluorescent proteins of the present invention also find use in high throughput screening assays. The subject fluorescent proteins are stable proteins with half-lives of more than 24 hours. Also provided are destabilized versions of the subject fluorescent proteins with decreased half-lives that can be used as transcription reporters for drug discovery. For example, a protein according to the subject invention can be fused with a putative proteolytic signal sequence derived from a protein with shorter half-life, such as a PEST sequence from the mouse ornithine decarboxylase gene, a mouse cyclin B1 destruction box or ubiquitin, etc. For a description of destabilized proteins and vectors that can be employed to produce the same, see e.g., U.S. Pat. No. 6,130,313; the disclosure of which is herein incorporated by reference. Promoters in signal transduction pathways can be detected using destabilized versions of the subject fluorescent proteins for drug screening such as, for example, AP1, NFAT, NFkB, Smad, STAT, p53, E2F, Rb, myc, CRE, ER, GR and TRE, and the like.

The proteins of the present invention can be used as photoactivated labels for precise in vivo photolabeling and following trafficking of proteins, organelles or cells as described in, for example, Patterson and Lippincoft-Scott, *Science*, 13:1873-77 (2002) and Ando, et al., *Proc. Natl. Acad. Sci. USA*, 99:12651-56 (2002).

Additionally, the subject proteins can be used as second messenger detectors by fusing the subject proteins to specific domains such as the PKCgamma Ca binding domain, PKC-gamma DAG binding domain, SH2 domain or SH3 domain, etc.

Secreted forms of the subject proteins can be prepared by fusing secreted leading sequences to the subject proteins to construct secreted forms of the subject proteins, which in turn can be used in a variety of different applications.

The subject proteins also find use in fluorescence activated cell sorting (FACS) applications. In such applications, the subject fluorescent protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

The subject proteins also find use as in vivo markers in transgenic animals. For example, expression of the subject protein can be driven by tissue-specific promoters, where such methods find use in research for gene therapy, such as testing efficiency of transgenic expression, among other applications. A representative application of fluorescent proteins in transgenic animals that illustrates such applications is found in WO 00/02997, the disclosure of which is herein incorporated by reference.

Additional applications of the proteins of the present invention include use as markers following injection into cells or animals and in calibration for quantitative measurements; as markers or reporters in oxygen biosensor devices for monitoring cell viability; as markers or labels for animals, pets, toys, food, and the like.

The subject fluorescent proteins also find use in protease cleavage assays. For example, cleavage-inactivated fluorescence assays can be developed using the subject proteins, where the subject proteins are engineered to include a protease-specific cleavage sequence without destroying the fluorescent character of the protein. Upon cleavage of the fluorescent protein by an activated protease, fluorescence would sharply decrease due to the destruction of the functional chromophore. Alternatively, cleavage-activated fluorescence can be developed using the proteins of the present invention where the proteins are engineered to contain an additional spacer sequence in close proximity/or inside the chromophore. This variant is significantly decreased in its fluorescent activity, because parts of the functional chromophore are divided by the spacer. The spacer is framed by two identical protease-specific cleavage sites. Upon cleavage via the activated protease, the spacer would be cut out and the two residual "subunits" of the fluorescent protein would be able to reassemble to generate a functional fluorescent protein. Both of the above applications could be developed in assays for a variety of different types of proteases, such as caspases and others.

The subject proteins also can be used in assays to determine the phospholipid composition in biological membranes. For example, fusion proteins of the subject proteins (or any other kind of covalent or non-covalent modification of the subject proteins) that allows binding to specific phospholipids to localize/visualize patterns of phospholipid distribution in biological membranes, while allowing co-localization of membrane proteins in specific phospholipid rafts, can be accomplished with the subject proteins. For example, the PH domain of GRP1 has a high affinity to phosphatidyl-inositol tri-phosphate (PIP3) but not to PIP2. As such, a fusion protein between the PH domain of GRP1 and the subject proteins can be constructed to specifically label PIP3-rich areas in biological membranes.

Yet another application of the subject proteins is as a fluorescent timer, in which the switch of one fluorescent color to another (e.g., green to red) concomitant with the aging of the fluorescent protein is used to determine the activation/deactivation of gene expression, such as developmental gene expression, cell cycle-dependent gene expression, circadian rhythm-specific gene expression, and the like.

The antibodies of the subject invention, described above, also find use in a number of applications, including the differentiation of the subject proteins from other fluorescent proteins.

Kits

Also provided by the present invention are kits for use in practicing one or more of the above-described applications, where the kits typically include elements for expressing the subject proteins, for example, a construct comprising a vector that includes a coding region for the subject protein. The kit components are typically present in a suitable storage medium, such as a buffered solution, typically in a suitable container. Also present in the kits may be antibodies to the provided protein. In certain embodiments, the kit comprises a plurality of different vectors each encoding the subject protein, where the vectors are designed for expression in different environments and/or under different conditions, for example, constitutive expression where the vector includes a strong promoter for expression in mammalian cells or a promoterless vector with a multiple cloning site for custom insertion of a promoter and tailored expression, etc.

In addition to the above components, the subject kits will further include instructions for practicing the subject methods. These instructions may be present in the subject kits in a variety of forms, one or more of which may be present in the kit. One form in which these instructions may be present is as printed information included in the packaging of the kit, such as a package insert. Yet another means would be a computer readable medium, e.g., diskette, CD, etc., on which the information has been recorded. Yet another means that may be present is a website address which may be used to access the information at a removed site via the internet. Any convenient means may be present in the kits.

The following example is offered by way of illustration and not by way of limitation.

EXAMPLE

Several specimens of large hydromedusa were collected at the Russian coast of the Japan Sea near Vladivostok in August 2001. A set of characteristic features permits identification of these medusae as *Aequorea coerulescens* (Kramp, *Dana Rept.*, 72:201-202 (1968); Pogodin and Yakovlev, *Rus. J. Mar. Biol.*, 25:417-419 (1999)). Although *A. coerulecens* and *A. Victoria* (synonyms of *A. forscalea, A. aequorea*) are similar, some of their features are very different. The most obvious difference is the number of tentacles: *A. victoria* carries only one tentacle per radial channel while *A. coeruilescens* possesses 4-6 tentacles between each pair of adjacent radial channels.

The *A. coerulescens* specimens caught were bioluminescent. In contrast to *A. Victoria*, they displayed a blue rather than green luminescence. No detectable fluorescence was observed in the *A. coerulescens* medusae in UV light or when using a fluorescent microscope. Nevertheless, a monoclonal antibody against *A. Victoria* GFP detected a GFP-like protein in the protein extract from *A. coerulescens*. FIG. 11 shows a protein gel-electrophoresis analysis of acGFP. FIG. 11a is a Western blot analysis of soluble protein extract from *A. coerulescens* using antibodies against *A. victoria* GFP. Lane 1 is purified recombinant *A. Victoria* GFP, Lane 2 is the *A. coerulescens* extract.

To clone the GFP-like protein, PCR was performed with degenerative primers corresponding to conservative amino acid sequences. A cDNA encoding a GFP-like protein was cloned. The nucleotide and amino acid sequence of the wild-type acGFP protein is shown in FIG. 1. The acGFP protein demonstrated very high similarity to GFP, having a 92% amino acid sequence similarity; see FIG. 2. All known key residues, including the chromophore-forming Ser65, Tyr66 and Gly67, the evolutionary invariant Arg96 and Glu222, and the residues spatially proximate to the chromophore, His148, Phe165, Ile167 and Thr203 were found unchanged in acGFP. Only three interior amino acids differed between these proteins.

Taking into account the very high sequence similarity, it was expected that the spectral properties of acGFP would be very similar to that of GFP. Nevertheless, *E. coli* colonies expressing acGFP showed neither fluorescence nor coloration. The most simple explanation of this fact—unsatisfactory acGFP folding in *E. coli*—was only partially correct, as was demonstrated in further experiments.

The presence of acGFP cDNA in various parts of the medusa was tested by PCR using specific primers. Three cDNA samples corresponding to the umbrella border, radial channel, and oral disc of the medusa were tested. AcGFP cDNA was clearly detected in the umbrella border but was absent in two other samples. Thus, distribution of acGFP within the *A. coerulescens* is similar to the distribution of GFP in *A. victoria*, which forms a fluorescent ring in *A. victoria* umbrella border.

Random mutagenesis of acGFP produced many green fluorescent clones, some of which were characterized. Their properties and possible applications are similar to those for the enhanced GFP (EGFP) mutant of *A. victoria*.

Mutant Z1 contained one amino acid substitution, E222G (a glycine for a glutamic acid at position 222), as seen in FIG. 3. The mutant Z1 protein possessed low brightness, very slow folding and required a temperature of less than 20° C. for maturation. After growth at 30° C., *E. coli* colonies expressing Z1 must be stored for 3-5 days at room temperature or at 4° C. for the fluorescence to become visible. Excitation and emission spectra for the Z1 mutant have maxima at 480 and 504 nm, respectively (see FIG. 4).

Mutant Z2 contained two amino acid substitutions, specifically, N19D (an aspartic acid for an asparagine at position 19) and E222G (a glycine for a glutamic acid at position 222) as seen in FIG. 5. The mutant Z2 possessed low brightness, very slow folding efficiency and required a temperature of less than 20° C. for maturation. After overnight growth at 37° C., E. coli colonies expressing Z2 must be stored for 3-5 days at room temperature or at 4° C. for the fluorescence to become visible. Excitation and emission spectra for the Z2 mutant are very similar to those of the mutant Z1.

Mutant G1 has substitutions V11I (an isoleucine for a valine at position 11), K101E (a glutamic acid for a lysine at position 101), and E222G (a glycine for a glutamic acid at position 222) as seen in FIG. 6. Mutant G1 was generated in an independent round of random mutagenesis. Since substitution E222G was found in three of the mutants, it seemed likely that this mutation was important for the green fluorescence of these mutants. Mutant G1 possesses rather low brightness. Fluorescence of this mutant becomes visible on the first day after overnight growth of the E. coli. The excitation and emission spectra of mutant G1 are very similar to those of the mutant Z1.

Figure 8:
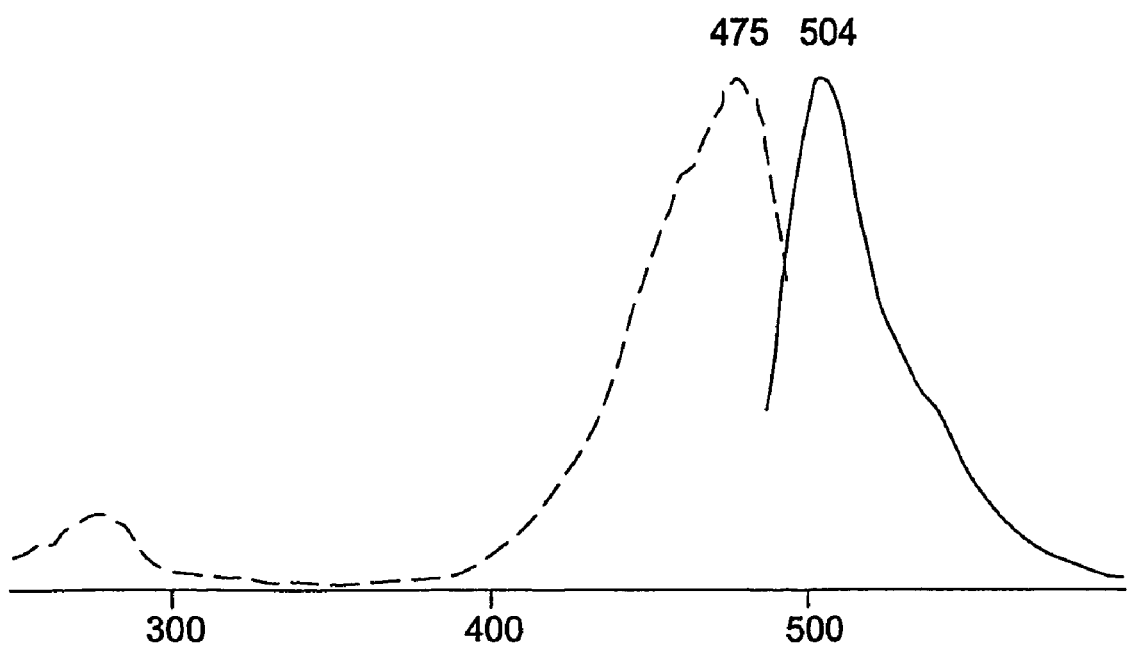
FIG. 8 is the excitation-emission spectra for mutant G2.

Mutant G2 has substitutions V11I (an isoleucine for a valine at position 11), F64L (a leucine for a phenylalamine at position 6A), K101E (a glutamic acid for a lysine at position 101), and E222G (a glycine for a glutamic acid at position 222) as seen in FIG. 7. Mutant G2 was generated based on mutant G1 using a second round of random mutagenesis. In comparison to G1, the G2 mutant protein possesses improved brightness and protein folding rate characteristics. Interestingly, G2 contains the substitution F64L that is also characteristic for enhanced GFP (EGFP) (Cormack et al., *Gene*, 173:33-38 (1996); Yang et al., *Nuc. Acids Res.*, 24:45924593 (1996)). Spectral properties of G2 are shown in Table 1, infra. The excitation-emission spectra for G2 are shown in FIG. 8.

Figure 10:
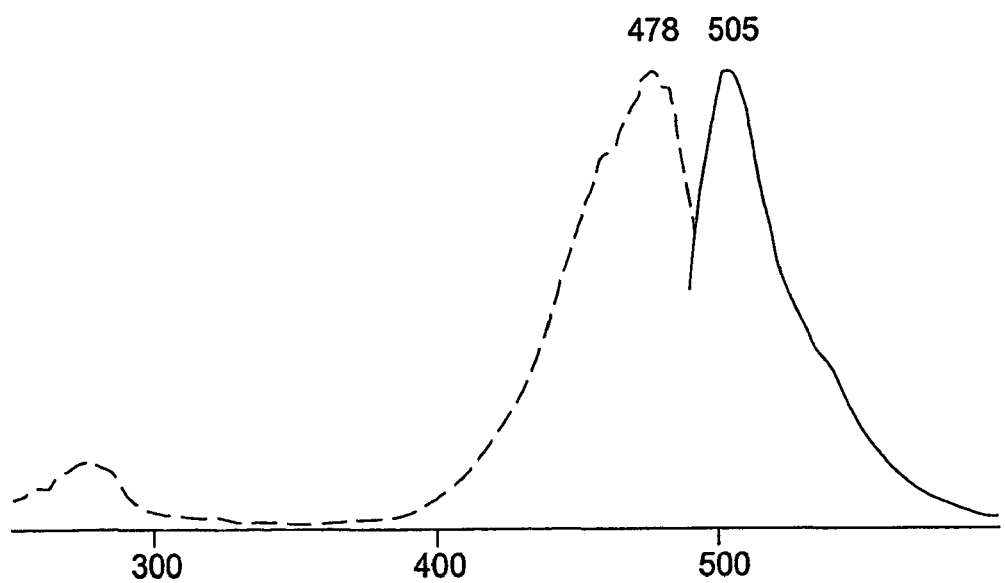
FIG. 10 is the excitation-emission spectra for mutant G22.

Mutant G22 has substitutions V11I (an isoleucine for a valine at position 11), F64L (a leucine for phenylalmine at position 64), K101E (a glutamic acid for a lysine at position 101), T206A (an alanine for a threonine at position 206), and E222G (a glycine for a glutamic acid at position 222) as seen in FIG. 9. Mutant G22 was generated from mutant G2 using a third round of random mutagenesis. In comparison to G2, G22 possesses even greater improved brightness. The spectral properties of G22 are reported in Table 1. The excitation-emission spectra for G22 are shown in FIG. 10. An extinction coefficient of 50,000 $M^{-1}$ $cm^{-1}$ and a quantum yield of 0.55 make this protein nearly as bright as the widely used enhanced GFP. Gel-filtration tests as well as SDS-PAGE of the non-heated mutant G22 protein demonstrated that G22 is monomeric. FIG. 11B compares the mobility of heated (lanes 1-3) versus non-heated (lanes 4-6) protein samples. Lanes 1 and 4 are *A. victoria* GFP, lanes 2 and 5 are the G22 mutant, and lanes 3 and 6 are the G22-G222E mutant. Coomassie blue staining is shown on the left and fluorescence of the non-heated proteins under UV light is shown on the right.

All of the fluorescent mutants of acGFP mentioned above have similar excitation and emission spectra, peaking at 470-480 nm and 500-510 nm, respectively. The shape of their excitation spectra are similar to that of enhanced GFP, but not wild type *A. victoria* GFP. It is likely that the fluorophore of the acGFP mutants is always in a deprotonated form, as it has been shown to be for enhanced GFP. A possible explanation is absence of Glu222, which may likely be important for proton transfer (Ehrig et al., *FEBS Lett.*, 367:163-166 (1995)).

To clarify the importance of the E222G substitution for fluorescence, a reverse G222E substitution was made to the mutant G22 (substitutions V11I, F64L, K101E, T206A). The nucleic acid and amino acid sequences of this reverse mutant G22-E222G is shown in FIG. 12. The reverse mutation readily transformed the G22-E222G mutant protein into a colorless state. E. coli colonies expressing G22-G222E displayed neither coloration nor detectable fluorescence.

Figure 13A:
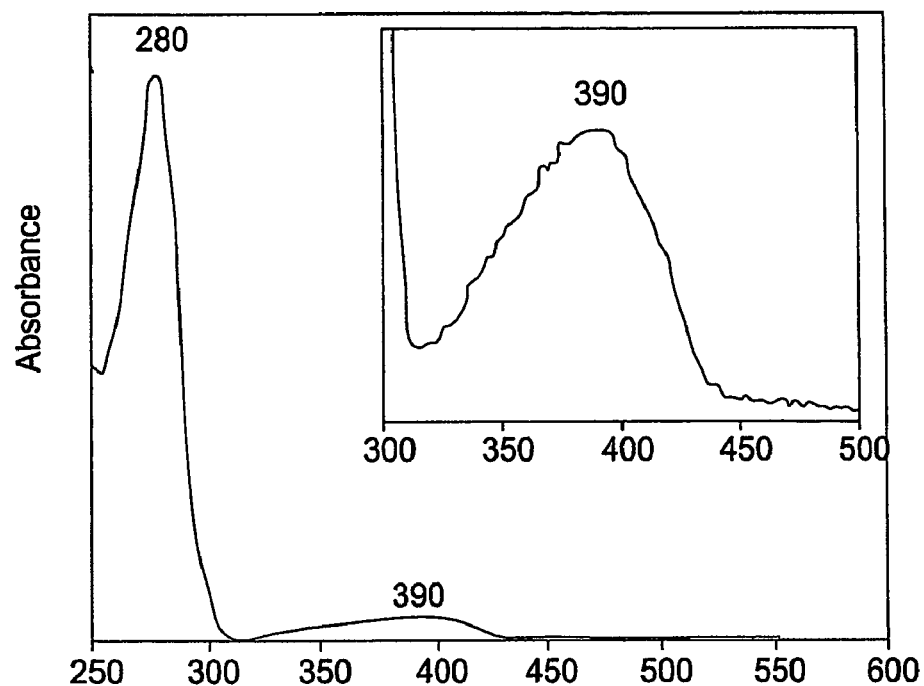
FIG. 13(*a-b*) are the absorption and excitation-emission spectra for mutant G22-G222E.
Figure 13B:
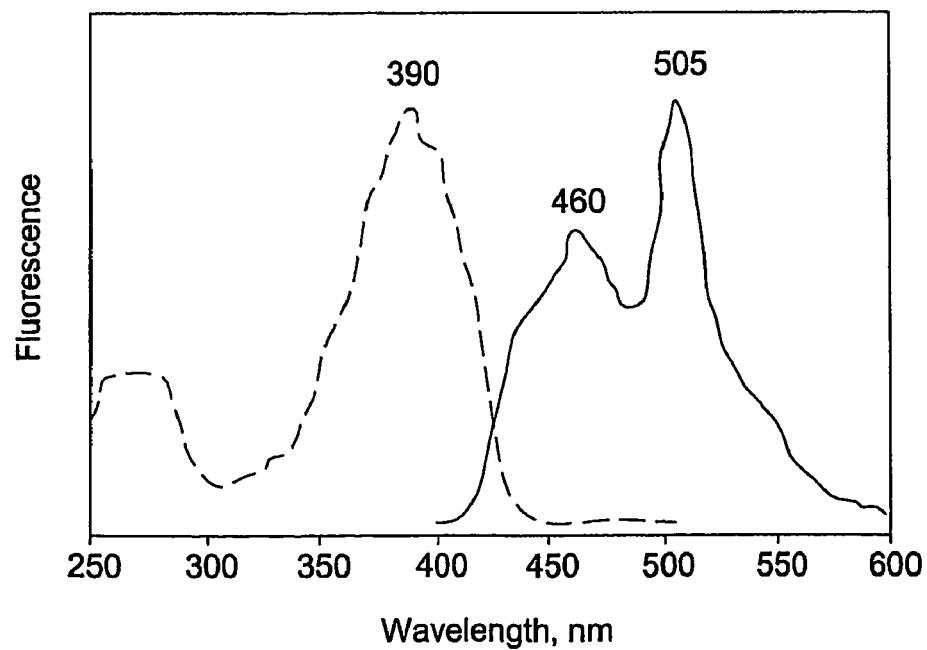

G22-G222E was expressed and folded in E. coli at 37° C. without a problem, as evidenced by the high yield of the soluble recombinant protein (about 20% of total proteins). Purified G22-G222E displayed an absorption spectrum with a major peak at 280 nm and a minor peak at 390 nm (see FIG. 13A). Alkali-denatured G22-G222E protein showed absorption peak at 446 nm that apparently corresponds to the anionic form of the GFP chromophore. Assuming an extinction coefficient 44,000 $M^{-1}$ $cm^{-1}$ for the chromophore, the extinction of native G22-G222E at 390 nm was estimated to be 33,000 $M^{-1}$ $cm^{-1}$. The observed ratio between the 280-nm and 390-nm peaks (molar extinction coefficient at 280 nm was calculated to be 23,500 $M^{-1}$ $cm^{-1}$) showed that only about 3% of soluble G22-G222E existed in a mature form. Excitation at 390 nm led to a weak dual-color fluorescence peaking at 460 nm and 505 nm with a quantum yield of 0.07 (see FIG. 13B).

It is well-known that GFP-like proteins retain their spectral properties and oligomerization state under conditions of common SDS-PAGE as long as the protein samples are not heated before being loading onto the gel. This test was used to examine the folding state of G22-G222E. Gel-electrophoresis demonstrated a clear difference in the mobility of non-denatured and denatured proteins (see FIG. 11). In addition, the non-heated G22-G222E protein band produced very weak fluorescence under UV light (again, see FIG. 11). As about 97% of this protein is present in a non-absorbing form, these results indicate that the conformation of this non-absorbing form is close to the native state, but not to the denatured state.

Encouraged by these results, the attempts to obtain and characterize the recombinant wild type acGFP were repeated. Growth of E. coli expressing acGFP at room temperature without induction, followed by a several days incubation at 4° C., resulted in the appearance of a small fraction of soluble acGFP (about 5% of total acGFP). Shapes of the absorption and fluorescence spectra for the soluble wild type acGFP were very similar to that of G22-G222E. It was concluded that G22-G222E mutant mirrors the properties of the natural acGFP but possesses improved protein folding and temperature stability when expressed in E. coli.

These data showed that soluble G22-G222E as well as the wild type acGFP exists in two forms. The majority of these proteins are present in a folded but immature form without a spectrally-detectable chromophore. The minor 390 nm-absorbing form contains a GFP-like chromophore in a neutral state and possesses weak dual-color fluorescence.

Figure 14:
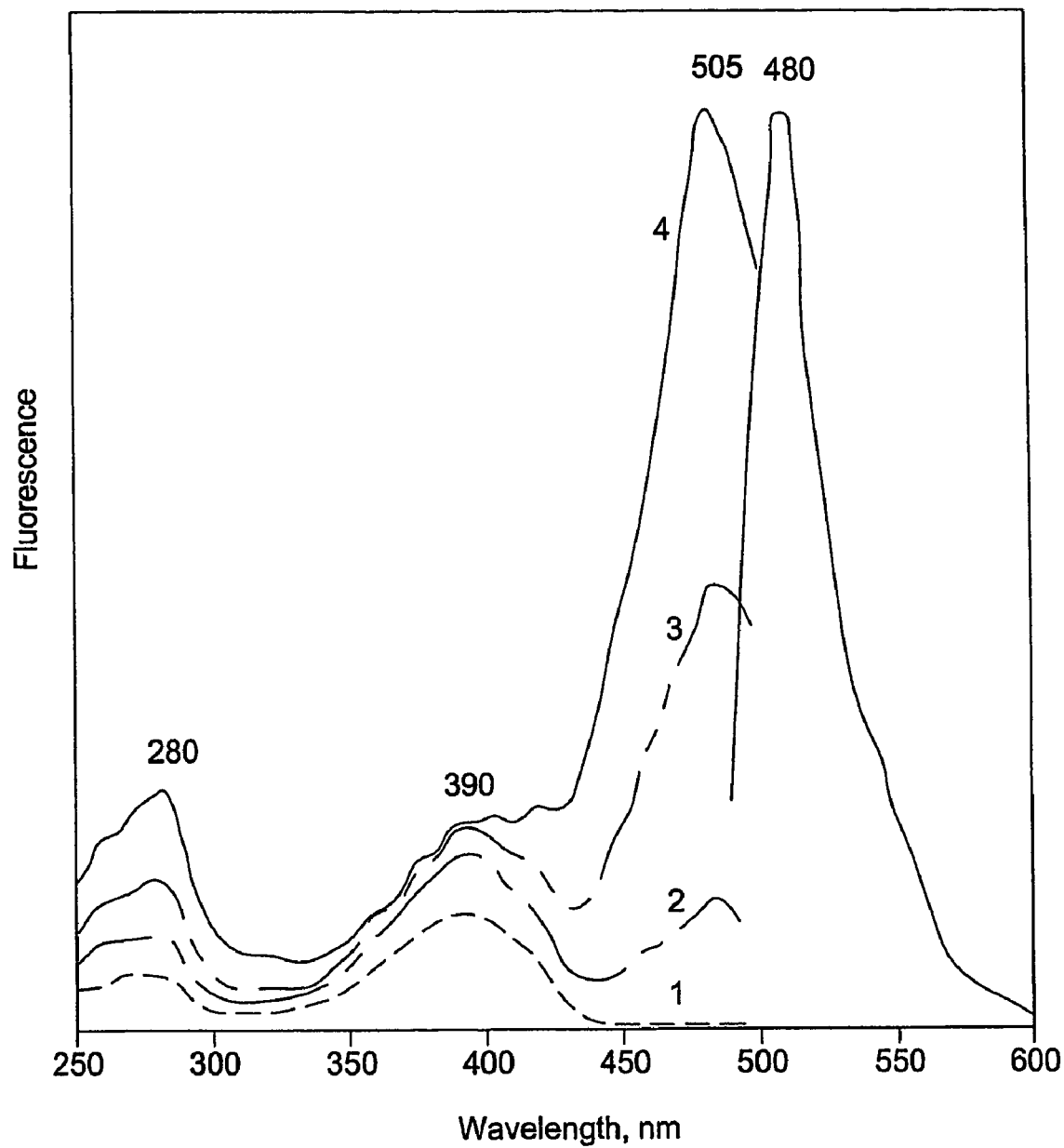
FIG. 14 provides the spectra for UV-induced photoconversion of G22-G222E.

A novel type of photoconversion was observed in mutant G22-G222E. Irradiation of a G22-G222E protein sample with 250-300 nm UV light resulted in the appearance of a 480 nm peak in the absorption/excitation spectra. Note in FIG. 14 the excitation spectrum of G22-G222E before irradiation (line1) and the gradual change of the curve due to irradiation of the protein sample with light at 250-300 nm. The unnumbered line represents the emission spectrum after photoconversion (excitation at 480 nm). This may originate from an immature, spectrally undetectable form of the protein, as the 390 nm absorption peak did not decrease during this photoconversion. Excitation at the 480 nm peak produced green fluorescence at 505 nm with a high quantum yield (0.45). A greater than 1000-fold UV-induced enhancement of green fluorescence intensity was achieved (excitation at 480 nm).

Figure 16:
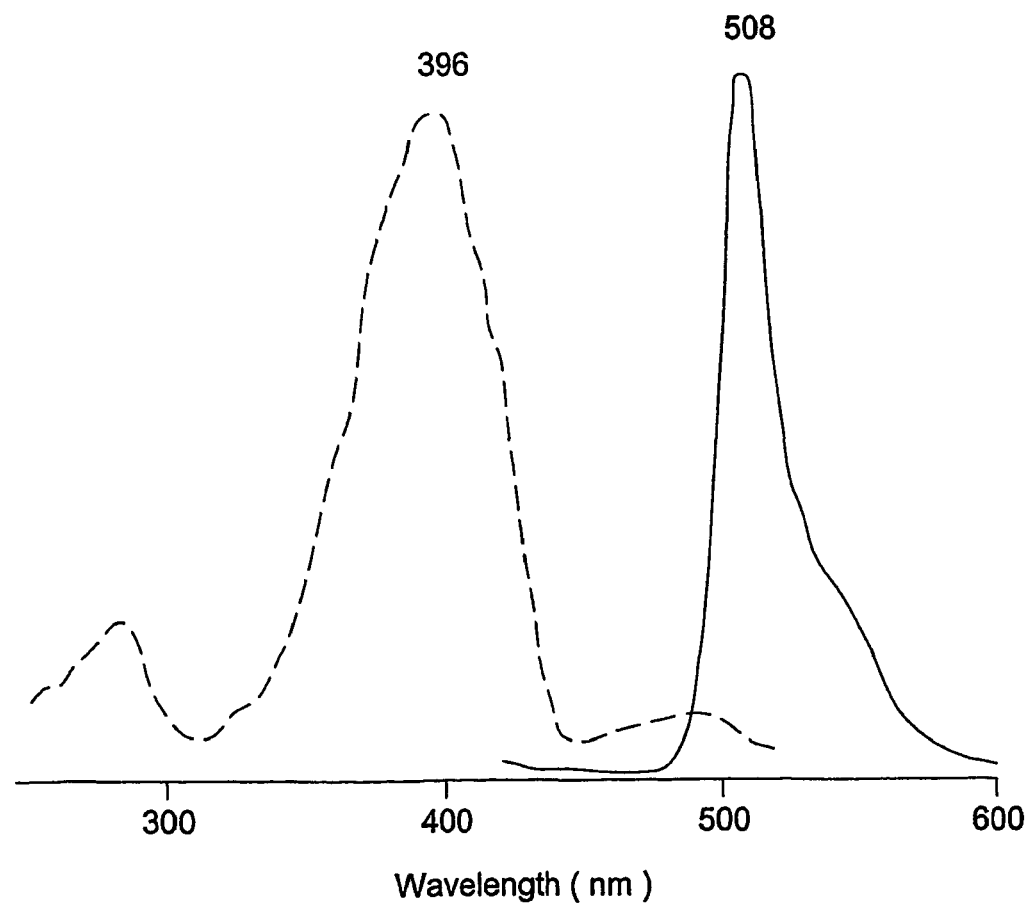
FIG. 16 is the excitation-emission spectra for mutant G22-G222E/Y220L.

Mutant G22-G222E/Y220L has substitutions V11I (an isoleucine for a valine at Position 11), F64L (a leucine for a phenylalanine at position 64), Vg8A (an alanine for a valine at position 68) K101E (a glutamic acid for a lysine at position 101), T206A (an alanine for a threonine at position 206), and Y220L (a leucine for a tyrosine at position 220) compared to the wild type acGFP, as seen in FIG. 15. This mutant demonstrated protein folding at 37° C. and possessed clear green fluorescence at 508 nm. The excitation spectrum for the G22-G222E/Y220L had a major peak at 396 nm and a minor peak at 493 nm (ratio 10:1) (see FIG. 16 where the excitation spectra is the dotted line and the emission spectra is the solid line). Spectral properties of this mutant were very similar to that of wild type GFP from *Aequorea victoria*.

Figure 18A:
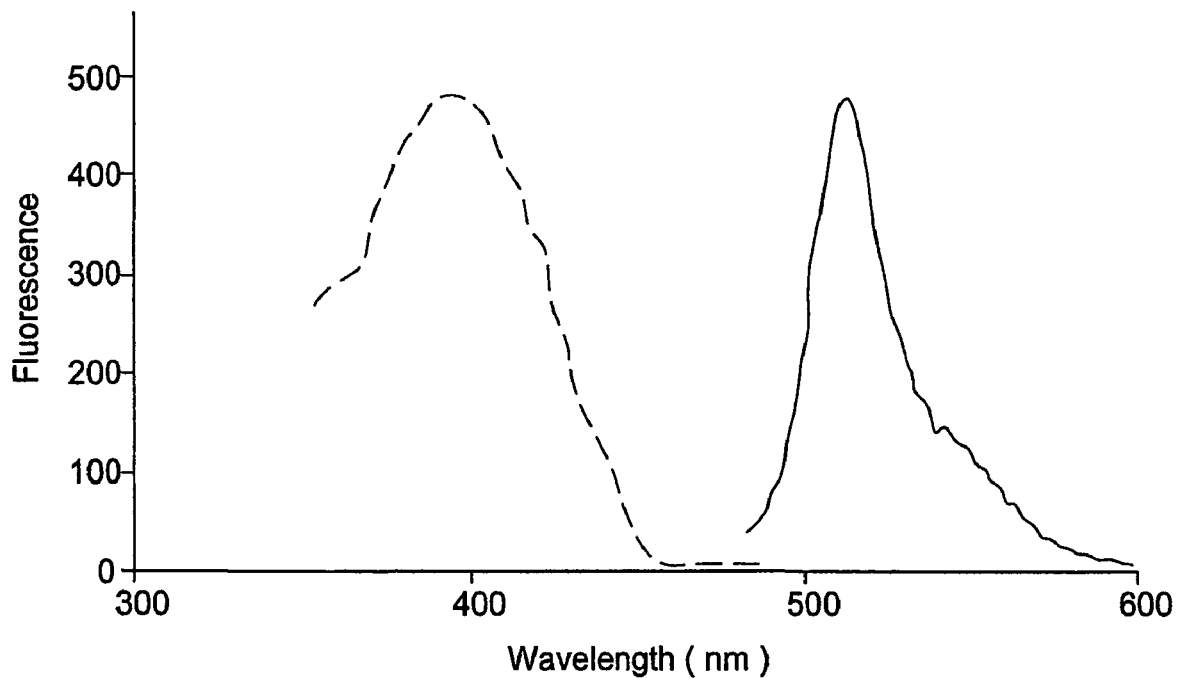
FIG. 18(*a-b*) provide spectral properties of mutant 220-II-5.
Figure 18B:
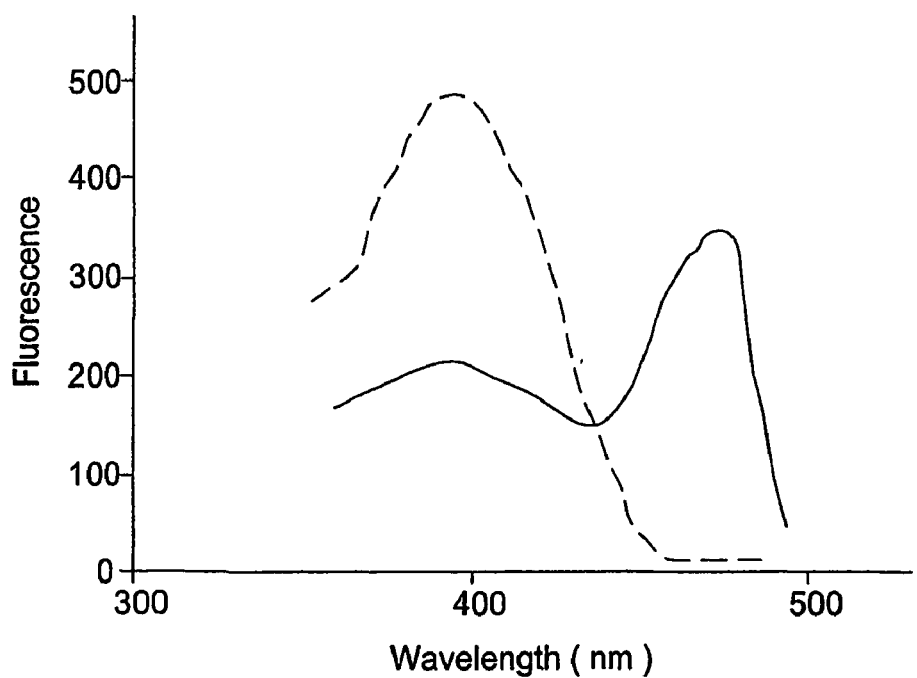
Figure 25:
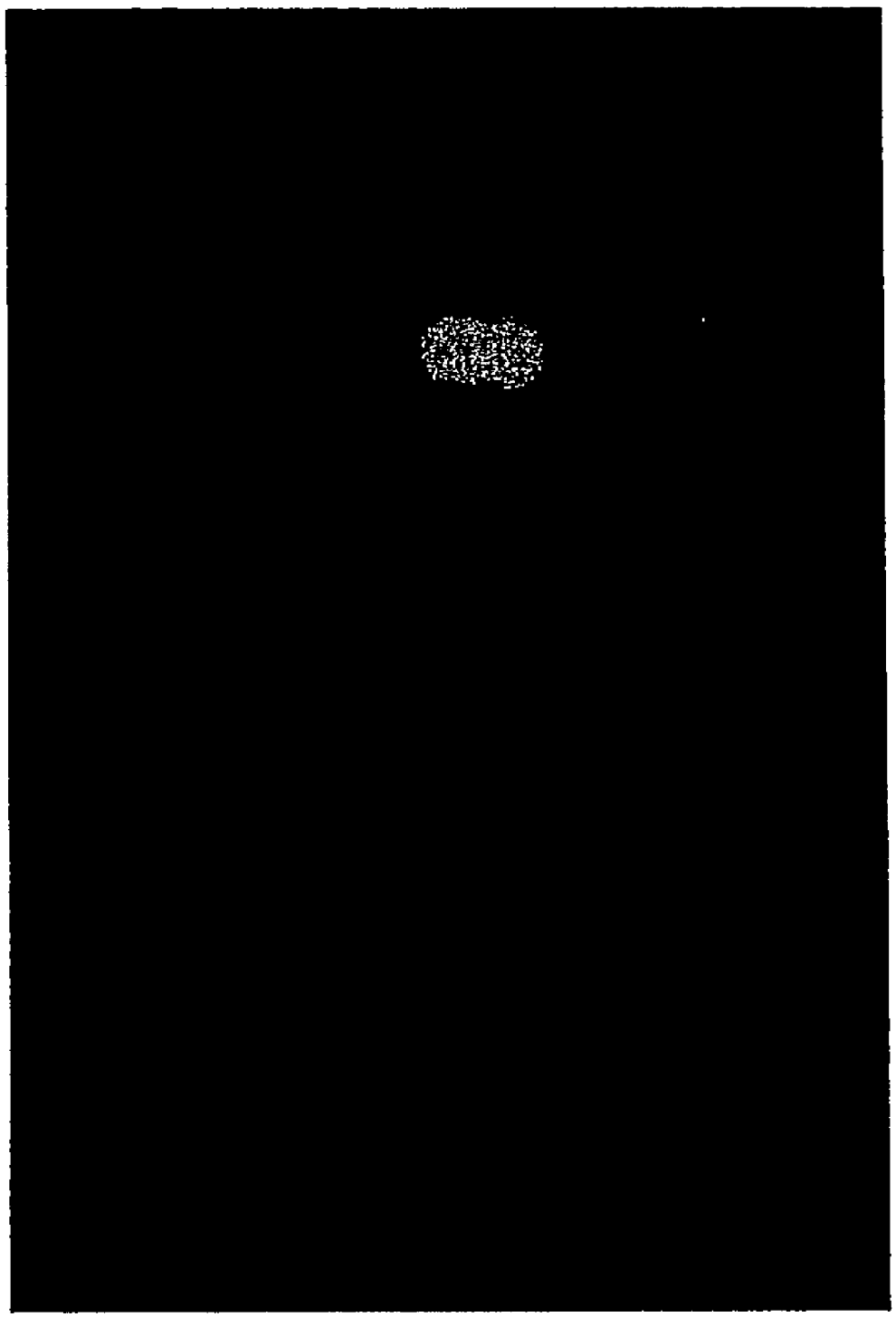
FIG. 25 shows the photoactivation of mutant 220-II-5 in *E. coli* colonies.

Using mutant G22-G222E/Y220L as a basis, mutant 220-II-5 was obtained having substitutions V11I (an isoleucine for a valine at Position 11), F64L (a leucine for a phenylalanine at position 64), K101E (a glutamic acid for a lysine at position 101), E115K (a lysine for a glutamic acid at position 115), H148Q (a glutamine for a histidine at position 148), T206A (an alanine for a threonine at position 206), Y220L (a leucine for a tyrosine at position 220), F221L (a leucine for aphenylalanine at position 221), and K238Q (a glutamine for a lysine at position 238). The nucleic acid and amino acid sequences for this mutant are in FIG. 17. Thus mutant has a major excitation peak at 395 nm, and no excitation peak at about 480 nm, with the emission peak at 512 nm (see FIG. 18A). It is likely that the suppression of the longer-wavelength excitation peak can be explained by the substitution H148Q that results in a disappearance of the fraction of charged chromophore. After several minutes of relatively intense irradiation with light at approximately 400 nm under a fluorescent microscope, the excitation spectrum of mutant G22-G222E/Y220L changed. There was a simultaneous decrease of the 395 nm peak and appearance of the 480 nm excitation peak (see FIG. 18B). As a result, a more than 100-fold contrast in the fluorescent brightness of the 510 nm emission can be obtained in the 480 nm excitation light, as compared to before and after irradiation of intense light of 400 nm wavelength. FIG. 25 shows two *E. coli* colonies expressing mutant 220-11-5 under a fluorescent microscope. The two areas in the upper colony were photoactivated preliminarily by an intense 400 nm light. As such, the G22-G22E/Y220L mutants can be used as a photoactivated fluorescent marker for photo-labeling living organisms similar to the recently published methods for use of PA-GFP mutant in Patterson and Lippincott-Schwartz, *Science*, 13:1873-1877 (2002).

Figure 20:
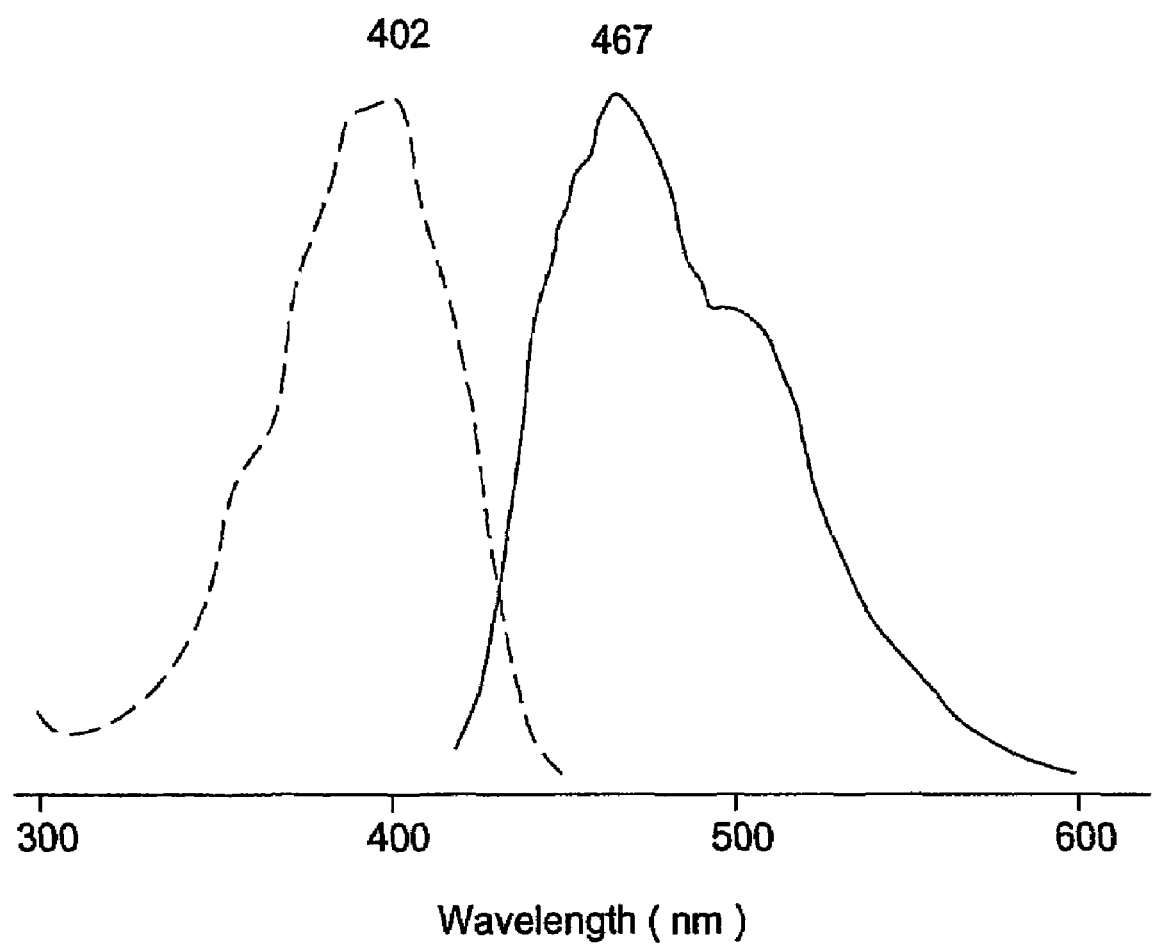
FIG. 20 is the excitation-emission spectra for mutant CFP-rand3.

Cyan fluorescent protein mutant CFP-rand3 has substitutions at V11I (isoleucine for valine at position 11), T62A (alanine for threonine at position 62), F64L (leucine for phenylalanine at position 64), K101E (glutamic acid for lysine at position 101), N121S (serine for asparagine at position 121), H148T (threonine for histidine at position 148), E172K (lysine for glutamic acid at position 172), and T206A (alanine for threonine at position 206). The amino and nucleic acid sequences for the CFP-rand3 mutant are shown in FIG. 19. This mutant has an excitation peak at 402 nm, with a single emission peak at 467 nm (see FIG. 20).

Figure 22A:
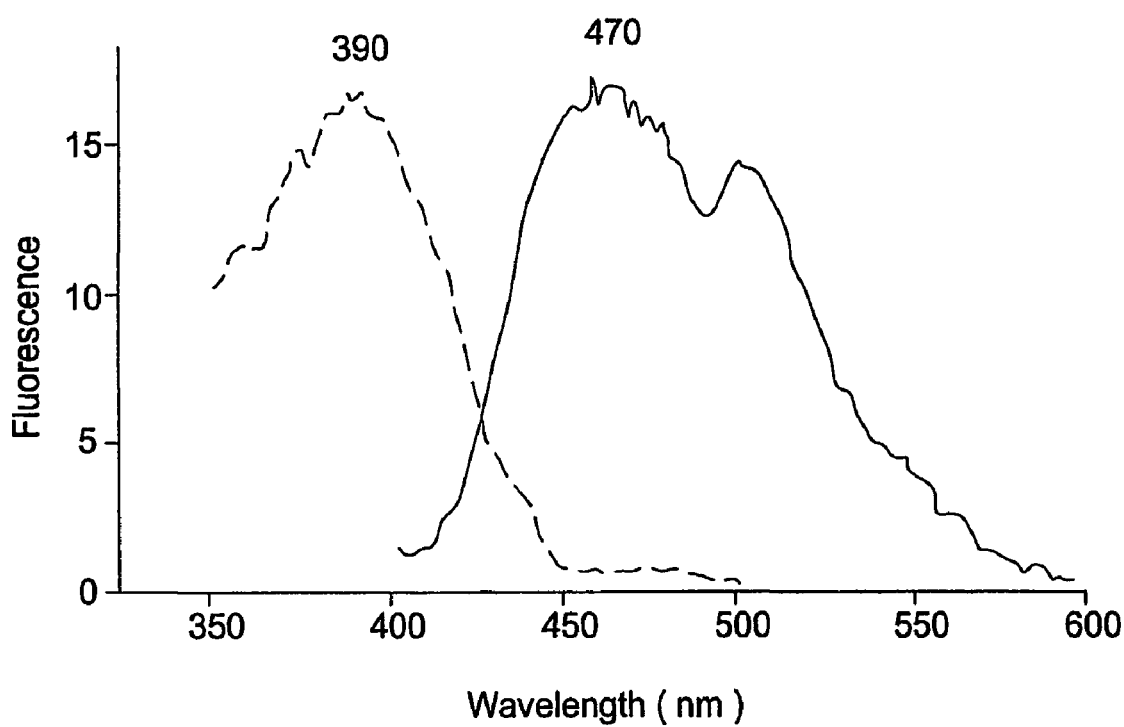
FIG. 22*a-b* provide spectral properties of mutant CFP-3.
Figure 22B:
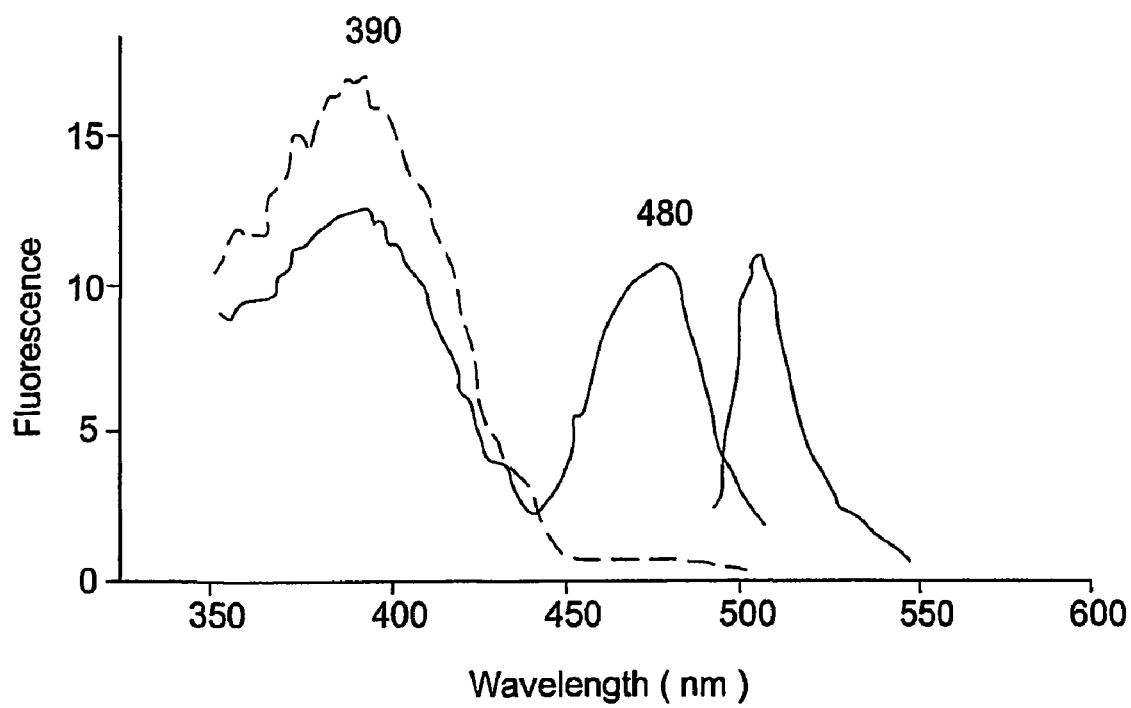

Another mutant cyan fluorescent protein, CFP-3, was generated having substitutions V11I (isoleucine for valine at position 11), F64L (a leucine for a phenylalanine at position 64), K101E (glutamic acid for lysine at position 101), H148S (serine for histidine at position 148), F165L (leucine for phenylalanine at position 165), E172A (alanine for glutamic acid at position 172), and T206A (alanine for threonine at position 206). The amino and nucleic acid sequences for this mutant are shown in FIG. 21. This mutant has an excitation peak at 390 nm, with a single emission peak at 470 nm FIG. 22A. After several minutes of relatively intense irradiation with light at 400 nm, the following changes of excitation and emission spectra were observed: (i) considerable decrease in the 390-nm excitation peak, and (ii) appearance of a 480 nm excitation peak with emission at 505 nm (see FIG. 22B).

As a result, a more than 30-fold contrast in the fluorescent brightness of the 505 nm emission may be obtained using excitation light at 480 nm, comparing the spectra before and after intense irradiation at 405 nm. Simultaneous change of the excitation and emission parameters transforms the cyan mutant CFP-3 to a green fluorescent protein in response to intense 400 nm irradiation. Therefore, the CFP-3 mutant can be used as a photoactivated or "photo-switched" fluorescent marker for photo-labeling of living organisms.

In one exemplary experiment, the G22 mutant was used as a fluorescent tag to test protein expression in mammalian cells. Unexpectedly, however, mutant G22 produced a very low fluorescent signal in human cell lines. This likely can be explained by either non-optimal codon usage or by presence of a cryptic intron in the G22 mutant gene. To overcome both these problems, a G22-h mutant gene was synthesized incorporating mammalian-optimized codon usage. The amino and nucleic acid sequences for this humanized mutant are shown in FIG. 23. Transient expression of G22-h in different cell lines showed a bright green signal without aggregation.

Figures 24A, 24B, 24C, 24D, 24E, 24F:
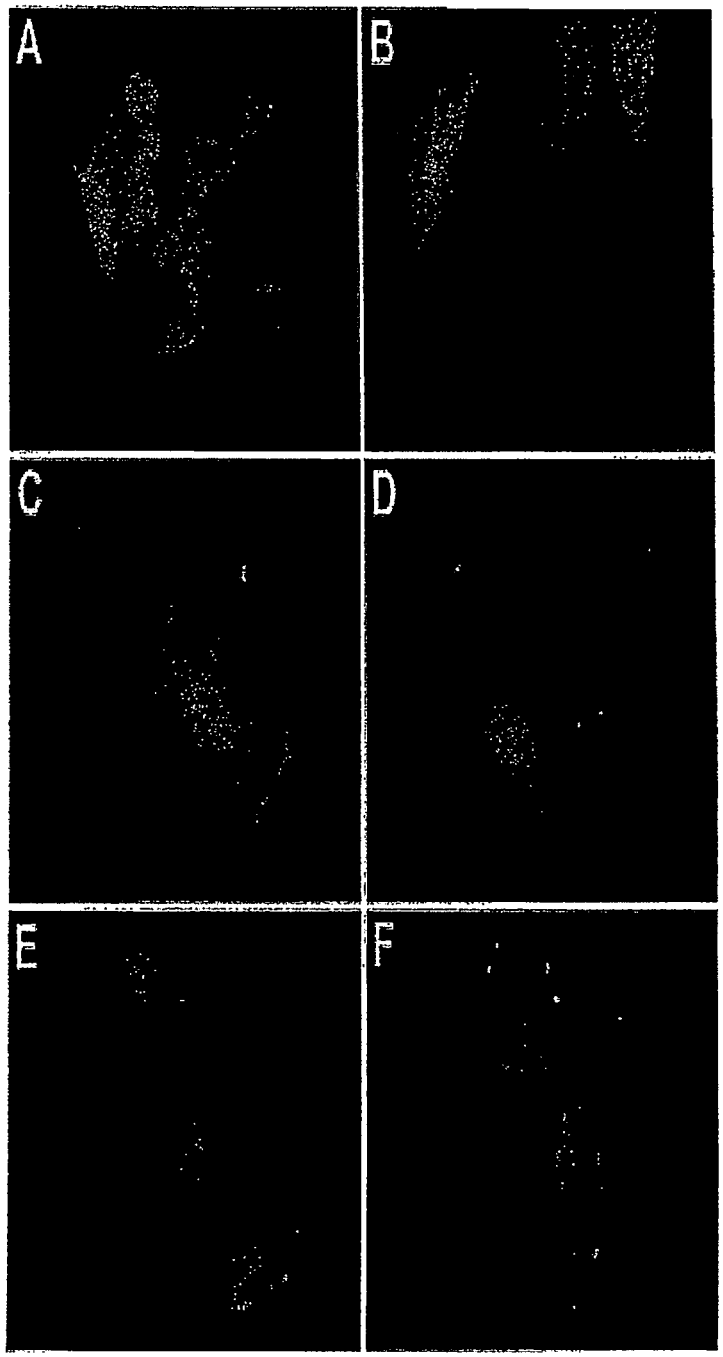
FIG. 24(*a-f*) show microphotographs of mammalian cells expressing mutant G22.

FIG. 24 shows transient expression of the G22-h mutant (panels A-E), and a G22-β-actin fusion protein (panel F) in different mammalian cell lines. Panel A-293T; panel B-vero; panel C-3T3; panel D-L929; panel E-COS1; panel F-3T3. Fluorescence was clearly detectable 24 hours post-transfection. No toxicity was observed. The ability of G22-h to tag proteins was demonstrated by constructing a fusion protein with cytoplasmic β-actin. Transient expression of this fusion in 3T3 cells showed bright and accurate actin labeling (see FIG. 24F). Stress fibers, focal contacts and cell possesses were clearly visible. There was no observed detriment to cell adhesion or vitality, nor was any non-specific protein aggregation observed.

Methods:

Total RNA was isolated using a NucleoSpin RNA II kit (Clontech) from a small vivsection of an *Aequorea coerulescens* organism that included umbrella border and radial channel. cDNA was synthesized and amplified with a SMART PCR cDNA Synthesis kit (Clontech). A fragment of the novel fluorescent protein gene was obtained by PCR with degenerated primers. A step-out PCR RACE method was used to clone the 5'-end fragment of the target cDNA. The nucleotide sequence of the cDNA encoding the novel fluoresent protein, acGFP, has been submitted to GenBank with accession number AY151052. For bacterial expression of acGFP, the full-length coding region was amplified using specific primers and cloned into the pQE30 vector (Qiagen).

A Diversity PCR Random Mutagenesis kit (CLONTECH) was used for random mutagenesis of acGFP, in conditions optimal for 5-6 mutations per 1000 basepairs. *E. coli* colonies expressing mutant proteins were screened visually with a fluorescent stereomicroscope SZX-12 (Olympus). The brightest variants were selected and subjected an additional round of random mutagenesis. Site-directed mutagenesis was performed by PCR using the overlap extension method, with primers containing appropriate target substitutions (see, for example, Ho et al., *Gene*, 77:51-59 (1989)).

Proteins fused to an N-terminal six-histidine tag were expressed in *E. coli* XL1 blue strain (Invitrogen) and purified using TALON metal-affinity resin (Clontech). Absorption spectra were recorded with a Beckman DU520 UV/VIS Spectrophotometer. A Varian Cary Eclipse Fluorescence Spectrophotometer was used for measuring excitation-emission spectra.

For molar extinction coefficient determination, estimation of mature chromophore concentration was used. Proteins were alkali-denatured with an equal volume of 2M NaOH. Under these conditions, the *A. victona* GFP chromophore absorbs at 446 nm and its molar extinction coefficient equals 44,000 $M^{-1}cm^{-1}$ (Ward et al., *Photochem. Photobiol.*, 31:611-615 (1980)). Absorption spectra for native and alkali-denatured proteins were measured. The molar extinction coefficients for the native state were estimated using the absorption of denatured proteins as a basis. For quantum yield determination, the fluorescence of the mutants was compared to that of enhanced GFP (quantum yield 0.60).

UV-induced photoconversion of acGFP-G222E was performed using a Cary Eclipse Fluorescence Spectrophotometer. The protein sample was irradiated for several hours with 250-300 nm wavelength light in scanning mode (excitation slit 20 nm, scan rate 30 nm/min, averaging time 1 second, cycle mode).

Purified protein samples (~1 mg/ml) were loaded onto a Sephadex-100 column (0.7×60 cm) and eluted with 50 mM phosphate buffer (pH 7.0) with 100 mM NaCl. EGFP, HcRed1, and DsRed2 (Clontech) were used as monomer, dimer and tetramer standards, respectively.

For protein gel analysis, heated and unheated samples were loaded onto a common 12% SDS-PAGE, and electrophoresis was carried out at 15 mA/gel. For Western blotting, proteins were transferred onto a Hybond C membrane (Amersham) using standard procedures. Membranes were probed with mouse antibodies (Clontech) against GFP (1:2500), and then with HRP-conjugated anti-mouse antibodies (Amersham) at 1:2500. To develop the staining pattern, an ECL Western blotting analysis system (Amersham Pharmacia Biotech) was used, including detection reagents 1, 2 and Hyperfilm ECL.

For expression in eukaryotic cells, acGFP was cloned into pEGFP-C1 and pEGFP-Actin vectors (CLONTECH) between AgeI and BglI restriction sites (in lieu of the EGFP coding region). The following cell lines were used: human kidney epithelial cells 293T, mouse embryo fibroblasts 3T3, murine subcutaneous fibroblasts L929, African green monkey kidney epithelial cells Vero, and African green monkey kidney fibroblasts COS1. Cells were transfected with LipofectAMINE reagent (Invitrogen) and were tested 20 hours after transfection. An Olympus CK40 fluorescent microscope equipped with CCD camera DP-50 (Olympus) was used for cell imaging.

TABLE 1

Spectral properties of acGFP mutants in comparison with EGFP.

| Species | Protein name | Absorption max, nm | Emission max, nm | Maximal extinction coefficient, $M^{-1}cm^{-1}$ | Quantum yield | Relative brightness** |
|---|---|---|---|---|---|---|
| *Aequorea victoria* | EGFP* | 488 | 509 | 53,000 | 0.60 | 1 |
| *Aequorea coerulescens* | Wild type acGFP | 390 | 460, 505 | nt | nt | nt |
| | Mutant G2 | 475 | 504 | 58,000 | 0.38 | 0.69 |
| | Mutant G22 | 480 | 505 | 50,000 | 0.55 | 0.86 |
| | Mutant G22-G222E*** | 390 | 460, 505 | 33,000 | 0.07 | 0.07 |
| | Mutant CFP-rand3 | 402 | 467 | 35,000 | 0.30 | 0.33 |

*Data from reference: Patterson, G., Day, R. N., and Piston, D. (2001) Fluorescent protein spectra. J. Cell. Sci. 114, 837-838
**As compared to the brightness (extinction coefficient multiplied by quantum yield) of EGFP.
***Data on mature fraction of the mutant (about 3% from the total protein)

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A nucleic acid molecule, comprising:
a nucleic acid sequence which encodes a genetically engineered mutant of an *Aequorea coerulescens* non-fluorescent protein of SEQ ID NO: 2 whose amino acid sequence differs from an amino acid sequence of SEQ ID NO: 2 by at least an amino acid substitution at one of residues 222,
wherein the substitution is E222G (substitution of Glutamic Acid at residue 222 with Glycine),
wherein said mutant has fluorescent properties and an amino acid sequence at least 96% identical, as determined using MegAlign, DNAstar clustal algorithm, to the *Aequorea coerulescens* non-fluorescent protein of SEQ ID NO: 2.

2. A nucleic acid molecule of claim 1, wherein the mutant further comprises one or more amino acid substitutions selected from the group consisting of V11I, N19D, F64L, K101E, E115K, N121S, H148Q, F165L, E172K, E172A, T206A, F221L and K238Q.

3. A nucleic acid molecule of claim 2, wherein said nucleic acid molecule encodes a fluorescent protein comprising an amino acid sequence selected from the group consisting of SEQ ID NOs: 04, 06, 08, 10, 12, and 24.

4. An expression cassette comprising
(a) a transcriptional initiation region functional in an expression host;
(b) the nucleic acid molecule according to claim 1; and
(c) a transcriptional termination region functional in said expression host.

5. An expression cassette comprising
  (a) a transcriptional initiation region functional in an expression host;
  (b) the nucleic acid molecule according to claim 2; and
  (c) a transcriptional termination region functional in said expression host.

6. A cell, or progeny thereof, comprising the expression cassette according to claim 4 as part of an extrachromosomal element or integrated into the genome of a host cell as a result of introduction of said expression cassette into said host cell.

7. A cell, or progeny thereof, comprising the expression cassette according to claim 5 as part of an extrachromosomal element or integrated into the genome of a host cell as a result of introduction of said expression cassette into said host cell.

8. A transgenic cell, or progeny thereof, comprising the nucleic acid molecule according to claim 1.

9. A method for detecting a gene expression comprising recombinantly producing a fluorescent protein, which is the mutant encoded by the nucleic acid molecule of claim 1, in a cell and screening the cell for fluorescence to detect gene expression.

10. A transgenic cell, or progeny thereof, comprising the nucleic acid molecule according to claim 2.

11. A method for detecting a gene expression comprising recombinantly producing a fluorescent protein, which is the mutant encoded by the nucleic acid molecule of claim 2, in a cell and screening the cell for fluorescence to detect gene expression.

12. An expression cassette comprising
  (a) a transcriptional initiation region functional in an expression host;
  (b) the nucleic acid molecule according to claim 3; and
  (c) a transcriptional termination region functional in said expression host.

13. A cell, or progeny thereof, comprising the expression cassette of claim 12.

14. A method for labeling or detecting a cell or cell organelle comprising recombinantly producing a fluorescent protein, which is the mutant encoded by the nucleic acid molecule of claim 3, in the cell and screening the cell or organelle for fluorescence to detect label or gene expression.

15. A method for detecting a gene expression comprising recombinantly producing a fluorescent protein, which is the mutant encoded by the nucleic acid molecule of claim 3, in a cell and screening the cell for fluorescence to detect gene expression.

16. A nucleic acid molecule, comprising:
  a nucleic acid sequence which encodes a genetically engineered mutant of an *Aequorea coerulescens* non-fluorescent protein of SEQ ID NO: 2 whose amino acid sequence is SEQ ID NO: 12.

* * * * *

UNITED STATES PATENT AND TRADEMARK OFFICE
CERTIFICATE OF CORRECTION

PATENT NO.       : 7,432,053 B2
APPLICATION NO.  : 10/501629
DATED            : October 7, 2008
INVENTOR(S)      : Gurskaya et al.

Page 1 of 1

It is certified that error appears in the above-identified patent and that said Letters Patent is hereby corrected as shown below:

Column 2, Lines 34-36, please delete "220-II-5" and insert --220-11-5-- therefor;

Column 2, Line 48, please delete "220-II-5" and insert --220-11-5-- therefor;

Column 14, Line 37, delete "Victoria" and insert --victoria-- therefor;

Column 18, Line 30, delete "fluroescence" and insert --fluorescence-- therefor;

Column 22, Line 23, delete "Lippincoft-Scott" and insert --Lippincott-Scott-- therefor;

Column 24, Line 11, delete "coerulecens" and insert --coerulescens-- therefor;

Column 24, Line 12, delete "Victoria" and insert --victoria-- therefor;

Column 24, Line 15, delete "coeruilescens" and insert --coerulescens-- therefor;

Column 24, Line 19, delete "Victoria" and insert --victoria-- therefor;

Column 24, Line 23, delete "Victoria" and insert --victoria-- therefor;

Column 24, Line 28, delete "Victoria" and insert --victoria-- therefor;

Column 24, Line 40, delete "Ile167" and insert --Ile167-- therefor;

Column 27, Lines 19-20, delete "220-II-5" and insert --220-11-5-- therefor;

Column 29, Line 25, delete "Victoria" and insert --victoria-- therefor;

Column 30, Line 16, delete "AgeI" and insert --AgeI-- therefor;

Column 30, Line 16, delete "BglII" and insert -- Bg/II-- therefor.

Signed and Sealed this
Third Day of May, 2011

David J. Kappos
*Director of the United States Patent and Trademark Office*

SEQUENCE LISTING

<160> NUMBER OF SEQ ID NOS: 25

<210> SEQ ID NO 1
<211> LENGTH: 941
<212> TYPE: DNA
<213> ORGANISM: Aequoria coerulescens

<400> SEQUENCE: 1

```
attcaaaaca ctgcagaatt ttggatagat tttcctgcta cttcacacgc ataaaagaca      60
agaaagatga gtaaaggagc agaacttttc actggagttg tcccaattct tattgaatta     120
aatggtgatg ttaatgggca caaattctct gtcagtggag agggcgaagg tgatgcgaca     180
tacggaaagt taacccttaa atttatttgc actacaggaa aactacctgt tccatggcca     240
acacttgtca ctactttctc ttatggtgtt caatgctttt caagatatcc agatcatatg     300
aaacagcatg acttcttcaa gagtgccatg cctgaaggtt atatacagga agaactata      360
tttttcaaag atgacgggaa ctacaagtcg cgtgctgaag tcaagttcga aggtgatacc     420
ctggttaata gaattgagtt aacaggtact gattttaaag aagatggaaa catccttgga     480
aataaaatgg aatacaacta taacgcacat aatgtataca tcatgacaga caaagcaaaa     540
aatggaatca agttaacttt caaaattaga cacaacattg aagatggaag cgttcaactt     600
gcagaccatt atcaacaaaa tactccaatt ggcgatggcc ctgtcctttt accagataac     660
cattacctgt ccacacaatc taccctttcc aaagatccca cgaaaagag agatcacatg      720
atctattttg agtttgtaac agctgctgcg attacacatg gcatggatga attatacaaa     780
taaatgtata gacttcaagt tgacactaac gtgtccgaac aattactaaa atctcagggt     840
tcctggttaa aatcaggctg agatattatt tacatattat agattcatta gaattattta     900
aatactttat agatgttatt gataggggtt attttcttat t                          941
```

<210> SEQ ID NO 2
<211> LENGTH: 238
<212> TYPE: PRT
<213> ORGANISM: Aequoria coerulescens

<400> SEQUENCE: 2

Met Ser Lys Gly Ala Glu Leu Phe Thr Gly Val Val Pro Ile Leu Ile
 1               5                  10                  15

Glu Leu Asn Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Ile Gln Glu Arg
                85                  90                  95

Thr Ile Phe Phe Lys Asp Asp Gly Asn Tyr Lys Ser Arg Ala Glu Val
            100                 105                 110

Lys Phe Glu Gly Asp Thr Leu Val Asn Arg Ile Glu Leu Thr Gly Thr
        115                 120                 125

Asp Phe Lys Glu Asp Gly Asn Ile Leu Gly Asn Lys Met Glu Tyr Asn
    130                 135                 140

```
Tyr Asn Ala His Asn Val Tyr Ile Met Thr Asp Lys Ala Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Thr Leu Ser
        195                 200                 205

Lys Asp Pro Asn Glu Lys Arg Asp His Met Ile Tyr Phe Glu Phe Val
    210                 215                 220

Thr Ala Ala Ala Ile Thr His Gly Met Asp Glu Leu Tyr Lys
225                 230                 235

<210> SEQ ID NO 3
<211> LENGTH: 717
<212> TYPE: DNA
<213> ORGANISM: Aequoria coerulescens

<400> SEQUENCE: 3
atgagtaaag gagcagaact tttcactgga gctgtcccaa ttcttattga attaaatggt    60
gatgttaatg gcacaaaatt ctctgtcagt ggagagggcg aaggtgatgc gacatacgga   120
aagttaaccc ttaaatttat ttgcactaca ggaaaactac ctgttccatg ccaacacttt   180
gtcactactt tctcttatgg tgttcaatgc ttttcaagat atccagatca tatgaaacag   240
catgacttct tcaagagtgc catgcctgaa ggttatatac aggaaagaac tatattttc    300 aaagatgacg ggaactacaa gtcgcgtgct gaagtcaagt tcgaaggtga tacc ctggtt  360 aatagaattg agttaacagg tactgatttt aaagaagatg aaacatcct tggaaataaa    420 atggaataca ctataacgc acataatgta tacatcatga cagacaaagc aaaaaatgga    480
atcaaagtta acttcaaaat tagacacaac attgaagatg gaagcgttca acttgcagac   540
cattatcaac aaaatactcc aattggcgat ggccctgtcc ttttaccaga taaccattac   600
ctgtccacac aatctacct ttccaaagat cccaacgaaa agagagatca catgatctat    660
tttgggtttg taacagctgc tgcgattaca catggcatgg atgaattata caaataa      717

<210> SEQ ID NO 4
<211> LENGTH: 238
<212> TYPE: PRT
<213> ORGANISM: Aequoria coerulescens

<400> SEQUENCE: 4

Met Ser Lys Gly Ala Glu Leu Phe Thr Gly Ala Val Pro Ile Leu Ile
1               5                   10                  15

Glu Leu Asn Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Ile Gln Glu Arg
                85                  90                  95

Thr Ile Phe Phe Lys Asp Asp Gly Asn Tyr Lys Ser Arg Ala Glu Val
            100                 105                 110
```

```
Lys Phe Glu Gly Asp Thr Leu Val Asn Arg Ile Glu Leu Thr Gly Thr
            115                 120                 125

Asp Phe Lys Glu Asp Gly Asn Ile Leu Gly Asn Lys Met Glu Tyr Asn
        130                 135                 140

Tyr Asn Ala His Asn Val Tyr Ile Met Thr Asp Lys Ala Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Thr Leu Ser
        195                 200                 205

Lys Asp Pro Asn Glu Lys Arg Asp His Met Ile Tyr Phe Gly Phe Val
210                 215                 220

Thr Ala Ala Ala Ile Thr His Gly Met Asp Glu Leu Tyr Lys
225                 230                 235
```

<210> SEQ ID NO 5
<211> LENGTH: 717
<212> TYPE: DNA
<213> ORGANISM: Aequoria coerulescens

<400> SEQUENCE: 5

```
atgagtaaag gagcagaact tttcactgga gctgtcccaa ttcttattga attagatggt      60
gatgttaatg gcacaaatt ctctgtcagt ggagagggcg aaggtgatgc gacatacgga     120
aagttaaccc ttaaatttat ttgcactaca ggaaaactac ctgttccatg gccaacactt    180
gtcactactt tctcttatgg tgttcaatgc ttttcaagat atccagatca tatgaaacag    240
catgacttct tcaagagtgc catgcctgaa ggttatatac aggaaagaac tatattttc    300
aaagatgacg gaactacaa gtcgcgtgct gaagtcaagt tcgaaggtga tacccctggtt    360
aatagaattg agttaacagg tactgatttt aaagaagatg gaaacatcct tggaaataaa    420
atggaataca ctataacgc acataatgta tacatcatga cagacaaagc aaaaaatgga    480
atcaaagtta acttcaaaat tagacacaac attgaagatg gaagcgttca acttgcagac    540
cattatcaac aaaatactcc aattggcgat ggccctgtcc ttttaccaga taaccattac    600
ctgtccacac aatctaccct ttccaaagat cccaacgaaa agagagatca catgatctat    660
tttgggtttg taacagctgc tgcgattaca catggcatgg atgaattata caaataa      717
```

<210> SEQ ID NO 6
<211> LENGTH: 238
<212> TYPE: PRT
<213> ORGANISM: Aequoria coerulescens

<400> SEQUENCE: 6

```
Met Ser Lys Gly Ala Glu Leu Phe Thr Gly Ala Val Pro Ile Leu Ile
 1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80
```

```
His Asp Phe Phe Lys Ser Ala Met Pro Glu Gly Tyr Ile Gln Glu Arg
                85                  90                  95
Thr Ile Phe Phe Lys Asp Asp Gly Asn Tyr Lys Ser Arg Ala Glu Val
            100                 105                 110
Lys Phe Glu Gly Asp Thr Leu Val Asn Arg Ile Glu Leu Thr Gly Thr
        115                 120                 125
Asp Phe Lys Glu Asp Gly Asn Ile Leu Gly Asn Lys Met Glu Tyr Asn
    130                 135                 140
Tyr Asn Ala His Asn Val Tyr Ile Met Thr Asp Lys Ala Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Thr Leu Ser
        195                 200                 205
Lys Asp Pro Asn Glu Lys Arg Asp His Met Ile Tyr Phe Gly Phe Val
    210                 215                 220
Thr Ala Ala Ala Ile Thr His Gly Met Asp Glu Leu Tyr Lys
225                 230                 235
```

```
<210> SEQ ID NO 7
<211> LENGTH: 720
<212> TYPE: DNA
<213> ORGANISM: Aequoria coerulescens

<400> SEQUENCE: 7
atgagtaaag gagcagaact tttcactgga attgtcccaa ttcttattga attaaatggt      60
gatgttaatg gcacaaaatt ctctgtcagt ggagagggcg aaggtgatgc gacatacgga     120
aagttaaccc ttaaatttat ttgcactaca ggaaaactat acctgttcc atggccaaca      180
cttgtcacta ctttctctta tggtgttcaa tgcttttcaa gatatccaga tcatatgaaa     240
cagcatgact tcttcaagag tgccatgcct gaaggttata tacaggaaag aactatattt     300
ttcgaagatg acgggaacta caagtcgcgt gctgaagtca agttcgaagg tgataccctg     360
gttaatagaa ttgagttaac aggtactgat tttaagaag atggaaacat ccttggaaat      420
aaaatggaat acaactataa cgcacataat gtatacatca tgacagacaa agcaaaaaat    480
ggaatcaaag ttaacttcaa aattagacac aacattgaag atggaagcgt tcaacttgca     540
gaccattatc aacaaaatac tccaattggc gatggccctg tccttttacc agataaccat    600
tacctgtcca cacaatctac cctttccaaa gatcccaacg aaaagagaga tcacatgatc    660
tattttgggt ttgtaacagc tgctgcgatt acacatggca tggatgaatt atacaaataa    720
```

```
<210> SEQ ID NO 8
<211> LENGTH: 238
<212> TYPE: PRT
<213> ORGANISM: Aequoria coerulescens

<400> SEQUENCE: 8

Met Ser Lys Gly Ala Glu Leu Phe Thr Gly Ile Val Pro Ile Leu Ile
 1               5                  10                  15
Glu Leu Asn Gly Asp Val Asn Gly His Lys Phe Ser Val Ser Gly Glu
                20                  25                  30
Gly Glu Gly Asp Ala Thr Tyr Gly Lys Leu Thr Leu Lys Phe Ile Cys
            35                  40                  45
```

Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Ile Gln Glu Arg
                 85                  90                  95

Thr Ile Phe Phe Glu Asp Asp Gly Asn Tyr Lys Ser Arg Ala Glu Val
            100                 105                 110

Lys Phe Glu Gly Asp Thr Leu Val Asn Arg Ile Glu Leu Thr Gly Thr
        115                 120                 125

Asp Phe Lys Glu Asp Gly Asn Ile Leu Gly Asn Lys Met Glu Tyr Asn
130                 135                 140

Tyr Asn Ala His Asn Val Tyr Ile Met Thr Asp Lys Ala Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Thr Leu Ser
        195                 200                 205

Lys Asp Pro Asn Glu Lys Arg Asp His Met Ile Tyr Phe Gly Phe Val
210                 215                 220

Thr Ala Ala Ala Ile Thr His Gly Met Asp Glu Leu Tyr Lys
225                 230                 235

<210> SEQ ID NO 9
<211> LENGTH: 717
<212> TYPE: DNA
<213> ORGANISM: Aequoria coerulescens

<400> SEQUENCE: 9
atgagtaaag gagcagaact tttcactgga attgtcccaa ttcttattga attaaatggt      60
gatgttaatg gcacaaaatt ctctgtcagt ggagagggcg aaggtgatgc gacatacgga     120
aagttaaccc ttaaatttat ttgcactaca ggaaaactac ctgttccatg gccaacactt     180
gtcactactc tctcttatgg tgttcaatgc ttttcaagat atccagatca tatgaaacag     240
catgacttct tcaagagtgc catgcctgaa ggttatatac aggaaagaac tatattttc      300 gaagatgacg gaactacaa gtcgcgtgct gaagtcaagt tcgaaggtga taccctggtt     360
aatagaattg agttaacagg tactgatttt aaagaagatg gaaacatcct tggaaataaa     420
atggaataca ctataacgc acataatgta tacatcatga cagacaaagc aaaaaatgga     480
atcaaagtta acttcaaaat tagacacaac attgaagatg gaagcgttca acttgcagac     540
cattatcaac aaaatactcc aattggcgat ggccctgtcc ttttaccaga taaccattac     600
ctgtccacac aatctaccct ttccaaagat cccaacgaaa agagagatca catgatctat     660 tttggtttg taacagctgc tgcgattaca catggcatgg atgaattata caaataa       717

<210> SEQ ID NO 10
<211> LENGTH: 238
<212> TYPE: PRT
<213> ORGANISM: Aequoria coerulescens

<400> SEQUENCE: 10

Met Ser Lys Gly Ala Glu Leu Phe Thr Gly Ile Val Pro Ile Leu Ile
 1               5                  10                  15

```
Glu Leu Asn Gly Asp Val Asn Gly His Lys Phe Ser Val Ser Gly Glu
             20                  25                  30
Gly Glu Gly Asp Ala Thr Tyr Gly Lys Leu Thr Leu Lys Phe Ile Cys
         35                  40                  45
Thr Thr Gly Lys Leu Pro Val Pro Trp Pro Thr Leu Val Thr Thr Leu
     50                  55                  60
Ser Tyr Gly Val Gln Cys Phe Ser Arg Tyr Pro Asp His Met Lys Gln
 65                  70                  75                  80
His Asp Phe Phe Lys Ser Ala Met Pro Glu Gly Tyr Ile Gln Glu Arg
                 85                  90                  95
Thr Ile Phe Phe Glu Asp Asp Gly Asn Tyr Lys Ser Arg Ala Glu Val
             100                 105                 110
Lys Phe Glu Gly Asp Thr Leu Val Asn Arg Ile Glu Leu Thr Gly Thr
         115                 120                 125
Asp Phe Lys Glu Asp Gly Asn Ile Leu Gly Asn Lys Met Glu Tyr Asn
    130                 135                 140
Tyr Asn Ala His Asn Val Tyr Ile Met Thr Asp Lys Ala Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Thr Leu Ser
        195                 200                 205
Lys Asp Pro Asn Glu Lys Arg Asp His Met Ile Tyr Phe Gly Phe Val
    210                 215                 220
Thr Ala Ala Ala Ile Thr His Gly Met Asp Glu Leu Tyr Lys
225                 230                 235

<210> SEQ ID NO 11
<211> LENGTH: 717
<212> TYPE: DNA
<213> ORGANISM: Aequoria coerulescens

<400> SEQUENCE: 11
atgagtaaag gagcagaact tttcactgga attgtcccaa ttcttattga attaaatggt    60
gatgttaatg ggcacaaatt ctctgtcagt ggagagggcg aaggtgatgc gacatacgga   120
aagttaaccc ttaaatttat ttgcactaca ggaaaactac ctgttccatg gccaacactt   180
gtcactactc tctcttatgg tgttcaatgc ttttcaagat atccagatca tatgaaacag   240
catgacttct tcaagagtgc catgcctgaa ggttatatac aggaaagaac tatattttc    300
gaagatgacg ggaactacaa gtcgcgtgct gaagtcaagt tcgagggtga tacactggtt   360
aatagaatcg agttaacagg tactgatttt aagaagatg gaaacatcct tggaaataaa    420
atggaataca actataacgc acataatgta tacatcatga cagacaaagc aaaaaatgga   480
atcaaagtta acttcaaaat tagacacaac attgaagatg gaagcgttca acttgcagac   540
cattatcaac aaaatactcc aattggcgat ggccctgtcc ttttaccaga taaccattac   600
ctgtccacac aatctgccct ttccaaagat cccaacgaaa agagagatca catgatctat   660
tttgggtttg taacagctgc tgcgattaca catggcatgg atgaactata caaataa      717

<210> SEQ ID NO 12
<211> LENGTH: 238
<212> TYPE: PRT
<213> ORGANISM: Aequoria coerulescens
```

<400> SEQUENCE: 12

```
Met Ser Lys Gly Ala Glu Leu Phe Thr Gly Ile Val Pro Ile Leu Ile
1               5                   10                  15
Glu Leu Asn Gly Asp Val Asn Gly His Lys Phe Ser Val Ser Gly Glu
            20                  25                  30
Gly Glu Gly Asp Ala Thr Tyr Gly Lys Leu Thr Leu Lys Phe Ile Cys
        35                  40                  45
Thr Thr Gly Lys Leu Pro Val Pro Trp Pro Thr Leu Val Thr Thr Leu
    50                  55                  60
Ser Tyr Gly Val Gln Cys Phe Ser Arg Tyr Pro Asp His Met Lys Gln
65                  70                  75                  80
His Asp Phe Phe Lys Ser Ala Met Pro Glu Gly Tyr Ile Gln Glu Arg
                85                  90                  95
Thr Ile Phe Phe Glu Asp Asp Gly Asn Tyr Lys Ser Arg Ala Glu Val
            100                 105                 110
Lys Phe Glu Gly Asp Thr Leu Val Asn Arg Ile Glu Leu Thr Gly Thr
        115                 120                 125
Asp Phe Lys Glu Asp Gly Asn Ile Leu Gly Asn Lys Met Glu Tyr Asn
    130                 135                 140
Tyr Asn Ala His Asn Val Tyr Ile Met Thr Asp Lys Ala Lys Asn Gly
145                 150                 155                 160
Ile Lys Val Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Ile Tyr Phe Gly Phe Val
    210                 215                 220
Thr Ala Ala Ala Ile Thr His Gly Met Asp Glu Leu Tyr Lys
225                 230                 235
```

<210> SEQ ID NO 13
<211> LENGTH: 717
<212> TYPE: DNA
<213> ORGANISM: Aequoria coerulescens

<400> SEQUENCE: 13

```
atgagtaaag gagcagaact tttcactgga attgtcccaa ttcttattga attaaatggt    60
gatgttaatg gcacaaaatt ctctgtcagt ggagagggcg aaggtgatgc gacatacgga   120
aagttaaccc ttaaatttat ttgcactaca ggaaaaactac ctgttccatg gccaacactt   180
gtcactactc tctcttatgg tgttcaatgc ttttcaagat atccagatca tatgaaacag   240
catgacttct tcaagagtgc catgcctgaa ggttatatac aggaaagaac tatattttc    300
gaagatgacg ggaactacaa gtcgcgtgct gaagtcaagt tcgagggtga taccctggtt   360
aatagaatcg agttaacagg tactgatttt aagaagatg gaaacatcct tggaaataaa    420
atggaataca ctataacgc acataatgta tacatcatga cagacaaagc aaaaaatgga   480
atcaaagtta acttcaaaat tagacacaac attgaagatg gaagcgttca acttgcagac   540
cattatcaac aaaatactcc aattggcgat ggccctgtcc ttttaccaga taaccattac   600
ctgtccacac aatctgccct ttccaaagat cccaacgaaa agagagatca catgatctat   660
tttgagtttg taacagctgc tgcgattaca catggcatgg atgaactata caaataa      717
```

<210> SEQ ID NO 14
<211> LENGTH: 238
<212> TYPE: PRT
<213> ORGANISM: Aequoria coerulescens

<400> SEQUENCE: 14

```
Met Ser Lys Gly Ala Glu Leu Phe Thr Gly Ile Val Pro Ile Leu Ile
  1               5                  10                  15

Glu Leu Asn Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Leu
     50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Ile Gln Glu Arg
                 85                  90                  95

Thr Ile Phe Phe Glu Asp Asp Gly Asn Tyr Lys Ser Arg Ala Glu Val
            100                 105                 110

Lys Phe Glu Gly Asp Thr Leu Val Asn Arg Ile Glu Leu Thr Gly Thr
        115                 120                 125

Asp Phe Lys Glu Asp Gly Asn Ile Leu Gly Asn Lys Met Glu Tyr Asn
    130                 135                 140

Tyr Asn Ala His Asn Val Tyr Ile Met Thr Asp Lys Ala Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Tyr Phe Glu Phe Val
    210                 215                 220

Thr Ala Ala Ala Ile Thr His Gly Met Asp Glu Leu Tyr Lys
225                 230                 235
```

<210> SEQ ID NO 15
<211> LENGTH: 717
<212> TYPE: DNA
<213> ORGANISM: Aequoria coerulescens

<400> SEQUENCE: 15

```
atgagtaaag gagcagaact tttcactgga attgtcccaa ttcttattga attaaatggt      60
gatgttaatg ggcacaaatt ctctgtcagt ggagagggcg aaggtgatgc gacatacgga     120
aagttaaccc ttaaatttat ttgcactaca ggaaaactac ctgttccatg ccaacacttt     180
gtcactactc tctcttatgg tgttcaatgc ttttcaagat atccagatca tatgaaacag     240
catgacttct tcaagagtgc catgcctgaa ggttatatac aggaaagaac tatattttc      300
gaagatgacg ggaactacaa gtcgcgtgct gaagtcaagt tcgagggtga tacccttgtt     360
aatagaatcg agttaacagg tactgatttt aaagaagatg gaaacatcct tggaaataaa     420
atggaataca actataacgc acataatgta tacatcatga cagacaaagc aaaaaatgga     480
atcaaagtta acttcaaaat tagacacaac attgaagatg gaagcgttca acttgcagac     540
```

```
cattatcaac aaaatactcc aattggcgat ggccctgtcc ttttaccaga taaccattac    600
ctgtccacac aatctgccct tccaaagat cccaacgaaa agagagatca catgatcctg    660
tttgagtttg taacagctgc tgcgattaca catggcatgg atgaactata caaataa      717
```

<210> SEQ ID NO 16
<211> LENGTH: 238
<212> TYPE: PRT
<213> ORGANISM: Aequoria coerulescens

<400> SEQUENCE: 16

```
Met Ser Lys Gly Ala Glu Leu Phe Thr Gly Ile Val Pro Ile Leu Ile
 1               5                  10                  15

Glu Leu Asn Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Ile Gln Glu Arg
                85                  90                  95

Thr Ile Phe Phe Glu Asp Asp Gly Asn Tyr Lys Ser Arg Ala Glu Val
            100                 105                 110

Lys Phe Glu Gly Asp Thr Leu Val Asn Arg Ile Glu Leu Thr Gly Thr
        115                 120                 125

Asp Phe Lys Glu Asp Gly Asn Ile Leu Gly Asn Lys Met Glu Tyr Asn
    130                 135                 140

Tyr Asn Ala His Asn Val Tyr Ile Met Thr Asp Lys Ala Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Phe Glu Phe Val
    210                 215                 220

Thr Ala Ala Ala Ile Thr His Gly Met Asp Glu Leu Tyr Lys
225                 230                 235
```

<210> SEQ ID NO 17
<211> LENGTH: 717
<212> TYPE: DNA
<213> ORGANISM: Aequoria coerulescens

<400> SEQUENCE: 17

```
atgagtaaag gagcagaact tttcactgga attgtcccaa ttcttattga attaaatggt     60
gatgttaatg gcacaaaatt ctctgtcagt ggagagggcg aaggtgatgc gacatacgga    120
aagttaaccc ttaaatttat ttgcactaca ggaaaactac ctgttccatg gccaacactt    180
gtcactactc tctcttatgg tgttcaatgc ttttcaagat atccagatca tatgaaacag    240
catgacttct tcaagagtgc catgcctgaa ggttatatac aggaaagaac tatattttc     300 gaagatgacg ggaactacaa gtcgcgtgct gaagtcaagt tcaagggtga taccctggtt    360
```

```
aatagaatcg agttaacagg tactgatttt aaagaagatg gaaacatcct tggaaataaa    420
atggaataca actataacgc acagaatgta tacatcatga cagacaaagc aaaaaatgga    480
atcaaagtta acttcaaaat tagacacaac attgaagatg gaagcgttca acttgcagac    540
cattatcaac aaaatactcc aattggcgat ggccctgtcc ttttaccaga taaccattac    600
ctgtccacac aatctgccct ttccaaagat cccaacgaaa agagagatca catgatcctg    660
ctggagtttg taacagctgc tgcgattaca catggcatgg atgaactata ccaataa      717
```

<210> SEQ ID NO 18
<211> LENGTH: 238
<212> TYPE: PRT
<213> ORGANISM: Aequoria coerulescens

<400> SEQUENCE: 18

```
Met Ser Lys Gly Ala Glu Leu Phe Thr Gly Ile Val Pro Ile Leu Ile
  1               5                  10                  15

Glu Leu Asn Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Leu
 50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Ile Gln Glu Arg
                 85                  90                  95

Thr Ile Phe Phe Glu Asp Asp Gly Asn Tyr Lys Ser Arg Ala Glu Val
            100                 105                 110

Lys Phe Lys Gly Asp Thr Leu Val Asn Arg Ile Glu Leu Thr Gly Thr
        115                 120                 125

Asp Phe Lys Glu Asp Gly Asn Ile Leu Gly Asn Lys Met Glu Tyr Asn
130                 135                 140

Tyr Asn Ala Gln Asn Val Tyr Ile Met Thr Asp Lys Ala Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Leu Leu Glu Phe Val
    210                 215                 220

Thr Ala Ala Ala Ile Thr His Gly Met Asp Glu Leu Tyr Gln
225                 230                 235
```

<210> SEQ ID NO 19
<211> LENGTH: 717
<212> TYPE: DNA
<213> ORGANISM: Aequoria coerulescens

<400> SEQUENCE: 19

```
atgagtaaag gagcagaact tttcactgga attgtcccaa ttcttattga attaaatggt     60
gatgttaatg gcacaaaatt ctctgtcagt ggagagggcg aaggtgatgc gacatacgga    120
aagttaaccc ttaaatttat ttgcactaca ggaaaactac ctgttccatg gccaacactt    180
```

```
gtcgctactc tctcttatgg tgttcaatgc ttttcaagat atccagatca tatgaaacag    240
catgacttct tcaagagtgc catgcctgaa ggttatatac aggaaagaac tatattttc    300 gaagatgacg ggaactacaa gtcgcgtgct gaagtcaagt tcgagggtga tacccctggtt   360 agtagaatcg agttaacagg tactgatttt aaagaagatg aaacatcct tggaaataaa    420 atggaataca actataacgc aactaatgta tacatcatga cagacaaagc aaaaaatgga   480
atcaaagtta acttcaaaat tagacacaac attaaagatg gaagcgttca acttgcagac   540
cattatcaac aaaatactcc aattggcgat ggccctgtcc ttttaccaga taaccattac   600
ctgtccacac aatctgccct tccaaagat cccaacgaaa agagagatca catgatctat    660
tttgagtttg taacagctgc tgcgattaca catggcatgg atgaactata caaataa      717
```

<210> SEQ ID NO 20
<211> LENGTH: 238
<212> TYPE: PRT
<213> ORGANISM: Aequoria coerulescens

<400> SEQUENCE: 20

```
Met Ser Lys Gly Ala Glu Leu Phe Thr Gly Ile Val Pro Ile Leu Ile
  1               5                  10                  15

Glu Leu Asn Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Ala Thr Leu
     50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Ile Gln Glu Arg
                 85                  90                  95

Thr Ile Phe Phe Glu Asp Asp Gly Asn Tyr Lys Ser Arg Ala Glu Val
            100                 105                 110

Lys Phe Glu Gly Asp Thr Leu Val Ser Arg Ile Glu Leu Thr Gly Thr
        115                 120                 125

Asp Phe Lys Glu Asp Gly Asn Ile Leu Gly Asn Lys Met Glu Tyr Asn
    130                 135                 140

Tyr Asn Ala Thr Asn Val Tyr Ile Met Thr Asp Lys Ala Lys Asn Gly
145                 150                 155                 160

Ile Lys Val Asn Phe Lys Ile Arg His Asn Ile Lys Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Tyr Phe Glu Phe Val
    210                 215                 220

Thr Ala Ala Ala Ile Thr His Gly Met Asp Glu Leu Tyr Lys
225                 230                 235
```

<210> SEQ ID NO 21
<211> LENGTH: 717
<212> TYPE: DNA
<213> ORGANISM: Aequoria coerulescens

<400> SEQUENCE: 21

-continued

```
atgagtaaag gagcagaact tttcactgga attgtcccaa ttcttattga attaaatggt    60
gatgttaatg ggcacaaatt ctctgtcagt ggagagggcg aaggtgatgc gacatacgga   120
aagttaaccc ttaaatttat ttgcactaca ggaaaactac ctgttccatg gccaacactt   180
gtcactactc tctcttatgg tgttcaatgc ttttcaagat atccagatca tatgaaacag   240
catgacttct tcaagagtgc catgcctgaa ggttatatac aggaaagaac tatattttc    300 gaagatgacg ggaactacaa gtcgcgtgct gaagtcaagt tcgagggtga taccctggtt   360
aatagaatcg agttaacagg tactgatttt aaagaagatg gaaacatcct tggaaataaa   420
atggaataca actataacgc atctaatgta tacatcatga cagacaaagc aaaaaatgga   480
atcaaagtta acttgaaaat tagacacaac attgcagatg gaagcgttca acttgcagac   540
cattatcaac aaaatactcc aattggcgat ggccctgtcc ttttaccaga taaccattac   600
ctgtccacac aatctgccct ttccaaagat cccaacgaaa agagagatca catgatctat   660
tttgagtttg taacagctgc tgcgattaca catggcatgg atgaactata caaataa     717
```

<210> SEQ ID NO 22
<211> LENGTH: 238
<212> TYPE: PRT
<213> ORGANISM: Aequoria coerulescens

<400> SEQUENCE: 22

```
Met Ser Lys Gly Ala Glu Leu Phe Thr Gly Ile Val Pro Ile Leu Ile
 1               5                  10                  15

Glu Leu Asn Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Ile Gln Glu Arg
                85                  90                  95

Thr Ile Phe Phe Glu Asp Asp Gly Asn Tyr Lys Ser Arg Ala Glu Val
            100                 105                 110

Lys Phe Glu Gly Asp Thr Leu Val Asn Arg Ile Glu Leu Thr Gly Thr
        115                 120                 125

Asp Phe Lys Glu Asp Gly Asn Ile Leu Gly Asn Lys Met Glu Tyr Asn
    130                 135                 140

Tyr Asn Ala Ser Asn Val Tyr Ile Met Thr Asp Lys Ala Lys Asn Gly
145                 150                 155                 160

Ile Lys Val Asn Leu Lys Ile Arg His Asn Ile Ala Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Tyr Phe Glu Phe Val
    210                 215                 220

Thr Ala Ala Ala Ile Thr His Gly Met Asp Glu Leu Ile Lys
225                 230                 235
```

<210> SEQ ID NO 23
<211> LENGTH: 717
<212> TYPE: DNA
<213> ORGANISM: Aequoria coerulescens

<400> SEQUENCE: 23

```
atgagcaagg gcgccgagct gttcaccggc atcgtgccca tcctgatcga gctgaatggc      60
gatgtgaatg ccacaagtt cagcgtgagc ggcgagggcg agggcgatgc cacctacggc     120
aagctgaccc tgaagttcat ctgcaccacc ggcaagctgc ctgtgccctg gcccaccctg     180
gtgaccaccc tgagctacgg cgtgcagtgc ttctcacgct accccgatca catgaagcag     240
cacgacttct tcaagagcgc catgcctgag ggctacatcc aggagcgcac catcttcttc     300
gaggatgacg gcaactacaa gtcgcgcgcc gaggtgaagt tcgagggcga tacccttggtg     360
aatcgcatcg agctgaccgg caccgatttc aaggaggatg caacatcct gggcaataag     420
atggagtaca actacaacgc ccacaatgtg tacatcatga ccgacaaggc caagaatggc     480
atcaaggtga acttcaagat ccgccacaac atcgaggatg cagcgtgca gctggccgac     540
cactaccagc agaatacccc catcggcgat ggccctgtgc tgctgcccga taaccactac     600
ctgtccaccc agagcgccct gtccaaggac cccaacgaga gcgcgatca catgatctac     660
ttcggcttcg tgaccgccgc cgccatcacc cacggcatgg atgagctgta caagtga       717
```

<210> SEQ ID NO 24
<211> LENGTH: 238
<212> TYPE: PRT
<213> ORGANISM: Aequoria coerulescens

<400> SEQUENCE: 24

Met Ser Lys Gly Ala Glu Leu Phe Thr Gly Ile Val Pro Ile Leu Ile
 1               5                  10                  15

Glu Leu Asn Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Leu
     50                  55                  60

Ser Tyr Gly Val Gln Cys Phe Ser Arg Tyr Pro Asp His Met Lys Gln
 65                  70                  75                  80

His Asp Phe Phe Lys Ser Ala Met Pro Glu Gly Tyr Ile Gln Glu Arg
                 85                  90                  95

Thr Ile Phe Phe Glu Asp Asp Gly Asn Tyr Lys Ser Arg Ala Glu Val
            100                 105                 110

Lys Phe Glu Gly Asp Thr Leu Val Asn Arg Ile Glu Leu Thr Gly Thr
        115                 120                 125

Asp Phe Lys Glu Asp Gly Asn Ile Leu Gly Asn Lys Met Glu Tyr Asn
    130                 135                 140

Tyr Asn Ala His Asn Val Tyr Ile Met Thr Asp Lys Ala Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Ile Tyr Phe Gly Phe Val

-continued

```
                210                 215                 220
Thr Ala Ala Ala Ile Thr His Gly Met Asp Glu Leu Tyr Lys
225                 230                 235

<210> SEQ ID NO 25
<211> LENGTH: 238
<212> TYPE: PRT
<213> ORGANISM: Aequoria coerulescens

<400> SEQUENCE: 25

Met Ser Lys Gly Glu Glu Leu Phe Thr Gly Val Val Pro Ile Leu Val
 1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Phe
 50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```